(12) United States Patent
Fukui et al.

(10) Patent No.: US 6,858,640 B2
(45) Date of Patent: Feb. 22, 2005

(54) TRICYCLIC INDOLE COMPOUNDS HAVING AFFINITY FOR SEROTONIN RECEPTOR

(75) Inventors: Yoshikazu Fukui, Osaka (JP); Makoto Adachi, Osaka (JP); Takashi Sasatani, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 75 days.

(21) Appl. No.: 10/312,818

(22) PCT Filed: Sep. 17, 2001

(86) PCT No.: PCT/JP01/08049

§ 371 (c)(1),
(2), (4) Date: Dec. 31, 2002

(87) PCT Pub. No.: WO02/24641

PCT Pub. Date: Mar. 28, 2002

(65) Prior Publication Data

US 2003/0236295 A1 Dec. 25, 2003

(30) Foreign Application Priority Data

Sep. 22, 2000 (JP) ........................................ 2000-287809

(51) Int. Cl.[7] ..................... A61K 31/40; C07D 491/044
(52) U.S. Cl. ....................................... 514/411; 548/430
(58) Field of Search ........................... 548/430; 514/411

(56) References Cited

FOREIGN PATENT DOCUMENTS

EP 738513 10/1996
WO 95/28403 10/1995

*Primary Examiner*—Johann Richter
*Assistant Examiner*—Ebenezer Sackey
(74) *Attorney, Agent, or Firm*—Wenderoth, Lind & Ponack, L.L.P.

(57) ABSTRACT

Having an affinity against serotonine receptors, compound (I) shown below is useful as a therapeutic agent against various kinds of diseases of central nervous systems;

(I)

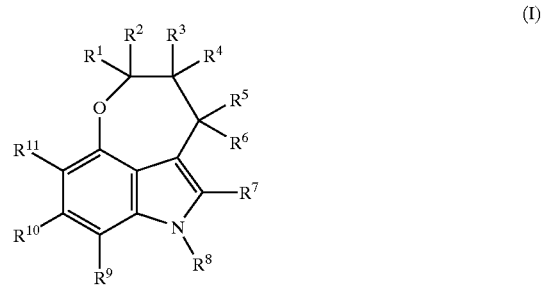

(wherein $R^1$ is hydrogen; $R^2$ is hydrogen or lower alkyl; $R^3$ is hydrogen, —$COOR^{12}$ and so on; $R^4$ is hydrogen, lower alkyl and so on, or $R^3$ and $R^4$ taken together may form =O or =S; $R^5$ is hydrogen, or $R^3$ and $R^5$ taken together may form a bond; $R^6$ is hydrogen, —$COOR^{24}$ and so on; $R^7$ is hydrogen, halogen, lower alkyl and so on; $R^8$ is hydrogen, lower alkyl, cycloalkyl and so on; $R^9$, $R^{10}$ and $R^{11}$ are each independently hydrogen, halogen, lower alkyl and so on).

22 Claims, No Drawings

TRICYCLIC INDOLE COMPOUNDS HAVING AFFINITY FOR SEROTONIN RECEPTOR

This application is a U.S. national stage of International Application No. PCT/JP01/08049 filed Sep. 17, 2001.

1. Techinical Field

The present invention is related to tricyclic indole compounds. Having an affinity against serotonin receptors, the present compounds are useful as medicines, for example, a therapeutic agent for diseases of central nervous system thereof and useful as synthetic intermediates thereof.

2. Background Art

Serotonin (5-hydroxytryptamine) is one of amines, which exists in living body, and has a lot of physiological activities. For example, serotonin is located in granule cell of intestinal basal and promotes the movement of the intestinal tract. And also, on an occasion of bleeding, serotonin is released from platelets into blood and concerned with hemostasis by contracting blood capillary. Apart from this, serotonin works as a neurotransmitter in brain and takes part in modulating mental action, limit of pain, body-temperature and sleep-awakening cycle thereof, through serotonin receptors [*Physiol. Rev.* 72(1992) 165–229].

It has been reported that serotonin receptors are classified mainly to seven families and by including their subtypes, at least 14 kinds of receptors have been identified until now. Each receptor is reported to be concerned with various kinds of physiological functions and diseases [*Pharmacol. Rev.* 46(1994) 157–203]. Displaying to have agonistic or antagonistic activities, an agent having a binding affinity against serotonin receptors, is expected to be a therapeutic or prophylactic medicament. [*Pharmacol.Rev.* 43(1991) 509–525].

Among them, $5\text{-}HT_{5A}$, $5\text{-}HT_{5B}$, $5\text{-}HT_6$, and $5\text{-}HT_7$ are receptors which have been recently identified and cloned [*FEBS Lett.* 355(1994) 242–6, *FEBS Lett.* 333(1993) 25–31, *J. Neurochem.* 66(1996) 47–56, *Neuron*, 11(1993) 449–458] and there is few report about the selective agonist and antagonist. Each of these receptors has already been known to be located mainly in central nervous system. For example, it has been reported that $5\text{-}HT_{5A}$ and $5\text{-}HT_{5B}$ receptors are located in hippocampus and cerebral cortex, which are profoundly concerned with learning and memory [*FEBS Lett.* 355 (1994) 242–6, *FEBS Lett.* 333 (1993) 25–31], $5\text{-}HT_6$ receptor is located in corpus striatum, which is concerned with motor function [*J. Neurochem.* 66 (1996) 47–56], and $5\text{-}HT_7$ receptor is located in suprachiasmatic nucleus, which is concerned with mammalian biological clock [*Neuron*, 11(1993) 449–458]. Therefore, there is a possibility for the selective agonist or antagonist against the receptor to be a therapeutic agent for dementia, Parkinson's disease, psychosis or diseases concerning circannual rhythm thereof. Selective agonists and antagonists against serotonin receptors other than $5\text{-}HT_{5A}$, $5\text{-}HT_{5B}$, $5\text{-}HT_6$ and $5\text{-}HT_7$ receptors have already been launched as therapeutic agents for various kinds of diseases.

Furthermore, indole derivatives having an affinity against serotonin receptors have been disclosed; for example, compounds of a 4-membered ring type are disclosed in WO 96/32944, WO 95/28403, EP 0738513 and so on and compounds of a 3-membered ring type are disclosed in GB 2341549, WO 98/00400, JP 99-189585A and so on. However, these indole derivatives do not contain oxygen as an ring element. Moreover, naturally occurring heterocyclyl type of indole derivatives are described in WO 00/59909.

Under the situations mentioned above, development of novel compounds having an affinity against serotonin receptors and medicines containing them have been desired.

DISCLOSURE OF INVENTION

The present inventors have intensively studied to find that tricyclic indole compounds have an affinity against serotonin receptors, and accomplished the present invention shown below.

(1) A compound, prodrug, pharmaceutically acceptable salt or solvate thereof of the formula:

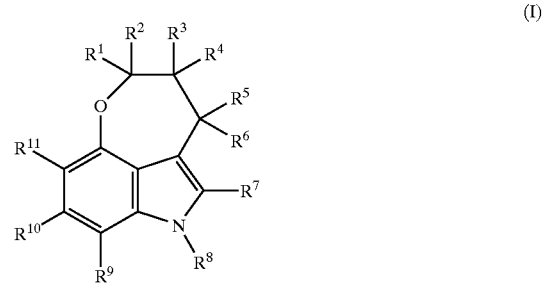

(I)

wherein $R^1$ is hydrogen;

$R^2$ is hydrogen or lower alkyl;

$R^3$ is hydrogen, —COOR$^{12}$ ($R^{12}$ is hydrogen or ester residue) or —CN;

$R^4$ is hydrogen, lower alkyl, —COOR$^{13}$ ($R^{13}$ is hydrogen or ester residue), —CONR$^{14}$R$^{15}$ ($R^{14}$ and $R^{15}$ are each independently hydrogen, lower alkyl, cycloalkyl, lower alkenyl, optionally substituted aralkyl, optionally substituted aryl, or optionally substituted heteroaryl, or $R^{14}$ and $R^{15}$ taken together with a neighboring nitrogen atom may form 5- to 7-membered heterocycle), —CN, —NO$_2$, —NR$^{16}$R$^{17}$ ($R^{16}$ and $R^{17}$ are each independently hydrogen, —CN, optionally substituted lower alkyl, cycloalkyl, cycloalkyl(lower)alkyl, lower alkenyl, optionally substituted aralkyl, optionally substituted aryl, optionally substituted heteroaryl, or optionally substituted amino, or $R^{16}$ and $R^{17}$ taken together with a neighboring nitrogen atom may form optionally substituted 5- to 7-membered heterocycle), —NR$^{18}$COR$^{19}$ ($R^{18}$ and $R^{19}$ are each independently hydrogen, optionally substituted lower alkyl, cycloalkyl, cycloalkyl lower alkyl, lower alkenyl, optionally substituted aralkyl, optionally substituted aryl, or optionally substituted heteroaryl), —NR$^{20}$COOR$^{21}$ ($R^{20}$ is hydrogen, lower alkyl, cycloalkyl, cycloalkyl(lower)alkyl, lower alkenyl, optionally substituted aralkyl, optionally substituted aryl, or optionally substituted heteroaryl; $R^{21}$ is ester residue), —NR$^{22}$SO$_2$R$^{23}$ ($R^{22}$ is hydrogen, lower alkyl, cycloalkyl, cycloalkyl(lower)alkyl, lower alkenyl, optionally substituted aralkyl, optionally substituted aryl, or optionally substituted heteroaryl; $R^{23}$ is lower alkyl, cycloalkyl, lower alkenyl, optionally substituted aralkyl, optionally substituted aryl, optionally substituted heteroaryl, or lower alkylamino), —OH, lower alkoxy, —SH, or lower alkylthio, or $R^3$ and $R^4$ taken together may form =O, =S, or lower alkylenedioxy;

$R^5$ is hydrogen, or $R^3$ and $R^5$ taken together may form a bond;

$R^6$ is hydrogen, —COOR$^{24}$ ($R^{24}$ is hydrogen or ester residue), —CN, or —CH$_2$NR$^{25}$R$^{26}$ ($R^{25}$ and $R^{26}$ are each independently hydrogen, lower alkyl, cycloalkyl, or lower alkenyl);

$R^7$ is hydrogen, halogen, —CN, optionally substituted lower alkyl, cycloalkyl, cycloalkyl(lower)alkyl, optionally substituted lower alkenyl, optionally substituted aralkyl, optionally substituted aryl, optionally substituted heteroaryl, optionally substituted amino, —COOR$^{34}$ (R$^{34}$ is hydrogen or ester residue), —COR$^{35}$ (R$^{35}$ is hydrogen, lower alkyl, cycloalkyl, lower alkenyl, optionally substituted aralkyl, optionally substituted amino, optionally substituted aryl, or optionally substituted heteroaryl) or —CHNOH;

R$^8$ is hydrogen, optionally substituted lower alkyl, cycloalkyl, cycloalkyl(lower)alkyl, lower alkenyl, optionally substituted aralkyl, optionally substituted aryl, optionally substituted heteroaryl, —COR$^{27}$ (R$^{27}$ is hydrogen, lower alkyl, cycloalkyl, lower alkenyl, optionally substituted aralkyl, optionally substituted aryl, or optionally substituted heteroaryl, —COOR$^{28}$ (R$^{28}$ is ester residue), —SO$_2$R$^{29}$ (R$^{29}$ is lower alkyl, cycloalkyl, optionally substituted lower alkenyl, optionally substituted aralkyl, optionally substituted aryl, optionally substituted heteroaryl) or tri-lower alkylsilyl;

R$^9$, R$^{10}$ and R$^{11}$ are each independently hydrogen, halogen, optionally substituted lower alkyl, cycloalkyl, cycloalkyl(lower)alkyl, optionally substituted lower alkenyl, lower alkoxy, —OH, —CN, —SR$^{30}$ (R$^{30}$ is hydrogen or lower alkyl), —CONH$_2$, —CHO, —CHNOH, —COOR$^{31}$ (R$^{31}$ is hydrogen or ester residue), —NR$^{32}$R$^{33}$ (R$^{32}$ and R$^{33}$ are each independently hydrogen or lower alkyl), optionally substituted aryl, or optionally substituted heteroaryl.

(2) A compound, prodrug, pharmaceutically acceptable salt, or solvate thereof according to the above 1, wherein R$^2$ is hydrogen.

(3) A compound, prodrug, pharmaceutically acceptable salt, or solvate thereof according to the above 1, wherein R$^3$ is hydrogen.

(4) A compound, prodrug, pharmaceutically acceptable salt, or solvate thereof according to the above 1, wherein R$^5$ is hydrogen.

(5) A compound, prodrug, pharmaceutically acceptable salt or solvate thereof, according to the above 1, wherein R$^3$ and R$^5$ taken together may form a bond.

(6) A compound, prodrug, pharmaceutically acceptable salt or solvate thereof, according to the above 1, wherein R$^3$ and R$^4$ taken together may form =O, =S or lower alkylenedioxy.

(7) A compound, prodrug, pharmaceutically acceptable salt or solvate thereof, according to the above 1, wherein R$^4$ represents —COOR$^{13}$ (R$^{13}$ is hydrogen or lower alkyl), —NR$^{16}$R$^{17}$ (R$^{16}$ and R$^{17}$ are each independently hydrogen, optionally substituted lower alkyl, cycloalkyl, lower alkenyl, optionally substituted aralkyl, optionally substituted amino, or R$^{16}$ and R$^{17}$ taken together may form an optionally substituted 5 to 7 membered heterocyclyl ring with the neighboring nitrogen atom), —NR$^{18}$COR$^{19}$ (R$^{18}$ and R$^{19}$ are each independently hydrogen, optionally substituted lower alkyl or optionally substituted aralkyl), —NR$^{20}$COOR$^{21}$ (R$^{20}$ is hydrogen, or lower alkyl; R$^{21}$ is an ester moiety), —NR$^{22}$SO$_2$R$^{23}$ (R$^{22}$ is hydrogen; R$^{23}$ is lower alkyl or lower alkylamino), —OH, or lower alkoxy.

(8) A compound, prodrug, pharmaceutically acceptable salt or solvate thereof, according to the above 1, wherein R$^4$ is —COOR$^{13}$ (R$^{13}$ is hydrogen or methyl), —NR$^{16}$R$^{17}$ (R$^{16}$ is hydrogen or lower alkyl, R$^{17}$ is hydrogen, optionally substituted lower alkyl, cycloalkyl, lower alkenyl, optionally substituted aralkyl, optionally substituted amino, optionally substituted amino or R$^{16}$ and R$^{17}$ are taken together may form an optionally substituted 5 to 7 membered heterocyclyl ring with the neighboring nitrogen atom), —NR$^{18}$COR$^{19}$ (R$^{18}$ is hydrogen, R$^{19}$ is hydrogen, optionally substituted lower alkyl or optionally substituted aralkyl), —NR$^{20}$COOR$^{21}$ (R$^{20}$ is hydrogen or methyl; R$^{21}$ is methyl), —NR$^{22}$SO$_2$R$^{23}$ (R$^{22}$ is hydrogen; R$^{23}$ is methyl or methylamino), —OH, or lower alkoxy.

(9) A compound, prodrug, pharmaceutically acceptable salt or solvate thereof, according to the above 1, wherein R$^4$ is —NH$_2$, —NHCH$_3$ or —N(CH$_3$)$_2$.

(10) A compound, prodrug, pharmaceutically acceptable salt or solvate thereof, according to the above 1, wherein R$^6$ is hydrogen, COOCH$_3$, COOCH$_2$CH$_3$, CN, or CH$_2$NH$_2$.

(11) A compound, prodrug, pharmaceutically acceptable salt or solvate thereof, according to the above 1, wherein R$^6$ is hydrogen.

(12) A compound, prodrug, pharmaceutically acceptable salt or solvate thereof, according to the above 1, wherein R$^7$ is hydrogen, lower alkyl, halogen, phenyl, —COOR$^{34}$ (R$^{34}$ is mentioned before), —CHO or —CHNOH.

(13) A compound, prodrug, pharmaceutically acceptable salt or solvate thereof, according to the above 1, wherein R$^7$ is hydrogen, methyl, ethyl, halogen or phenyl.

(14) A compound, prodrug, pharmaceutically acceptable salt or solvate thereof, according to the above 1, wherein R$^8$ is hydrogen, optionally substituted lower alkyl, —COR$^{27}$ (R$^{27}$ is hydrogen, lower alkyl, cycloalkyl, lower alkenyl, optionally substituted aralkyl, optionally substituted aryl, or optionally substituted heteroaryl), —COOR$^{28}$ (R$^{28}$ is ester moiety), or —SO$_2$R$^{29}$ (R$^{29}$ is lower alkyl, cycloalkyl, optionally substituted lower alkenyl, optionally substituted aralkyl, optionally substituted aryl, optionally substituted heteroaryl), or tri-lower alkylsilyl.

(15) A compound, prodrug, pharmaceutically acceptable salt or solvate thereof, according to the above 1, wherein R$^8$ is hydrogen or —SO$_2$R$^{29}$ (R$^{20}$ is mentioned before)

(16) A compound, prodrug, pharmaceutically acceptable salt or solvate thereof, according to the above 1, wherein all of R$^9$, R$^{10}$ and R$^{11}$ are hydrogen.

(17) A compound, prodrug, pharmaceutically acceptable salt or solvate thereof, according to the above 1, wherein R$^2$ is hydrogen; R$^3$ and R$^5$ are both hydrogen or taken together may form a bond.

(18) A compound, prodrug, pharmaceutically acceptable salt or solvate thereof, according to the above 16 and 17, wherein R$^6$ is hydrogen, COOCH$_3$, COOCH$_2$CH$_3$, CN, or CH$_2$NH$_2$; R$^7$ is hydrogen, lower alkyl, halogen or phenyl; R$^8$ is hydrogen, lower alkyl, COPh, or SO$_2$Ph (Ph represents phenyl).

(19) A compound, prodrug, pharmaceutically acceptable salt or solvate thereof, according to the above 1, wherein R$^9$ is hydrogen or halogen.

(20) A compound, prodrug, pharmaceutically acceptable salt or solvate thereof, according to the above 1, wherein R$^9$ is hydrogen.

(21) A compound, prodrug, pharmaceutically acceptable salt or solvate thereof, according to the above 1, wherein R$^{10}$ is hydrogen.

(22) A compound, prodrug, pharmaceutically acceptable salt or solvate thereof, according to the above 1, wherein R$^{11}$ is hydrogen, halogen, lower alkyl, optionally substituted lower alkenyl, —CN, —SR$^{30}$ (R$^{30}$ is hydrogen or lower alkyl), —CONH$_2$, —CHO, —CHNOH, —NR$^{32}$R$^{33}$ (R$^{32}$ and R$^{33}$ are each independently hydrogen or lower alkyl) or aryl.

(23) A compound, prodrug, pharmaceutically acceptable salt or solvate thereof, according to the above 1, wherein R$^{11}$ is hydrogen, halogen, methyl, —CN, or —CONH$_2$.

(24) A compound, prodrug, pharmaceutically acceptable salt or solvate thereof, according to the above 1, wherein $R^1$, $R^2$, $R^3$, $R^5$, $R^6$, $R^9$, and $R^{10}$ is hydrogen; $R^4$ is —$NH_2$, —$NHCH_3$, or —$N(CH_3)_2$; $R^7$ is hydrogen, halogen, lower alkyl, or phenyl; $R^8$ is hydrogen or —$SO_2R^{29}$ ($R^{29}$ is mentioned before); $R^{11}$ is hydrogen, halogen, lower alkyl, —CN, or —$CONH_2$.

(25) A pharmaceutical composition containing a compound, prodrug, pharmaceutically acceptable salt or solvate thereof according to any one of the above 1–24.

(26) A therapeutic or prophylactic medicament against the serotonin receptors mediated diseases, comprising a compound, prodrug, pharmaceutically acceptable salt or solvate thereof according to any one of the above 1–24.

(27) A therapeutic or prophylactic medicament according to the above 26, wherein the serotonine receptor is a 5-$HT_6$ receptor.

(28) A therapeutic or prophylactic medicament according to the above 26, wherein the disease is that of central nervous system.

(29) A therapeutic or prophylactic medicament according to the above 28, wherein the disease of the central nervous system is schizophrenia, Alzheimer's disease, Parkinson's disease, depression, anxiety, pain or migraine.

(30) A method for treating or preventing the serotonin receptors mediated diseases, which comprises administrating to said mammal an effective amount of a compound, prodrug, pharmaceutically acceptable salt or solvate thereof according to any one of the above 1–24.

(31) Use of a compound, prodrug, pharmaceutically acceptable salt or solvate thereof according to any one of the above 1–24, in order to prepare a therapeutic or prophylactic medicament for the serotonin receptors mediated diseases.

BEST MODE FOR CARRYING OUT THE INVENTION

Each group of compound (I) is explained below. Each term used herein is defined to have meanings described below in either case of a single or a joint use with other terms, unless otherwise noted.

"Halogen" refers to F, Cl, Br, I.

"Lower alkyl" includes a straight-chain and branched-chain $C_1$–$C_6$ alkyl group and refers to methyl, ethyl, n-propyl, i-propyl, n-butyl, i-butyl, sec-butyl, tert-butyl, n-pentyl, i-pentyl, neo-pentyl, tert-pentyl, n-hexyl and the like, preferably a $C_1$–$C_4$ alkyl group and more preferably a $C_1$–$C_3$ alkyl group, such as methyl, ethyl, n-propyl, and i-propyl.

"Lower alkenyl" includes a straight-chain and branched-chain $C_2$–$C_6$ alkenyl group and refers to vinyl, allyl, 1-propenyl, 2-butenyl, 3-butenyl, 1-pentenyl, prenyl, 2-hexenyl and the like, preferably vinyl, allyl or prenyl and the like.

"Lower alkoxy" includes oxy groups binding to an above mentioned lower alkyl group, and refers to methoxyl, ethoxyl, n-propoxyl, i-propoxyl, tert-butoxy, pentyloxy, hexyloxy and the like, preferably a $C_1$–$C_4$ alkoxyl group and more preferably a $C_1$–$C_3$ alkoxyl group such as methoxyl, ethoxyl, n-propoxyl, and i-propoxyl.

"Cycloalkyl" includes $C_3$–$C_8$ cycloalkyl and refers to cyclopropyl, cyclobutyl, cyclopentyl, cyclohexyl, cycloheptyl, cyclooctyl and the like, preferably a $C_5$–$C_7$ cycloalkyl group such as cyclopentyl, cyclohexyl, and cycloheptyl.

"Cycloalkyl(lower)alkyl" means an above mentioned lower alkyl group bound with an above mentioned cycloalkyl group and refers to cyclopropylmethyl, 2-cyclopropyl ethyl and the like.

"Lower alkylthio" includes a thio group bound with an above mentioned lower alkyl group and refers to methylthio, ethylthio, i-propylthio, tert-butylthio, pentylthio, hexylthio and the like, preferably methylthio.

"Aryl" used herein means a single or fused aromatic hydrocarbon ring system and refers to phenyl, naphthyl (such as α-naphthyl, and β-naphthyl), anthryl, indenyl, phenanthryl and the like, preferably phenyl or naphthyl.

"Lower alkylenedioxy" includes a straight-chain and branched-chain $C_1$–$C_6$ alkylendioxy group, preferably methylenedioxy, ethylenedioxy, or trimethylenedioxy, more preferably ethylenedioxy.

"Aralkyl" used herein means a lower alkyl group bound with an above mentioned aryl group, refers to benzyl, phenethyl, phenylpropyl (such as 3-phenylpropyl), naphthylmethyl (such as α-naphthylmethyl), anthrylmethyl such as 9-anthrylmethyl and the like.

"Heteroaryl" used herein means a single or polycyclic aromatic ring system in which the ring contains the same or different heteroatom selected from the group of O, S and N.

The single aromatric ring system includes a 5- to 7-membered ring moiety in which the heterocycle contains 1 to 4 heteroatoms and refers to furyl, thienyl, tetrazolyl, pyrrolyl, pyrazolyl, imidazolyl, oxazolyl, thiazolyl, thiadiazolyl, pyridinyl, oxazinyl, triazinyl and the like, preferably 2-furyl, 3-furyl, 2-thienyl, 3-thienyl, 2-pyrrolyl, 3-pyrrolyl, 2-pyridinyl, 3-pyridinyl, or 4-pyridinyl.

Polycyclic aromatic ring system includes a di- or tri-heterocyclic moiety in which the heterocycle contains 1 to 5 heteroatoms and refers to benzofuranyl, isobenzofuranyl, benzothienyl, indolyl, isoindolyl, indazolyl, benzimidazolyl, benzoxazoly, benzothiazolyl, benzotriazolyl and the like.

5- to 7-Membered heterocycle formed by "$R^{14}$ and $R^{15}$" or "$R^{16}$ and $R^{17}$" taken together with the neighboring nitrogen, refers to pyrrolydine, piperidine, azepine, piperazine, morpholine and the like, preferably pyrrolydine, piperazine or morpholine.

Substituents on the aryl, heteroaryl or heterocyclyl ring refer to halogen, hydroxy, amino, carboxy, cyano, nitro, carbamoyl, sulfamoyl, lower alkyl (such as methyl or ethyl), halo-lower alkyl (such as —$CCF_3$), lower alkyl-carbamoyl (such as methylcarbamoyl), lower alkyl-sulfamoyl (such as methylsulfamoyl), lower alkoxy (such as methoxyl), lower alkoxycarbonyl (such as ethoxylcarbonyl), a 5- to 7-membered heterocyclyl group such as isoxazolyl and the like, preferably halogen, methyl, methoxyl, trihalo-methyl such as trifluoromethyl, preferably 1 to 3 of these groups can be substituted.

"Ester" residue refers to lower alkyl, optionally substituted aralkyl and the like, preferably, methyl, ethyl, n-propyl, i-propyl, tert-butyl, benzyl and the like.

"Lower alkyl" or "lower alkenyl" can be optionally substituted, in which a substituent refers to hydroxy, halogen, amino and optionally mono- or di-lower alkyl substituted carbamoyl (such as carbamoyl, and dimethylcarbamoyl), phenyl, phenylamino, cyclohexylamino, lower alkoxy, lower alkoxycarbonyl such as methoxylcarbonyl and the like.

An optional substitutent on amino groups refers to lower alkyl, lower alkoxycarbonyl and the like.

Preferred examples are shown below.
(1) both of $R^1$ and $R^5$ are hydrogen.
(2) all of $R^1$, $R^3$, and $R^5$ are hydrogen.

(3) $R^1$ is hydrogen; $R^3$ and $R^4$ are taken together may form a bond.
(4) $R^1$ is hydrogen; $R^3$ and $R^4$ are taken together may form =O or =S.

Other preferred examples are shown in following tables.

TABLE 1

| $R^2$ | $R^3$ | $R^4$ | $R^6$ |
|---|---|---|---|
| H | H | H | H |
| methyl | $COOR^{12}$ | methyl | $COOR^{24}$ |
| ethyl | CN | ethyl | CN |
| n-propyl | | n-propyl | $CH_2NR^{25}R^{26}$ |
| i-propyl | | i-propyl | |
| | | $COOR^{13}$ | |
| | | $CONR^{14}R^{15}$ | |
| | | CN | |
| | | $NO_2$ | |
| | | $NR^{16}R^{17}$ | |
| | | $NR^{18}COR^{19}$ | |
| | | $NR^{20}COOR^{21}$ | |
| | | $NR^{22}SO_2R^{23}$ | |
| | | OH | |
| | | methoxyl | |
| | | ethoxyl | |
| | | n-propoxyl | |
| | | i-propoxyl | |
| | | SH | |
| | | methyl thio | |
| | | ethyl thio | |
| | | n-propylthio | |
| | | i-propylthio | |
| —$O(CH_2)_2O$— | | | |

TABLE 2

| $R^7$ | $R^8$ | $R^9$, $R^{10}$, $R^{11}$ |
|---|---|---|
| H | H | H |
| F | methyl | F |
| Cl | ethyl | Cl |
| Br | n-propyl | Br |
| I | i-propyl | I |
| methyl | cyclopropylmethyl | methyl |
| ethyl | cyclopentyl | ethyl |
| n-propyl | cyclohexyl | n-propyl |
| i-propyl | cycloheptyl | i-propyl |
| cyclopropylmethyl | vinyl | cyclopropylmethyl |
| cyclopentyl | allyl | cyclopentyl |
| cyclohexyl | prenyl | cyclohexyl |
| cycloheptyl | benzyl | cycloheptyl |
| vinyl | phenethyl | vinyl |
| allyl | phenyl | allyl |
| prenyl | 2-furyl | prenyl |
| benzyl | 3-furyl | OH |
| phenethyl | 2-pyridinyl | methoxyl |
| phenyl | 3-pyridinyl | ethoxyl |
| 2-furyl | 4-pyridinyl | n-propoxyl |
| 3-furyl | 2-pyrrolyl | i-propoxyl |
| 2-pyridinyl | 3-pyrrolyl | CN |
| 3-pyridinyl | 2-thienyl | CHO |
| 4-pridinyl | 3-thienyl | $SCH_3$ |
| 2-pyrrolyl | $COR^{27}$ | CH=N—OH |
| 3-pyrrolyl | $COOR^{28}$ | $CONH_2$ |
| 2-thienyl | $SO_2R^{29}$ | phenyl |
| 3-thienyl | $Si(iPr)_3$ | $CH=CHCO_2CH_3$ |
| CN | | |

TABLE 3

| $R^{12}$, $R^{13}$ | $R^{14}$, $R^{16}$ | $R^{15}$, $R^{17}$ |
|---|---|---|
| H | H | H |
| methyl | methyl | methyl |
| ethyl | ethyl | ethyl |
| n-propyl | n-propyl | n-propyl |
| i-propyl | i-propyl | i-propyl |
| t-butyl | cyclopropyl methyl | cyclopropylmethyl |
| benzyl | cyclopentyl | cyclopentyl |
| | cyclohexyl | cyclohexyl |
| | cycloheptyl | cycloheptyl |
| | allyl | allyl |
| | prenyl | prenyl |
| | benzyl | benzyl |
| | phenethyl | phenethyl |
| | phenyl | phenyl |
| | 2-furyl | 2-furyl |
| | 3-furyl | 3-furyl |
| | 2-pyridinyl | 2-pyridinyl |
| | 3-pyridinyl | 3-pyridinyl |
| | 4-pyridinyl | 4-pyridinyl |
| | 2-pyrrolyl | 2-pyrrolyl |
| | 3-pyrrolyl | 3-pyrrolyl |
| | 2-thienyl | 2-thienyl |
| | 3-thienyl | NHBoc |
| | | cyclopropyl |
| | | $CH_2CF_3$ |
| | | —$CH_2CH_2CH_2CH_2$— |
| | | —$CH_2CH_2CH_2CH_2CH_2$— |
| | | —$CH_2CH_2CH_2CH_2CH_2CH_2$— |
| | | —CH=CH—CH=CH— |
| | | —$CH_2CH_2NHCH_2CH_2$— |
| | | —$CH_2CH_2NCH_3CH_2CH_2$— |
| | | —$CH_2CH_2OCH_2CH_2$— |

TABLE 4

| $R^{21}$ | $R^{18}$, $R^{19}$, $R^{20}$, $R^{22}$ | $R^{23}$ |
|---|---|---|
| methyl | H | methyl |
| ethyl | methyl | ethyl |
| n-propyl | ethyl | n-propyl |
| i-propyl | n-propyl | i-propyl |
| t-butyl | i-propyl | cyclopropylmethyl |
| benzyl | cyclopropylmethyl | cyclopentyl |
| | cyclopentyl | cyclohexyl |
| | cyclohexyl | cycloheptyl |
| | cycloheptyl | vinyl |
| | allyl | allyl |
| | prenyl | prenyl |
| | benzyl | benzyl |
| | phenethyl | phenethyl |
| | phenyl | phenyl |
| | 2-furyl | 2-furyl |
| | 3-furyl | 3-furyl |
| | 2-pyridinyl | 2-pyridinyl |
| | 3-pyridinyl | 3-pyridinyl |
| | 4-pyridinyl | 4-pyridinyl |
| | 2-pyrrolyl | 2-pyrrolyl |
| | 3-pyrrolyl | 3-pyrrolyl |
| | 2-thienyl | 2-thienyl |
| | 3-thienyl | 3-thienyl |
| | $CH_2N(CH_3)_2$ | $NHCH_3$ |
| | $CF_3$ | |
| | $CH_2NH$-cyclohexyl | |

TABLE 5

| $R^{24}$ | $R^{25}$, $R^{26}$ |
|---|---|
| H | H |
| methyl | methyl |
| ethyl | ethyl |
| n-propyl | n-propyl |
| i-propyl | i-propyl |
| t-butyl | cyclopropylethyl |
| benzyl | cyclopentyl |

TABLE 5-continued

| $R^{24}$ | $R^{25}, R^{26}$ |
|---|---|
| | cyclohexyl |
| | cycloheptyl |
| | vinyl |
| | allyl |
| | prenyl |

TABLE 6

| $R^{27}$ | $R^{28}$ | $R^{29}$ |
|---|---|---|
| H | methyl | methyl |
| methyl | ethyl | ethyl |
| ethyl | n-propyl | n-propyl |
| n-propyl | i-propyl | i-propyl |
| i-propyl | t-butyl | cyclopropylmethyl |
| cyclopropylmethyl | benzyl | cyclopentyl |
| cyclopentyl | | cyclohexyl |
| cyclohexyl | | cycloheptyl |
| cycloheptyl | | vinyl |
| vinyl | | allyl |
| allyl | | prenyl |
| prenyl | | benzyl |
| benzyl | | phenethyl |
| phenethyl | | phenyl |
| phenyl | | 2-furyl |
| 2-furyl | | 3-furyl |
| 3-furyl | | 2-pyridinyl |
| 2-pyridinyl | | 3-pyridinyl |
| 3-pyridinyl | | 4-pyridinyl |
| 4-pyridinyl | | 2-pyrrolyl |
| 2-pyrrolyl | | 3-pyrrolyl |
| 3-pyrrolyl | | 2-thienyl |
| 2-thienyl | | 3-thienyl |
| 3-thienyl | | α-naphthyl |
| | | mono or diCl-phenyl |
| | | CF$_3$-phenyl |
| | | Br-phenyl |
| | | mono or dimethoxy phenyl |
| | | Br-di F-phenyl |
| | | phenyl vinyl |
| | | mono or diF-phenyl |
| | | Cl-thienyl |
| | | isoxyazolylthienyl |

The following cases are more preferable.

$R^2$ is more preferably hydrogen or methyl and particularly preferable is hydrogen.

$R^3$ and $R^5$ are more preferably both hydrogen or taken together may form a bond and particularly preferable is hydrogen.

$R^4$ is preferably —COOR$^{13}$ ($R^{13}$ is hydrogen or lower alkyl), —NR$^{16}$R$^{17}$ ($R^{16}$ and $R^{17}$ is each independently hydrogen, optionally substituted lower alkyl, cycloalkyl, lower alkenyl, optionally substituted aralkyl, optionally substituted amino, or $R^{16}$ and $R^{17}$ taken together may form optionally substituted 5- to 7-membered heterocyclyl with the neighboring nitrogen atom), —NR$^{18}$COR$^{19}$ ($R^{18}$ and $R^{19}$ are each independently hydrogen, optionally substituted lower alkyl or optionally substituted aralkyl), —NR$^{20}$COOR$^{21}$ ($R^{20}$ is hydrogen, or lower alkyl; $R^{21}$ is ester residue), —NR$^{22}$SO$_2$R$^{23}$ ($R^{22}$ is hydrogen; $R^{23}$ is lower alkyl or lower alkylamino), —OH, lower alkoxy. $R^4$ is preferably —COOR$^{13}$ ($R^{13}$ is hydrogen or methyl), —NR$^{16}$R$^{17}$ ($R^{16}$ is hydrogen or lower alkyl, $R^{17}$ is hydrogen, optionally substituted lower alkyl, cycloalkyl, lower alkenyl, optionally substituted aralkyl, optionally substituted amino, or $R^{16}$ and $R^{17}$ taken together may form optionally substituted 5- to 7-membered heterocyclyl with the neighboring nitrogen atom), —NR$^{18}$COR$^{19}$ ($R^{18}$ is hydrogen, $R^{19}$ is hydrogen, optionally substituted lower alkyl or optionally substituted aralkyl), —NR$^{20}$COOR$^{21}$ ($R^{20}$ is hydrogen or methyl; $R^{21}$ is methyl), —NR$^{22}$SO$_2$R$^{23}$ ($R^{22}$ is hydrogen; $R^{23}$ is methyl or methylamino), —OH, lower alkoxy. $R^4$ is preferably —NH$_2$, —NHCH$_3$, or —N(CH$_3$)$_2$.

$R^6$ is more preferably hydrogen, COOMe (Me is methyl), COOEt (Et is ethyl), CN, or CH$_2$NH$_2$, more preferably hydrogen.

$R^7$ is preferably hydrogen, lower alkyl, halogen, phenyl, —COOR$^{34}$ ($R^{34}$ is hydrogen or ester residue), —CHO or —CHNOH, more preferably hydrogen, methyl, ethyl, halogen, or phenyl.

$R^8$ is more preferably hydrogen, optionally substituted lower alkyl, —COR$^{27}$ ($R^{27}$ is hydrogen, lower alkyl, cycloalkyl, lower alkenyl, optionally substituted aralkyl, optionally substituted aryl, or optionally substituted heteroaryl), —COOR$^{28}$ ($R^{28}$ is ester residue), or —SO$_2$R$^{29}$ ($R^{29}$ is lower alkyl, cycloalkyl, optionally substituted lower alkenyl, optionally substituted aralkyl, optionally substituted aryl, optionally substituted heteroaryl), or tri-lower alkyl silyl, more preferably hydrogen or —SO$_2$R$^{29}$ ($R^{29}$ is lower alkyl, cycloalkyl, optionally substituted lower alkenyl, optionally substituted aralkyl, optionally substituted aryl, optionally substituted heteroaryl). $R^{29}$ is more preferably mono- or di-Cl-phenyl, CF$_3$-phenyl, Br-phenyl, mono- or di-methoxyphenyl, phenylvinyl, mono- or di-F-phenyl, Cl-thienyl, naphthyl.

$R^9$ is preferably hydrogen or halogen, more preferably hydrogen.

$R^{10}$ is preferably hydrogen.

$R^{11}$ is preferably hydrogen, halogen, lower alkyl, optionally substituted lower alkenyl, —CN, —SR$^{30}$ ($R^{30}$ is hydrogen or lower alkyl), —CONH$_2$, —CHO, —CHNOH, —NR$^{32}$R$^{33}$ ($R^{32}$ and $R^{33}$ is each independently hydrogen or lower alkyl) or aryl, more preferably hydrogen, halogen, methyl, —CN, or —CONH$_2$.

In a preferred compound among compound (I), $R^1$, $R^2$, $R^3$, $R^5$, $R^6$, $R^9$, and $R^{10}$ are hydrogen; $R^4$ is —NH$_2$, —NHCH$_3$, or —N(CH$_3$)$_2$; $R^7$ is hydrogen, halogen, lower alkyl or phenyl; $R^8$ is hydrogen or —SO$_2$R$^{29}$ ($R^{29}$ is mentioned before); $R^{11}$ is hydrogen, halogen, lower alkyl, —CN, or —CONH$_2$.

A produg of compound (I) is a derivative of compound (I), which has a chemically or metabolically decomposible group and can get back to a pharmaceutically active present invention compound by the solvolysis or under physiological conditions in vivo. Methods of selection and production of a suitable prodrug derivative has been disclosed, for example in Design of Prodrugs, Elsevier, Amsterdam 1985. Having a carboxylic acid group, the original acidic compound can be exemplified to be reacted with an appropriate alcohol derivative to give the ester derivative or reacted with a suitable amino derivative to give the amide derivative as the prodrug. Having a hydroxyl group, the hydroxyl compound for example can be exemplified to be reacted with appropriate acid halides or acid anhydrides to give the acyloxy derivative as the prodrug. Having an amino group, the amino compound can be exemplified to be reacted with a suitable acid halide or acid anhydride to give the amide compound as the prodrug.

A pharmaceutically acceptable salt of compound (I) or the prodrug refers to those salts, which are obtained by reacting with inorganic acids, inorganic bases, ammonia, organic bases, inorganic acids, organic acids, basic amino acids, ionic halogen and the like, or the internal salt. The inorganic base refers to alkaline metals (Na, K and the like), alkalineearth metal (Ca, Mg and the like). Organic base refers to trimethylamine, triethylamine, corrine, procaine, ethanolamine and the like. The inorganic acid refers to hydrochloric acid, hydrogen bromide, sulfuric acid, nitric acid, phosphoric acid, and the like. The organic acid refers to p-toluenesulfonic acid, methanesulfonic acid, formic acid, trifluoroacetic acid, maleic acid and the like. Basic amino acid refers to lysine, arginine, ornithine, histidine and the like.

A solvate of compound (I) refers to the hydrate or alcholate and the like. The racemic or the optically active compound (I) and the like are all included in the present invention.

Compound (I) can be prepared from indole derivatives and the like as starting material which are well known or can be obtained easily by the synthesis. General method of preparation is shown below.

(Method 1 of preparation)

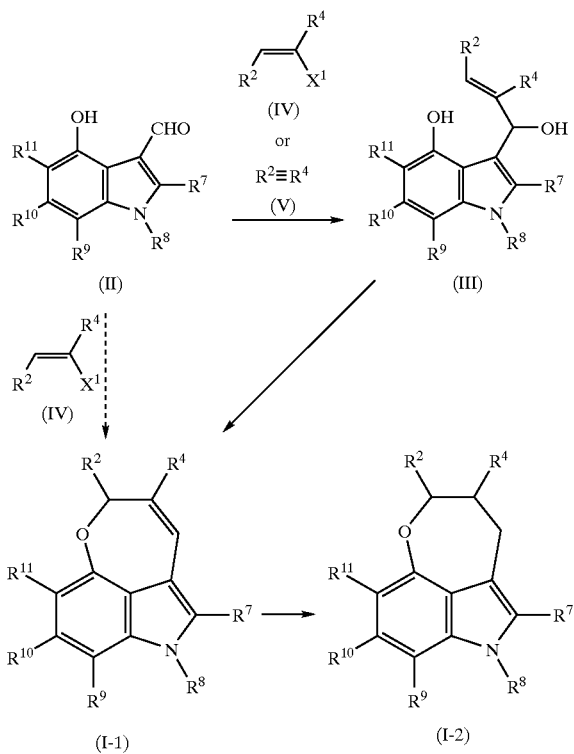

(The 1st Process)

Compound (III) can be obtained by reacting indole derivative (II) with vinyl compound (IV) ($X^1$ is H) in the presence of a base. This reaction can be accomplished fundamentally according to the Baylis-Hillman vinyl alkylation condition. The reaction temperature can be exemplified to be −20–50° C. and the solvent can be illustrated to be tetrahydrofuran (THF), dioxane, dichloromethane, chloroform and the like. Excess vinyl compound can be used as the solvent, also. As the base, 1,4-diazabicyclo [2,2,2]octane (DABCO), tri-n-butylphosphine and the like can be exemplified. The reaction time is ordinarily several hours to several days.

The preparation of compound (III) is also possible by reacting the acetylene compound $R^2C{\equiv}CR^4$ (V) with the vinyl compound (III) ($X^1$ is Al(i-Bu)$_2$), obtained from compound $R^2C{\equiv}CR^4$ (V) and diisopropylaluminumhydride (DIBAL). The reaction to the vinyl aluminum compound can be carried out according to a similar manner of well-known methods (for example: the method is disclosed in *J. Org. Chem.*, 1988, 53, 1037.). The reaction temperature is exemplified to be ordinarily −100 to 50° C. and the solvent is tetrahydrofuran (THF), dioxane, dichloromethane and the like. The reaction temperature is normally several hours to tens of hours.

(The 2nd Process)

Compound (III) is cyclized under a Mitsunobu reaction condition to give compound (I-1) of the present invention. The Mitsunobu reaction can be carried out according to the well-known ordinary method (for example, a method disclosed in *Synthesis*, 1981,1.). The reaction temperature used are exemplified to be −50–50° C. and the solvent used are exemplified to be tetrahydrofuran (THF), dioxane, benzene, toluene, dichloromethane and the like, respectively. Among reagents, 1,1'-(azodicarbonyl)-diethyl ester, 1,1'-(azodicarbonyl)-diisopropyl ester, 1,1'-(azodicarbonyl)-dipieridine and the like are used in this reaction as diazocarboxylic acid ester derivatives. Further, triphenylphosphine, tri-n-butylphosphine and the like can be exemplified as phosphine derivatives. The reaction time is ordinarily several hours to tens of hours.

Furthermore, compound (I-1) can be obtained by cyclizing compound (III) in the presence of base. Moreover, in order to increase the yield of the reaction, it is preferable that the secondary hydrokyl group is first changed to the appropriate removable group such as acetoxyl group and the like and then the cyclization reaction is carried out in the presence of base. The reaction temperature can be exemplified to be 0–100° C. and the solvents can be exemplified to be tetrahydrofuran (THF), dioxane, toluene, acetone, acetonitrile, and the like, respectively. Potassium carbonate, NaH, pyridine, triethylamine and the like can be exemplified as the base used. The reaction time is ordinarily several hours to tens of hours.

Furthermore, it is possible in the 1st process to convert to compound (I-1) through the only one step by reacting compound (II) with compound (IV) ($X^1$ is H) at relatively high temperature (20–50° C.).

Furthermore, it is possible to convert to compound (I-1) through the only one step by reacting compound (II) and compound (IV) ($X^1$ is —PO(OMe)$_2$) under the presence of base. The reaction temperature is ordinarily −20–50° C. Tetrahydrofuran (THF), dioxane, toluene, dichloromethane and the like can be exemplified as the solvent. Potassium tert-butoxyde and the like can be exemplified as the base. The reaction time is ordinarily several hour to tens of hours.

According to the above reaction, preferably a compound, in which $R^4$ in compound (I-1) is electron-withdrawing group, is obtained. As the electron-withdrawing group, ester group, carboxylic acid group, cyano group, amide group, aldehyde group, nitro group and the like are exemplified.

Compound (I-1) is a compound (I) in the present invention, where $R^1$ and $R^6$ are both hydrogen and $R^3$ and $R^5$ taken together may form a bond. Compound (I-1) can be derived to other compounds of the present invention by chemical modifications. For example, compound (I-1), where $R^4$ is carboxylic acid, can be transferred to the various kinds of ester and amide compounds by converting to the acid chloride with thionyl chloride and the like or to the acid anhydride with ethyl chloroacetate and the like under the existence of base such as triethylamine, followed by reacting with the various kinds of alcohol or amino derivatives. Furthermore, compound (I-1) can also be transferred to the various kinds of ester and amide compounds by using appropriate condensing agents such as dicyclohexylxarbodiimide, carbonyldiimidazole and the like. Further, if the reaction is carried out according to Curtius reaction or Hofmann reaction, compound in which $R^4$ is carbamate can be obtained. Moreover, compound in which $R^4$ is hydroxy (or $R^3$ and $R^4$ taken together may form =O) can be prepared by the hydrolysis of the compound in which $R^4$ is carbamate. Furthermore, by reduction catalytically or with sodium borotriacetoxyhydride under the presence of appropriate base, compound, in which $R^3$ and $R^4$ taken together may form =O, can be transferred to compounds in which $R^4$ is various kind of N-alkyl groups.
(The 3rd Process))

Compound (I-2) of the present invention can be obtained by the reduction of compound (I-1). Compound (I-2) is a compound (I) of the present invention, where all of $R^1$, $R^3$, $R^5$ and $R^6$ are hydrogen. The reduction reaction is carried out preferably by a catalytic reduction (Pd/C, $H_2$) thereof. By further chemical modifications of compound (I-2), another compound of the present invention can be obtained. For example, in the case where $R^4$ is primary or secondary amino group, compound (I-2) can be converted to the various kinds of N-sulfonyl or N-acyl compounds by reacting with various kinds of sulfonyl chloride or acyl chloride in the presence of base such as triethylamine and the like. Furthermore, compound (I-2) can be transferred to various kinds of N-alkyl compounds by reacting with various kinds of alkyl halide under the presence of base such as triethylamine and the like or by reduction catalytically or with sodium triacetoxyborohydride in the presence of various kinds of aldehydes or ketones.

(Method 2 of preparation)

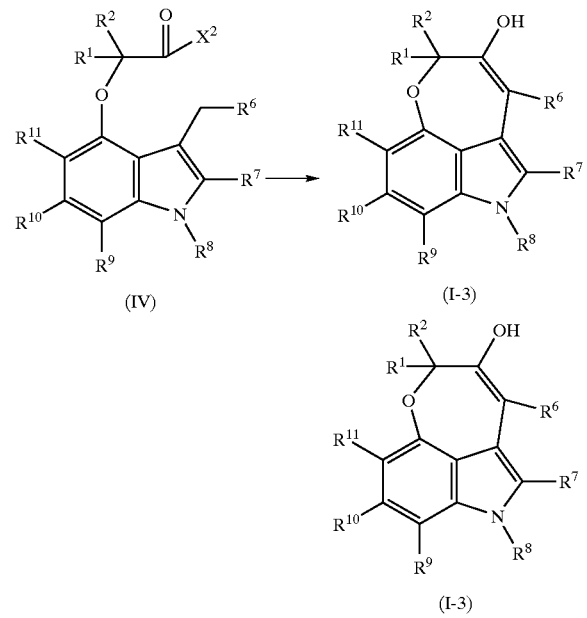

Compound (I-3) of the present invention can be obtained by cyclization of indole derivative (IV) ($X^2$ is a removing group such as lower alkoxy and the like) preferably under the presence of base. Compound (I-3) is a compound in which $R^3$ and $R^5$ taken together may form a bond and $R^4$ is a hydroxy group in compound (I). As the solvent, ether, tetrahydrofuran (THF), dioxane and the like are exemplified. NaH, sodium metal, potassium tert-butoxyde lithium bis (trimethylsilyl)amide and the like are exemplified as the base. The reaction time is ordinarily several hours to tens hours. By this reaction, a preferred compound is obtained, in which $R^6$ is an electron-withdrawing group such as carboxylic acid group, ester group, cyano group.

Moreover, $R^1$ and $R^2$ are preferably hydrogen in the above preparations. Furthermore, if necessary, the group can be protected before the reaction and de-protected after the reaction by the well-known method. For example, $R^8$ in the intermediate is preferably an amino protecting group such as Boc. Compounds obtained by the above method of preparation of the present invention can be transferred to another compound of this invention by further chemical modifications of well-known reaction such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

Having an affinity against various kinds of serotonin receptors, compound (I) has functions as the agonist or antagonist. Therefore, compound (I) is useful as a therapeutic or prophylactic medicine to various serotonin receptor mediated diseases, such as diseases of central nervous systems such as sleep-awakening lesion, circadian rhythm lesion, anxiously mental disorder, schizophrenia, cerebral stroke, dementia, pain, Alzheimer's disease, Parkinson's disease, depression, anxiety, megrim and the like. A specifically preferable compound (I) described above has an affinity against $5HT_{1A}$, $5HT_6$, $5HT_7$ among serotonin receptors and more preferably has a high selective affinity against $5HT_6$. Increase of the selectivity against $5HT_6$ can be achieved preferably by introducing various kinds of substituents to $R^7$ and $R^{11}$ and so on. Then, compound (I) is useful to the selectively $5HT_6$ receptor mediated diseases among the diseases of central nervous system (for example, schizophrenia, Alzheimer's disease, Parkinson's disease, depression, anxiety, migraine and the like).

Compound (I) can be administrated orally or parenterally to mammals including human. Granule, tabula, capsules, injections, suppositorium and the like can be exemplified as an admirable dosage form. In pharmaceutical manufacturing, if necessary, following various additive agents can be used, for example remedium constituens (lactose, mannitol, crystalline cellulose, starch and the like), disintegrators (carmellose, hydroxypropylmethyl cellulose, polyvinylpolypyrrolidone and the like), binding agent (methylcellose, hydroxypropylcellose, cellose, poloyvinylalcohol and the like), lubricant (Magnesium stearate, talc and the like), stabilizing agent, coloring agent, coating material. Dosage varies depending on the examinee's age, body weight, condition of diseases and dosage forms and so on. Generally, dosage is ca. 0.001 mg to 1 g/day to an adult in oral or parenteral administration. Number of administration time is one to several times/day.

Examples of this invention are described below without limiting the present invention thereto. "Ex" in the Scheme of reaction corresponds to the number of Example, e.g. "Ex 1" means compound (1) obtained by the procedure cited in Example 1.

(Abbreviated Words)

Me=methyl; Et=ethyl; tBu=t-butyl; nPr=n-propyl; Ph=phenyl; Ts=p-toluene sulfonyl; Bn=benzyl; Ms=methanesulfonyl

EXAMPLE 1 OF REFERENCE

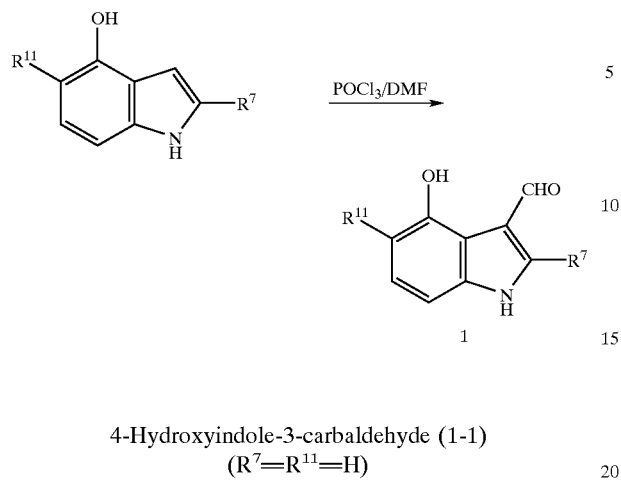

4-Hydroxyindole-3-carbaldehyde (1-1) ($R^7=R^{11}=H$)

Phosphorous oxychloride 7.35 ml was added dropwise to dry dimethylformamide 15 ml under cooling in ice-methanol bath and the mixture was stirred for 15 min. Then, a solution of the 4-hydroxyindole 5.0 g in dry dimethylformamide 10 ml was added dropwise to the mixture under cooling in ice and the mixture was stirred for 2 h at room temperature. Water was added under cooling in ice to the mixture, which was made alkaline with a 30% aqueous sodium hydroxide solution and was stirred for 15 min. Then, the mixture was acidified to pH 4 with 5N-HCl and the precipitate was collected by filtration, washed with water and dried to give the titled compound 4.99 g as crude crystalline materials. Yield 82%. Crude crystalline materials are recrystallized from methanol to give yellow crystals m.p. 190–193° C.

$^1$H-NMR(DMSO-$d_6$): 6.54 (1H, dd, J=8.1, 0.9 Hz), 6.95 (1H, dd, J=8.1, 0.9 Hz), 7.13 (1H, t, J=8.1 Hz), 8.37 (1H, s), 9.64 (1H, s), 10.54 (1H, br s), 12.35 (1H, br s).

Following compounds were obtained, according to the similar treatment.

| Compd No | $R^7$ | $R^{11}$ | m.p. (° C.) | $^1$H-NMR (DMSO-$d_6$) |
|---|---|---|---|---|
| 1-2 | Ph | H | 239–247 (dec.) | 6.57 (1H, dd, J=8.1, 0.9 Hz), 6.95 (1H, dd, J=8.1, 0.9 Hz), 7.17 (1H, t, J=8.1 Hz), 7.61–7.82 (5H, m), 9.56 (1H, s), 11.05 (1H, s), 12.67 (1H, br s) |
| 1-3 | Me | Me | 269–272 (dec.) | 2.16 (3H, s), 2.66 (3H, s), 6.72 (1H, d, J=8.1 Hz), 6.93 (1H, d, J=8.1 Hz), 9.64 (1H, br s), 11.05 (1H, s), 12.14 (1H, br s) |

EXAMPLE 2 OF REFERENCE

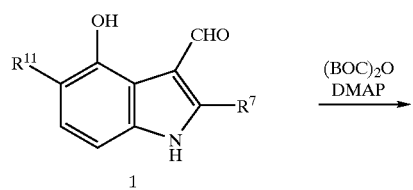

3-Formyl-4-hydroxyindole-1-carboxylic acid tert-butyl ester (2-1) ($R^7=R^{11}=H$)

A mixture of the 3-formyl-4-hydroxyindole (1-1) 323 mg, di-tert-butyldicarbonate 458 mg, dimethylaminopyridine 12.5 mg and acetonitrile 25 ml was stirred under cooling in ice for 3 h. The solvent was removed under reduced pressure and the residue obtained was recrystallized from acetone-isopropyl ether to give the titled compound as pale yellow crystals, m.p. 159–161° C.(dec.), 389 mg. Yield 74%.

$^1$H-NMR(CDCl$_3$): 1.71 (9H, s), 6.84 (1H, dd, J=8.1, 0.9 Hz), 7.31 (1H, t, J=8.1 Hz), 7.61 (1H, dd, J=8.1, 0.9 Hz), 8.25 (1H, s), 9.76 (1H, d, J=0.6 Hz), 10.13 (1H, s).

Following compounds were obtained, according to the similar treatment.

| Compd No | $R^7$ | $R^{11}$ | m.p. (° C.) | $^1$H-NMR (CDCl$_3$) |
|---|---|---|---|---|
| 2-2 | Ph | H | 154–155 (dec.) | 1.26 (9H, s), 6.86 (1H, dd, J=8.4, 0.9 Hz), 7.33 (1H, t, J=8.4 Hz), 7.43–7.53 (5H, m), 7.66 (1H, dd, J=8.4, 0.9 Hz), 9.36 (1H, s), 10.64 (1H, s) |
| 2-3 | Me | Me | 177–179 (dec.) | 1.71 (9H, s), 2.30 (3H, s), 2.88 (3H, s), 7.09 (1H, d, J=8.4 Hz), 7.39 (1H, d, J=8.4 Hz), 9.90 (1H, br s), 10.92 (1H, s) |

EXAMPLE 3 OF REFERENCE

5-Bromo-3-formyl-4-hydroxyindole-1-carboxylic acid tert-butyl ester (2-4)

Compound (2-1) 26.1 g was suspended in dry tetrahydrofuran 260 ml and chloroform 260 ml. Pyridinium bromide perbromide 33.6 g was added to the suspension under cooling in ice and the mixture was stirred at room temperature for 4.5 h. An aqueous sodium hydrogen carbonate 16.77 g solution was added to the reaction mixtures, which were extracted with chloroform. The extracts were washed with water, dried over anhydrous magnesium sulfate, concentrated up to the deposition of crystals and diluted with isopropanol. Appeared crystals were collected by filtration to give the titled compound as yellow crystals. 29.1 g. Yield 86%. m.p. 239–242° C.(dec.)

$^1$H-NMR(CDCl$_3$): 1.71 (9H, s), 7.52 (2H, s), 8.24 (1H, s), 9.75 (1H, s), 10.91 (1H, br s).

Scheme of Reactions, Examples 1–5

Example 1

7H-6-Oxa-2-azabenzo[c,d]azulene-2,8-dicarboxylic acid 2-tert-butyl ester 8-methyl ester (3-1)
($R^7=R^{11}=H$)

(Method 1)

60% Sodium hydride 23.0 mg was suspended in dry tetrahydrofuran 4 ml. Compound (2-1) 123 mg and trimethyl-2-phosphonoacrylate 116 μl were added with cooling in ice under nitrogen atmosphere and the mixture was stirred for 19 h. Water was added to the mixture with cooling in ice and the mixture was extracted with ethyl acetate. The extracts were washed with water, dried over anhydrous

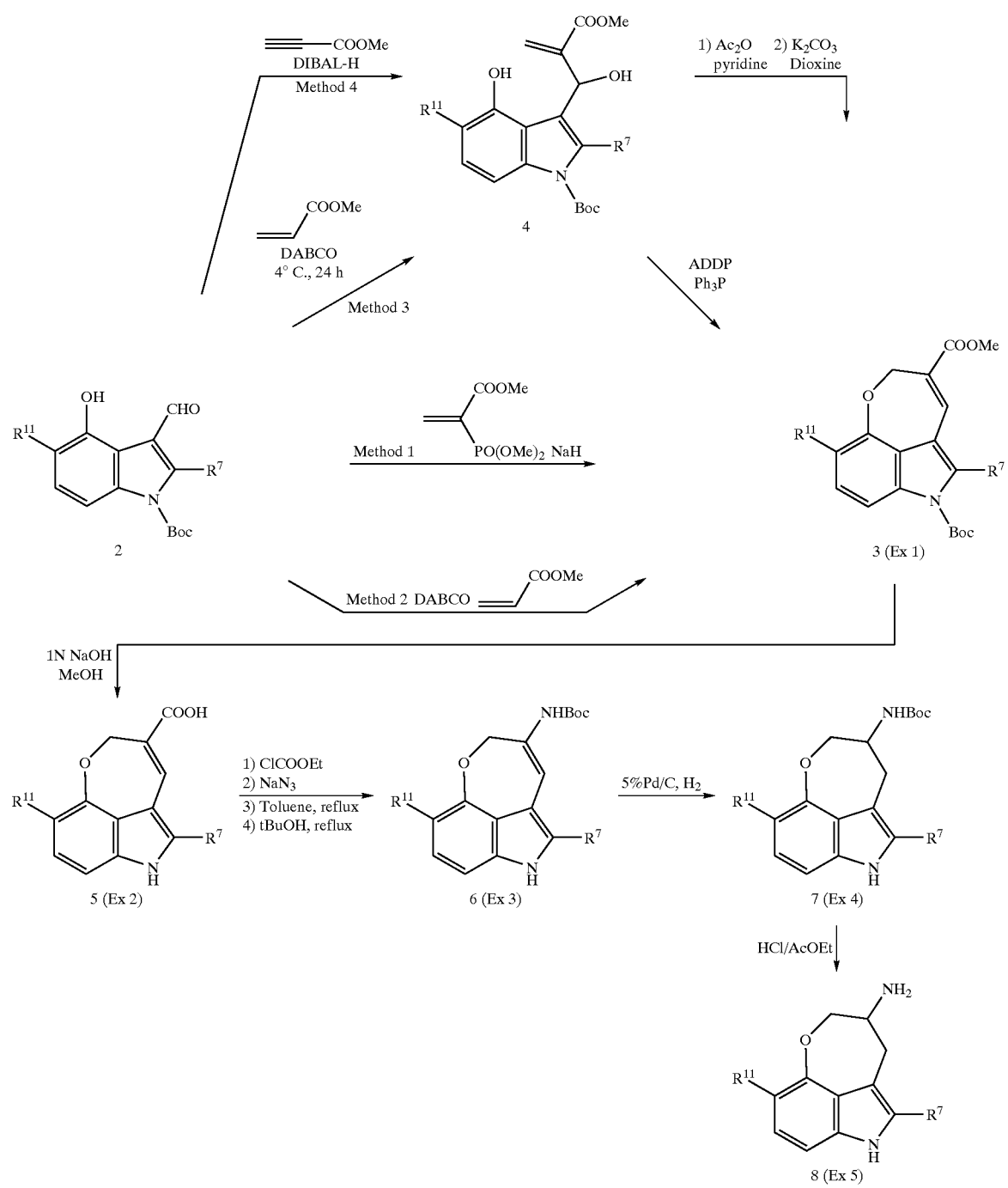

magnesium sulfate and chromatographed on silica gel 25 g in ethyl acetate:hexane (1:10) to give the titled compound (3-1) as colorless crystals, 46 mg. Yield 30%.

$^1$H-NMR(CDCl$_3$): 1.69 (9H, s), 3.84 (3H, s), 5.06 (2H, s), 6.85 (1H, dd, J=7.5, 0.6 Hz), 7.24 (1H, t, J=7.5 Hz), 7.74 (1H, s), 7.77 (1H, d, J=7.5 Hz), 8.00 (1H, s).

(Method 2)

Compound (2-1) 140 mg, 1,4-diazabicyclo[2.2.2]octane 70 mg was suspended in methyl acrylate 1.4 ml and the suspension was stirred at room temperature for 4 days. Ethyl acetate was added to the reaction mixtures and the insoluble materials were filtered off. The filtrate was concentrated under reduced pressure and chromatographed on silica gel 25 g in ethyl acetate:hexane (1:10) to give titled compound (3-1) as colorless crystals 59 mg. Yield 34%.

(Method 3)

(a) 4-Hydroxy-3-(1-hydroxy-2-methoxycarbonylallyl)indole-1-carboxylic acid tert-butyl ester (4-1) ($R^7=R^{11}=H$)

Compound (2-1) 140 mg and 1,4-diazabicyclo[2.2.2]octane 70 mg were suspended in methyl acrylate 1.4 ml with cooling in ice and the suspension was stirred at 4° C. for 24 h. The reaction mixtures was chromatographed on silica gel in ethyl acetate:hexane several times to give the titled compound (4-1) as a colorless oil 178 mg. Yield 96%.

$^1$H-NMR (CDCl$_3$): 1.66 (9H, s), 3.86 (3H, s), 5.05 (1H, br s), 5.63 (1H, s), 5.81 (1H, s), 6.39 (1H, s), 6.78 (1H, dd, J=8.1, 0.9 Hz), 7.24 (1H, t, J=8.1 Hz), 7.31 (1H, s), 7.67 (1H, d, J=8.1 Hz), 9.10 (1H, br s).

Following compounds were obtained, according to the similar treatment.

| Compd No | $R^7$ | $R^{11}$ | m.p. (° C.) | $^1$H-NMR (CDCl$_3$) |
|---|---|---|---|---|
| 4-2 | Ph | H | 121–122 | 1.21 (9H, s), 3.82 (3H, s), 5.01 (1H, br s), 5.51 (2H, s), 6.35 (1H, s), 6.81 (1H, dd, J=7.8, 0.6 Hz), 7.28 (1H, t, J=8.4 Hz), 7.38–7.40 (5H, m), 7.83 (1H, dd, J=8.4, 0.6 Hz), 9.14 (1H, s) |
| 4-3 | Me | Me | 155–156.5 | 1.68 (9H, s), 2.29 (3H, s), 2.48 (3H, s), 3.87 (3H, s), 5.14 (1H, br s), 5.37 (1H, s), 5.96 (1H, s), 6.30 (1H, s), 7.05 (1H, d, J=8.4 Hz), 7.56 (1H, d, J=8.4 Hz), 9.27 (1H, s) |
| 4-4 | H | Br | Colorless oil | 1.66 (9H, s), 3.85 (3H, s), 5.13 (1H, d, J=5.4 Hz), 5.62 (1H, s), 5.82 (1H, d, J=5.4 Hz), 6.39 (1H, s), 7.32 (1H, s), 7.44 (1H, d, J=8.7 Hz), 7.57 (1H, d, J=8.7 Hz), 9.59 (1H, br s) |

(b) 7H-6-Oxa-2-azabenzo[c,d]azulene-2,8-dicarboxylic acid 2-tert-butyl ester 8-methyl ester (3-1)

Triethylamine 20.1 mg, 1,1'-(azodicarbonyl)-dipiperidine 42.0 mg and triphenylphosphine 43.9 mg were dissolved in dry tetrahydrofuran 1 ml. Compound (4-1) 37 mg was added to the solution with cooling in ice under nitrogen. The mixture was stirred at room temperature for 17 h. Water was added with cooling in ice and the reaction mixture was extracted with ethyl acetate. The extracts were washed with water, dried over anhydrous magnesium sulfate and chromatographed on silica gel 15 g in ethyl acetate:hexane (1:3) to give titled compound (3-1) as colorless crystals, 17. mg. Yield 48%.

(c) 7H-6-Oxa-2-azabenzo[c,d]azulene-2,8-dicarboxylic acid 2-tert-butyl ester 8-methyl ester (3-1) ($R^7=R^{11}=H$)

Acetic anhydride 0.38 ml was added to a solution of compound (4-1) 1.32 g in pyridine 13.1 ml with cooling in ice under nitrogen. The mixture was stirred at that temperature for 1 h The solvent was removed by distillation under reduced pressure and the residue obtained was chromatographed on silica gel 60 g in ethyl acetate:hexane (1:3) to give a yellow oil 860 mg. The oily compound 747 mg was dissolved in dioxane 7 ml and potassium carbonate 530.5 mg was added. The mixture was stirred at 80° C. for 6 h, filtered through cerite and chromatographed on silica gel 40 g in ethyl acetate:hexane (1:10) to give the titled compound (3-1) as colorless crystals, 501 mg. Yield 40%, m.p. 124–126° C. (recrystallized from isopropanol)

Following compounds were obtained, according to the similar treatment.

| Compd No | $R^7$ | $R^{11}$ | m.p. (° C.) | $^1$H-NMR (CDCl$_3$) |
|---|---|---|---|---|
| 3-2 | Ph | H | 151–152 | 1.26 (9H, s), 3.75 (3H, s), 5.08 (2H, s), 6.87 (1H, dd, J=8.1, 0.9 Hz), 7.27 (1H, t, J=8.1 Hz), 7.35–7.49 (5H, m), 7.65 (1H, s), 7.87 (1H, dd, J=8.1, 0.9 Hz) |
| 3-3 | Me | Me | 112–114 | 1.69 (9H, s), 2.31 (3H, s), 2.70 (3H, s), 3.84 (3H, s), 5.03 (2H, s), 7.04 (1H, d, J=8.4 Hz), 7.61 (1H, d, J=8.4 Hz), 8.07 (1H, s) |
| 3-4 | H | Br | 160–161 | 1.68 (9H, s), 3.84 (3H, s), 5.14 (2H, s), 7.46 (1H, d, J=9.0 Hz), 7.68 (1H, d, J=9.0 Hz), 7.74 (1H, s), 7.99 (1H, s) |

(Method 4)

4-Hydroxy-3-(1-hydroxy-2-methoxycarbonylallyl)-2,5-dimethylindole-1-carboxylic acid tert-butyl ester (4-3) ($R^7=R^{11}=H$)

Diisobutylaluminumhydride (0.9 mol/l hexane solution) 50 ml was added to a mixture of hexamethylphosphorous triamide (8.96) g and dry tetrahydrofuran 80 ml with cooling in ice under a nitrogen atmosphere. The mixture was stirred for 30 min. Methyl propiorate 3.78 g was added and he mixture was stirred for 1 h with cooling in ice. Compound (2-3) 4.36 g was added to the reaction mixture, which was stirred for 10 min and then at room temperature for 2 h. 1N—HCl 50 ml was added with cooling in ice and the mixture was extracted with ethyl acetate. The extracts were washed with 1N—HCl, water, brine and dried over anhydrous magnesium sulfate and concentrated under reduced pressure. The residue obtained was chromatographed on silica gel 130 g in ethyl acetate:hexane (1:4) to give colorless crystals which were recrystallized from ethyl acetate-hexane to give the titled compound, 4.47 g. Yield 80%, m.p. 155–156.5° C.

Example 2

2,7-Dihydro-6-oxa-2-azabenzo[c,d]azulene-8-carboxylic acid (5-1) ($R^7=R^{11}=H$)

The above obtained compound (3-1) 1.01 g was dissolved in tetrahydrofuran 15 ml and 1 N sodium hydroxide 15 ml was added to the solution. The mixture was stirred for 1 h. Methanol 7.5 ml was added. The mixture was stirred at 50° C. for 3 h, acidified with 2N—HCl 7.5 ml to weakly acidic with cooling in ice and extracted with ether. The extracts were washed with brine, dried over anhydrous magnesium sulfate and concentrated under reduced pressure to give a yellow solid, which was recrystallized from methanol to give the titled compound (5-1), m.p. 230° C.(dec.) as yellow crystals, 450 mg. From the mother liquor, the second crop 134 mg was obtained by crystallization from isopropanol. Yield 88%.

$^1$H-NMR (CD$_3$OD): 4.98 (2H, s), 6.60 (1H, m), 7.02–7.08 (2H, m), 7.55 (1H, s), 8.19 (1H, s).

Following compounds were obtained, according to the similar treatment.

| Compd No | R$^7$ | R$^{11}$ | m.p. (° C.) | $^1$H-NMR (DMSO-d$_6$) |
|---|---|---|---|---|
| 5-2 | Ph | H | 218–220 (dec.) | 4.98 (2H, s), 6.59–6.60 (1H, m), 7.06–7.13 (2H, m), 7.51–7.68 (5H, m), 8.05 (1H, s), 12.27 (1H, br s) |
| 5-3 | Me | ME | 203–206 (dec.) | 2.20 (3H, s), 2.48 (3H, s), 4.87 (2H, s), 6.84–6.89 (2H), 8.03 (1H, s), 11.69 (1H, s), 12.03 (1H, br s) |
| 5-4 | H | Br | 210–215 (dec.) | 4.97 (2H, s), 7.07 (1H, d, J=8.4 Hz), 7.27 (1H, d, J=8.7 Hz), 7.83 (1H, s), 8.09 (1H, s), 12.07 (1H, s) |

Example 3

(2,7-Dihydro-6-oxa-2-azabenzo[c,d]azulen-8-yl) carbamic acid tert-butyl ester (6-1) (R$^7$=H)

Triethylamine 0.38 ml and chloroethyl carbonate 0.26 ml were added to a solution of the compound obtained by Ex. 2 (5-1) 530 mg in dry tetrahydrofuran 5 ml with cooling in ice-methanol bath and the mixture was stirred for 30 min. Then an aqueous solution of sodium azide 320 mg/water 2 ml was added dropwise and the mixture was stirred for 4 h with cooling in ice-methanol bath. Water was added and the reaction mixture was extracted with ethyl acetate. The extracts were washed with brine and dried over anhydrous magnesium sulfate and concentrated under reduced pressure to give a yellow solid. The residue obtained was suspended in toluene 20 ml and heated under reflux at 125° C. for 20 min and concentrated under reduced pressure. The residue obtained was again suspended in t-butanol 20 ml, heated at 100° C. for 2.5 h and concentrated under reduced pressure. The residue obtained was chromatographed on silica gel 50 g in ethyl acetate:hexane (1:3) to give brown crystals, which was recrystallized from ether-petrolether to give the titled compound (6-1) m.p. 125–130° C. (dec.) as pale brown crystals, 436 mg. Yield 62%.

$^1$H-NMR (CDCl$_3$): 1.50 (9H, s), 4.76 (2H, s), 6.01 (1H, br s), 6.64 (1H, dd, J=7.2, 1.2 Hz), 6.98–7.12 (3H, m), 8.17 (1H, br s).

Following compounds were obtained, according to the similar treatment.

| Compd No | R$^7$ | m.p. (° C.) | $^1$H-NMR (CDCl$_3$) |
|---|---|---|---|
| 6-2 | Ph | 201–202 (dec.) | 1.49 (9H, s), 4.90 (2H, br s), 6.11 (1H, br s), 6.67 (1H, m), 6.88–7.41 (5H, m), 7.49 (1H, m), 7.59 (1H, d, J=8.4 Hz), 8.24 (1H, br s) |

Example 4

(2,7,8,9-Tetrahydro-6-oxa-2-azabenzo[c,d]azulen-8-yl)carbamic acid tert-butyl ester (7-1) (R$^7$=H)

5% Pd/C 100 mg was added to a solution of the compound obtained in Ex. 3 460 mg in methanol 10 ml. The mixture was stirred in a hydrogen atmosphere for 1.5 h. The catalyst was filtered off and the filtrate was concentrated under reduced pressure. The residue obtained was chromatographed on silica gel in ethyl acetate:hexane (1:3) to give the titled compound (7-1) as a reddish oil, 390 mg. Yield 84%.

$^1$H-NMR (CDCl$_3$): 1.41 (9H, s), 2.98–3.10 (1H, m), 3.26–3.38 (1H, m), 4.23 (1H, d, J=12.0 Hz), 4.27–4.40 (1H, m), 4.48–4.58 (1H, m), 6.67 (1H, dd, J=7.2, 0.9 Hz), 6.98 (1H, br s), 7.02 (1H, dd, J=7.2, 0.9 Hz), 7.09 (1H, t, J=7.2 Hz), 8.13 (1H, br s).

Following compounds were obtained, according to the similar treatment.

| Compd No | R$^7$ | m.p. (° C.) | $^1$H-NMR (CDCl$_3$) |
|---|---|---|---|
| 7-2 | Ph | 188–189 | 1.38 (9H, s), 3.18 (1H, m), 3.43 (1H, m), 4.29 (1H, d, J=12.0 Hz), 4.39 (1H, m), 4.56 (1H, m), 5.08 (1H, br s), 6.70 (1H, m), 7.04 (1H, m), 7.11 (1H, t, J=7.8 Hz), 7.34–7.55 (5H, m), 8.28 (1H, br s) |

Example 5

2,7,8,9-Tetrahydro-6-oxa-2-azabenzo[c,d]azulen-8-ylamine (8-1)

The compound obtained in Ex 4 (7-1) 262 mg was dissolved in ethyl acetate 3 ml. A solution of 4 N HCl/ethyl acetate 2 ml was added to the solution with cooling in ice and the mixture was stirred at room temperature for 3 h. Furthermore, 4N-HCl/ethyl acetate 1 ml was added and the mixture was stirred at room temperature for 1 h. After the volatile materials were remove by distillation under reduced pressure up to the half volume, the mixture was diluted with ethyl acetate 10 ml. An aqueous saturated sodium hydrogen solution carbonate was added to alkaline with cooling in ice. The mixture was extracted with ethyl acetate. The extracts were washed with brine, dried over anhydrous magnesium sulfate and concentrated under reduced pressure to give a brown oily residue, which was chromatographed on aluminum oxide 40 g in methanol:chloroform (3:97) to give the titled compound (8-1) as brown crystals, 144 mg. Yield 84%.

Further, this oil was recrystallized from isopropanol to give the titled compound (8-1) as gray crystals, 60 mg. m.p. 172–173° C.

$^1$H-NMR (CD$_3$OD): 2.84–2.93 (1H, ddd, J=15.6, 8.7, 1.5 Hz), 3.17–3.25 (1H, m), 3.36–3.43 (1H, m), 4.12–4.25 (2H, m), 6.43–6.50 (1H, m), 6.89–7.00 (3H, m).

Following compounds were obtained, according to the similar treatment.

| Compd No | R$^7$ | m.p. (° C.) | $^1$H-NMR (CDCl$_3$) |
|---|---|---|---|
| 8-2 | Ph | 189–191 | 3.09 (1H, dd, J=15.6, 8.1 Hz), 3.29 (1H, dd, J=15.6, 3.6 Hz), 3.59 (1H, m), 4.27–4.36 (2H, m), 6.67 (1H, m), 7.01 (1H, m), 7.10 (1H, t, J=8.1 Hz), 7.34–7.59 (5H, m), 8.25 (1H, br s) |

Scheme of Reactions, Examples 6–10 are shown in below

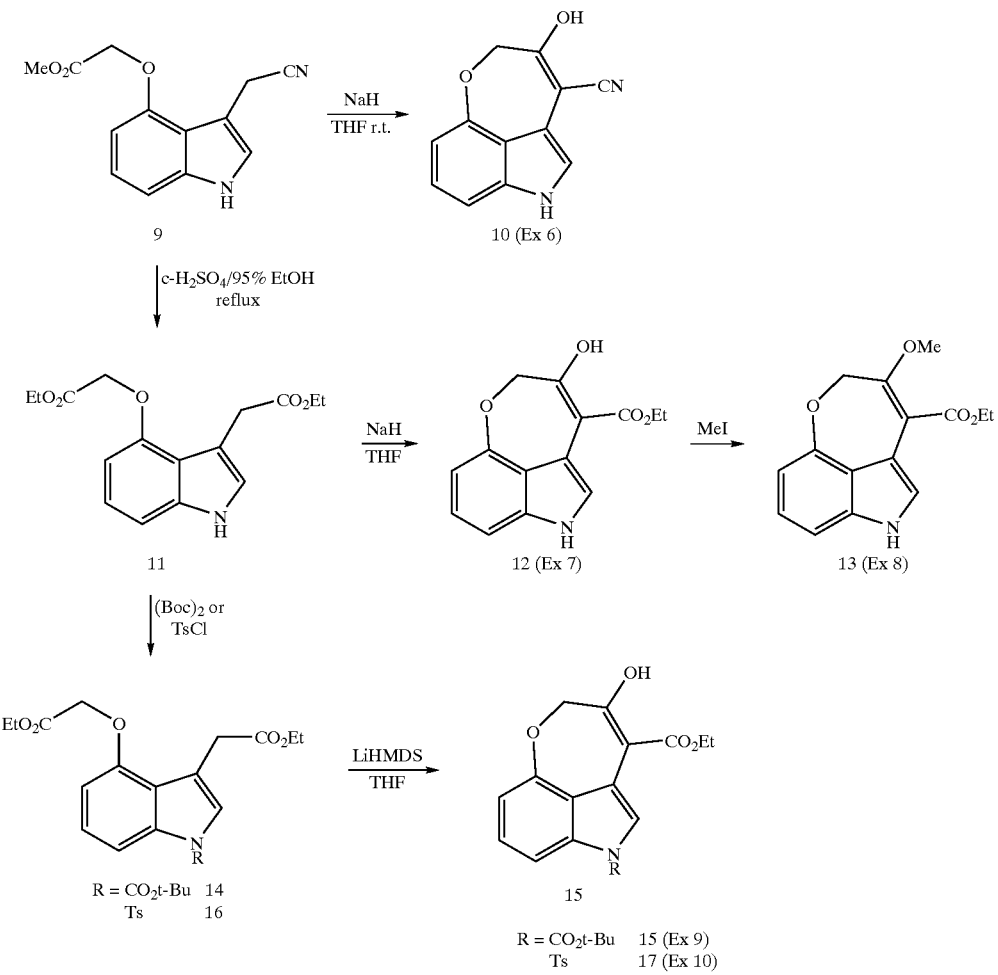

Example 6

8-Hydroxy-2,7-dihydro-6-oxa-2-azabenzo[c,d]
azulene-9-carbonitrile (10)

Compound (9) 200 mg was dissolved in dry tetrahydrofuran 10 ml. 60% Sodium hydride 72 mg was added to the solution with cooling in ice and the mixture was stirred at room temperature for 2.5 h. After excess sodium hydride was decomposed with ethanol with cooling in ice, 2 N—HCl 1.5 ml was added. The mixture was extracted with ether. The extracts were washed with brine, dried over anhydrous magnesium sulfate and concentrated under reduced pressure. The residue obtained was chromatographed on silica gel 4 g in ether to give an eluent 187 mg which was again chromatographed on silica gel 5 g in ether to give the titled compound (10) as reddish orange crystals, 132 mg. Yield 79.5%.

$^1$H-NMR (CDCl$_3$): 4.80 (2H, s), 6.52 (1H, dd, J=7.5, 0.9 Hz), 6.99 (1H, t, J=7.5 Hz), 7.06 (1H, dd, J=7.5, 0.9 Hz), 7.24 (1H, d, J=2.7 Hz), 11.07 (1H, s), 11.39 (1H, s).

Example 7

(1) 3-Ethoxycarbonylmethyl-1H-indol-4-yloxy)
acetic acid ethyl ester (11)

Compound (9) 1.49 g was dissolved in 95% ethanol 45 ml. Concentrated sulfuric acid 4.5 ml was added to the solution. The mixture was heated under reflux for 40 h. After the solvent was removed under reduced pressure, ice-water was added to the mixture, which was extracted with chloroform. The extracts were washed with water dried over anhydrous magnesium sulfate and chromatographed on silica gel 37 g in chloroform. The eluent 1.497 g was recrystallized from acetone-isopropyl ether to give the titled compound (11) as pale gray crystals, 1.304 g, m.p. 90–91.5° C. Yield 70.1%.

$^1$H-NMR (CDCl$_3$): 1.26 (3H, t, J=7.2 Hz), 1.31 (3H, t, J=7.2 Hz), 4.05 (2H, s), 4.18 (2H, q, J=7.2 Hz), 4.28 (2H, q, J=7.2 Hz), 4.69 (2H, s), 6.36 (1H, dd, J=7.2, 0.9 Hz), 6.97–7.07 (3H, m), 8.07(1H, br s).

(2) 8-Hydroxy-2,7-dihydro-6-oxa-2-azabenzo[c,d]
azulene-9-carboxylic acid ethyl-ester (12)

Compound (11) 754 mg was dissolved in dry tetrahydrofuran 20 ml. 60% Sodium hydride 217 mg was added to the solution of with cooling in ice. The mixture was stirred at room temperature for 1 h. To the ice-cold reaction mixture, ethanol 0.5 ml was added and the 2N HCl 3 ml was added to acidify. The mixture was extracted with ether. The extracts were washed with brine, dried over anhydrous magnesium sulfate and concentrated under reduced pressure. The residue obtained was chromatographed on silica gel 45 g in chloroform. The eluent 198 mg was recrystallized from ether-isopropyl ether to give the titled compound (12) as colorless crystals 195 mg, m.p. 136–137° C. Yield 30.5%.

$^1$H-NMR (CDCl$_3$): 1.44 (3H, t, J=7.2 Hz), 4.42 (2H, q, J=7.2 Hz), 4.75 (2H, s), 6.56–6.71 (1H, m), 7.02–7.09 (2H, m), 7.50 (1H, d, J=2.7 Hz), 8.20 (1H, br s), 13.02 (1H, s).

Example 8

8-Methoxyl-2,7-dihydro-6-oxa-2-azabenzo[c,d]azulene-9-carboxylic acid ethyl ester (13)

A mixture of the compound obtained in Ex. 7 (12) 100 mg, methyl iodide 0.031 ml and potassium carbonate 9 mg in dimethylformamide 3 ml was stirred at room temperature for 15 h. Water was added and the mixture was extracted with ether. The extracts were washed with brine, dried over anhydrous magnesium sulfate and concentrated under reduced pressure. The residue obtained was chromatographed on silica gel 6 g in chloroform. The eluent 102 mg was recrystallized from acetone-ether to give the titled compound (13) as colorless crystals 67 mg, m.p. 183–184° C. Yield 63.8%.

$^1$H-NMR (CDCl$_3$): 1.24–1.29 (3H, m), 1.82 (3H, s), 4.16–4.35 (2H, m), 4.49 (1H, d, J=17.4 Hz), 5.02 (1H, d, J=17.4 Hz), 6.73–6.79 (1H, m), 6.96–6.97(1H, m), 7.02–7.13 (2H, m), 8.35 (1H, br s).

Example 9

(1) 4-Ethoxycarbonylmethoxy-3-ethoxycarbonylmethyl-indole-1-carboxylic acid tert-butyl ester (14)

Compound (11) 1.40 g and di-tert-butyldicarbonate 1.05 g were dissolved in tetrahydrofuran 20 ml and 4-dimethylaminopyridine 28 mg was added. The mixture was allowed to stand at room temperature overnight and concentrated under reduced pressure to remove tetrahydrofurane. The residue obtained was dissolved in toluene and chromatographed on silica gel 10 g in 5% ethyl acetate-toluene to give the titled compound (14) as a colorless oil, 1.789 g. Yield 96.2%.

$^1$H-NMR (CDCl$_3$): 1.26 (3H, t, J=7.2 Hz), 1.30 (3H, t, J=7.2 Hz), 1.65 (9H, s), 3.96 (2H, s), 4.18 (2H, q, J=7.2 Hz), 4.27 (2H, q, J=7.2 Hz), 4.67 (2H, s), 6.52 (1H, d, J=8.1 Hz), 7.18 (1H, t, J=8.1 Hz), 7.42 (1H, s), 7.80 (1H, d, J=8.1 Hz).

(2) 8-Hydroxy-7H-6-oxa-2-azabenzo[c,d]azulene-2,9-dicarboxlic acid 2-tert-butyl ester 9-ethyl ester (15)

Compound (14) 953 mg was dissolved in dry tetrahydrofuran 15 ml and 1.0 M solution of lithium bistrimethylsilylamide-tetrahydrofuran 3.5 ml was added to the solution with cooling in ice. The mixture was stirred at room temperature for 30 min. A solution of ammonium chloride 375 mg in water 5 ml was added with cooling in ice. The mixture was extracted with ether. The extracts were washed with brine, dried over anhydrous magnesium sulfate and concentrated under reduced pressure. The residue obtained was chromatographed on silica gel 30 g in chloroform. The eluent 259 mg was recrystallized from ether-isopropyl ether to give the titled compound (15) as colorless crystals, m.p.139.5–140.5° C., 236 mg. Yield 28.0%.

$^1$H-NMR (CDCl$_3$): 1.47 (3H, t, J=7.1 Hz), 1.68 (9H, s), 4.43 (2H, q, J=7.1 Hz), 4.73 (2H, s), 6.80 (1H, d, J=8.1 Hz), 7.18 (1H, t, J=8.1 Hz), 7.83 (1H, d, J=8.1 Hz), 7.87 (1H, s), 13.27 (1H, s).

Example 10

(1) [3-Ethoxycarbonylmethyl-1-(toluene-4-sulfonyl)-1H-indol-4-yloxy]acetic acid ethyl ester (16)

Compound (11) 305 mg was dissolved in dry tetrahydrofuran 20 ml. 1.0 M Solution of lithium bistrimethylsilylamide-tetrahydrofuran 1.1 ml was added to the solution with cooling in dry ice-acetone bath at −70° C. After the mixture was stirred for 10 min, a solution of p-toluenesulfonyl chloride 229 mg in tetrahydrofuran 3 ml was added at that temperature. The mixture was stirred at room temperature for 2 h. A solution of ammonium chloride 59 mg in water 1 ml was added to the mixture, which was concentrated under reduced pressure to remove tetrahydrofuran. Water was added. The mixture was extracted with chloroform. The extracts were washed with water dried over anhydrous magnesium sulfate and concentrated under reduced pressure. The residue obtained was chromatographed on silica gel 17 g in chloroform to give the titled compound (16) as a colorless oil 231 mg. Yield 50.2%.

$^1$H-NMR (CDCl$_3$): 1.24 (3H, t, J=7.2 Hz), 1.28 (3H, t, J=7.2 Hz), 2.34 (3H, s), 3.94 (2H, s), 4.16 (2H, q, J=7.2 Hz), 4.25 (2H, q, J=7.2 Hz), 4.62 (2H, s), 6.49 (1H, d, J=8.1 Hz), 7.17 (1H, t, J=8.1 Hz), 7.21 (2H, d, J=8.7 Hz), 7.44 (2H, d, J=8.7 Hz), 7.60 (1H, d, J=8.1 Hz), 7.74 (2H, d, J=8.7 Hz).

(2) 8-Hydroxy-2-(toluene-4-sulfonyl)-2,7-dihydro-6-oxa-2-azabenzo[c,d]-azulene-9-carboxlic acid ethyl ester (17)

Compound (16) 228 mg was dissolved in dry tetrahydrofuran 10 ml and 1.0 M solution of lithium bistrimethylsilylamide tetrahydrofuran 1.05 ml was added to the solution with cooling in ice. The mixture was stirred for 20 min. A solution of ammonium chloride 112 mg in water 1 ml was added to the mixture, which was acidified with dilute hydrochloric acid. The mixture was extracted with ether. The extracts were washed with brine, dried over anhydrous magnesium sulfate and concentrated under reduced pressure. The residue obtained 279 mg was chromatographed on silica gel 10 g in toluene to give the titled compound (17) as a pale yellow oil 61 mg. Yield 29.8%.

$^1$H-NMR (CDCl$_3$): 1.50 (3H, t, J=7.2 Hz), 2.35 (3H, s), 4.45 (2H, q, J=7.2 Hz), 4.68 (2H, s), 6.78 (1H, dd, J=7.8, 0.9 Hz), 7.17 (1H, t, J=7.8 Hz), 7.23 (2H, d, J=8.1 Hz), 7.67 (1H, dd, J=7.8, 0.9 Hz), 7.77 (2H, d, J=8.7 Hz) 7.80 (1H, s), 13.30 (1H, s).

Scheme of Reactions, Examples 11–16

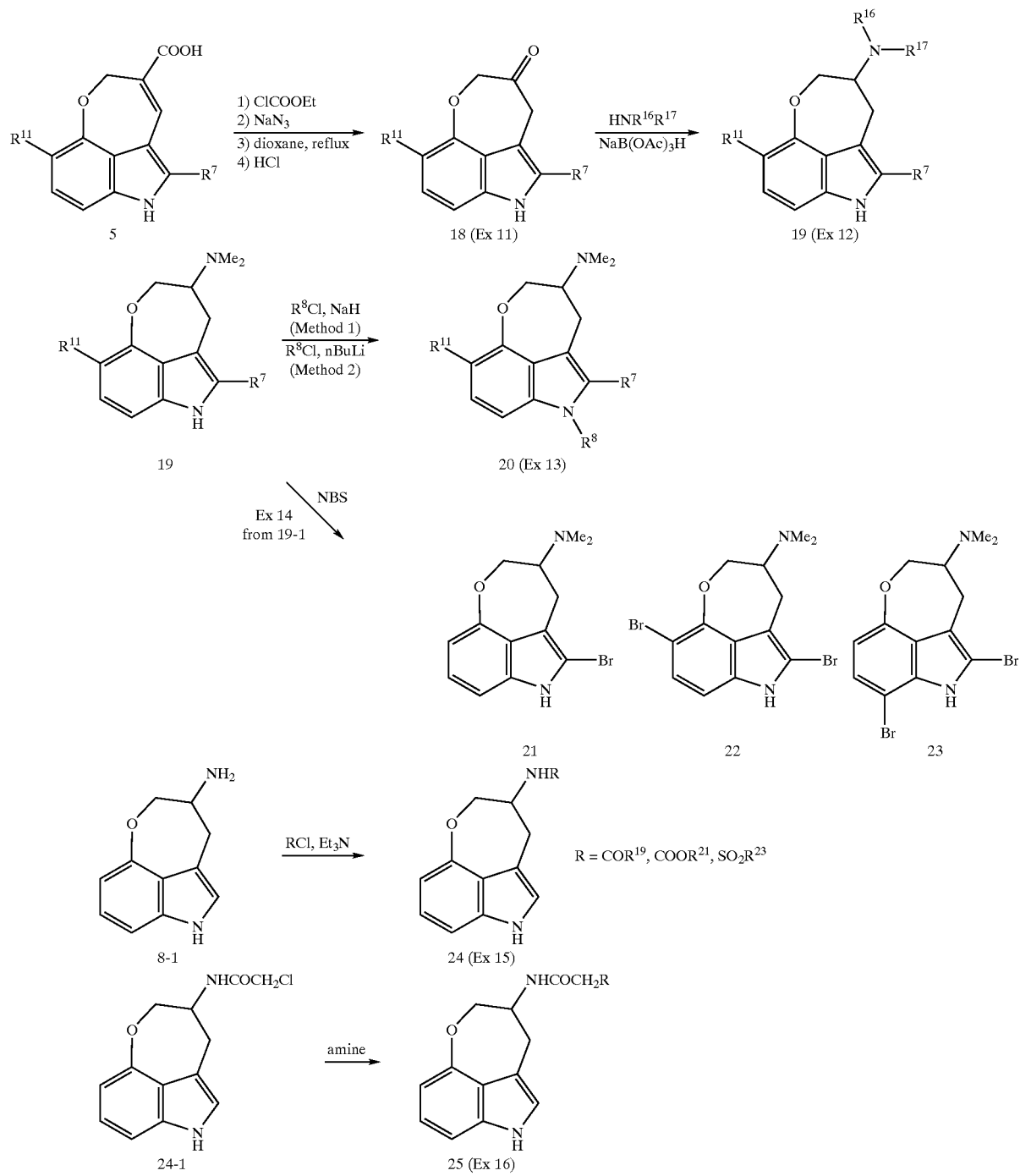

Example 11

2,9-Dihydro-6-oxa-2-azabenzo[cd]azulen-8-one (18-1) ($R^7=R^{11}=H$)

Triethylamine 10 ml and ethyl chlorocarbonate 5.6 ml were added to a solution of compound (5-1) 14.85 g in dry tetrahydrofuran 148 ml with cooling in ice-methanol bath. The mixture was stirred at that temperature for 30 min. Then, a solution sodium azide 8.97 g in water 59 ml was added dropwise. The mixture was stirred with cooling in ice for 4 h. To the reaction mixtures water was added. The mixture was extracted with ethyl acetate. The extracts were washed with brine, dried over anhydrous magnesium sulfate, concentrated under reduced pressure to give a yellow solid. The residue obtained was suspended in dioxane 280 ml. After the suspension was heated under reflux for 20 min, 1N HCl 58.3 ml was added with cooling in ice. Again, the mixture was heated under reflux for 20 min and cooled in ice-bath. Water was added. The mixture was extracted with ether. The extracts were washed with brine, dried over anhydrous magnesium sulfate and concentrated under reduced pressure. The residue obtained was chromatographed on silica gel 150 g in ethyl acetate:hexane (1:4) to give brown crystals, which was recrystallized from ether-petroleum ether to give the titled compound 7.94 g, m.p. 128–129° C. Yield 61%.

$^1$H-NMR(CDCl$_3$): 4.11 (2H, d, J=0.6 Hz), 4.69 (2H, s), 6.72–6.79 (1H, m), 6.92–6.95 (1H, m), 7.07–7.14 (2H, m), 8.12 (1H, br s).

Following compounds were obtained, according to the similar treatment.

| Compd No | $R^7$ | $R^{11}$ | m.p. (° C.) | $^1$H-NMR (CDCl$_3$) |
|---|---|---|---|---|
| 18-2 | Me | ME | 136–139 | 2.32 (3H, s), 2.33 (3H, s), 3.99 (2H, s), 4.66 (2H, s), 6.89 (1H, d, J=8.4 Hz), 6.92 (1H, d, J=8.4 Hz), 7.77 (1H, br s) |
| 18-3 | H | Br | 137–138 | 4.09 (2H, d, J=1.2 Hz), 4.75 (2H, s), 6.95 (1H, m), 7.01 (1H, d, J=8.7 Hz), 7.27 (1H, d, J=8.7 Hz), 8.14 (1H, br s) |

Example 12
Dimethyl-(2,7,8,9-tetrahydro-6-oxo-2-azabenzo[cd]azulen-8-yl)amine (19-1) ($R^7$=$R^{11}$=H; $R^{16}$=$R^{17}$=Me)

Dimethylamine (2 mol/tetrahydrofuran solution), compound (18-1) 690 mg, sodium triacetoxyborohydride 1.17 g and acetic acid 226 mg were dissolved in tetrahydrofuran 28 ml with cooling in ice. The mixture was stirred at room temperature for 1 h and allowed stand overnight. To the reaction mixture, ice-water and an aqueous sodium hydrogen carbonate solution were added. The mixture was extracted with ether. The extracts were washed with brine, dried over anhydrous magnesium sulfate and concentrated under reduced pressure. The residue obtained was chromatographed on aluminum oxide 30 g in chloroform:methanol (50:1) to give the titled compound as colorless crystals 689 mg. Yield 86%. This was recrystallized from ethyl acetate-hexane to give colorless crystals, m.p. 131–132.5° C.

$^1$H-NMR(CDCl$_3$): 2.42 (6H, s), 2.93–3.24 (3H, m), 4.15 (1H, dd, J=12.3, 6.6 Hz), 4.55 (1H, dd, J=12.3, 1.5 Hz), 6.62 (1H, dd, J=6.6, 0.9 Hz), 6.95–7.09 (3H, m), 8.14 (1H, br s).

Following compounds were obtained, according to the similar treatment.

| Compd No | $R^7$ | $R^{11}$ | $R^{16}$ | $R^{17}$ | m.p. (° C.) | $^1$H-NMR (CDCl$_3$) |
|---|---|---|---|---|---|---|
| 19-2 | H | H | H | Me | 112–116 oxalate | 2.56 (3H, s), 2.99–3.22 (3H, m), 4.27–4.38 (2H, m), 6.65 (1H, d, J=7.5 Hz), 6.96–7.09 (3H, m), 8.24 (1H, br s) |
| 19-3 | H | H | H | nPr | 137–139 | 0.93 (3H, t, J=7.5 Hz), 1.54 (2H, sex, J=7.5 Hz), 2.62–2.80 (2H, m), 2.92–3.02 (1H, m), 3.14–3.25 (2H, m), 4.19–4.30 (2H, m), 6.44–6.50 (1H, m), 6.90–7.02 (3H, m) CD$_3$OD |
| 19-4 | H | H | Et | Et | 123–124 | 1.12 (6H, t, J=7.5 Hz), 2.69 (4H, q, J=7.5 Hz), 2.90–3.00 (1H, m), 3.20–3.30 (2H, m), 4.08 (1H, dd, J=11.7, 6.3 Hz), 4.53 (1H, dd, J=11.7, 2.1 Hz), 6.41–6.48 (1H, m), 6.88–6.95 (2H, m), 7.01–7.03 (1H, m) CD$_3$OD |
| 19-5 | H | H | NPr | nPr | 60–61 | 0.90 (6H, t, J=7.5 Hz), 1.40–1.60 (4H, m), 2.40–2.60 (4H, m), 2.90–3.01 (1H, m), 3.15–3.35 (2H, m), 4.09 (1H, dd, J=12.3, 6.9 Hz), 4.61 (1H, dd, J=12.3, 1.8 Hz), 6.61 (1H, d, J=7.5 Hz), 6.95–6.98 (2H, m), 7.06 (1H, t, J=7.5 Hz), 8.06 (1H, br s) |
| 19-6 | H | H | H | cyclohexyl | 141–142 | 1.00–2.02 (10H, m), 2.64–2.74 (1H, m), 2.98 (1H, ddd, J=15.3, 8.4, 1.2 Hz), 3.14 (1H, dd, J=15.3, 3.6 Hz), 3.39–3.47 (1H, m), 4.23–4.32 (2H, m), 6.63 (1H, dd, J=7.5, 0.9 Hz), 6.95–6.99 (2H, m), 7.07 (1H, t, J=7.5 Hz), 8.11 (1H, br s) |
| 19-7 | H | H | H | allyl | 112–113 | 3.00–3.18 (2H, m), 3.28–3.49 (1H, m), 4.27–4.38 (2H, m), 5.08–5.13 (1H, m), 5.18–5.26 (1H, m), 5.86–5.99 (1H, m), 6.64 (1H, dd, J=7.8, 1.2 Hz), 6.95–7.00 (2H, m), 7.07 (1H, t, J=7.8 Hz), 8.11 (1H, br s) |
| 19-8 | H | H | H | iPr | 133–135 | 1.10 (3H, d, J=6.0 Hz), 1.11 (3H, d, J=6.0 Hz), 2.97–3.17 (3H, m), 3.35–3.42 (1H, m), 4.25–4.37 (2H, m), 6.64 (1H, dd, J=7.5, 0.9 Hz), 6.95–7.00 (2H, m), 7.07 (1H, t, J=7.5 Hz), 8.10 (1H, br s) |

-continued

| Compd No | R⁷ | R¹¹ | R¹⁶ | R¹⁷ | m.p. (° C.) | ¹H-NMR (CDCl₃) |
|---|---|---|---|---|---|---|
| 19-9 | H | H | H | H₂CH₂C-Ph | 104–106 | 2.83 (2H, t, J=7.5 Hz), 2.95–3.17 (4H, m), 3.26–3.33 (1H, m), 4.29 (2H, d, J=3.6 Hz), 6.62 (1H, d, J=7.5 Hz), 6.93–7.00 (2H, m), 7.07 (1H, t, J=7.8 Hz), 7.18–7.30 (5H, m), 8.08 (1H, br s) |
| 19-10 | H | H | | cyclopentyl | 137–139 | 1.80–1.89 (4H, m), 2.70–3.04 (6H, m), 3.37(1H, d, J=14.4 Hz), 4.17 (1H, dd, J=12.3, 6.3 Hz), 4.59 (1H, dd, J=12.3, 2.1 Hz), 6.61 (1H, dd, J=7.5, 0.9 Hz), 6.95–6.99 (2H, m), 7.06 (1H, t, J=7.8 Hz), 8.10 (1H, br s) |
| 19-11 | H | H | | cyclohexyl | 115–125 (dec.) oxalate | 1.45–1.75 (6H, m), 2.50–2.80 (4H, m), 2.94–3.12 (2H, m), 3.24–3.31 (1H, m), 4.10 (1H, dd, J=12.0, 6.3 Hz), 4.63 (1H, dd, J=12.0, 1.8 Hz), 6.61 (1H, dd, J=7.8, 0.9 Hz), 6.94–6.98 (2H, m), 7.06 (1H, t, J=7.8 Hz), 8.10 (1H, br s) |
| 19-12 | H | H | | N-Me piperidyl | 183–184 (dec.) oxalate | 2.32 (3H, s), 2.40–2.60 (4H, m), 2.62–2.73 (2H, m), 2.80–2.90 (2H, m), 2.95–3.11 (2H, m), 3.22–3.30 (1H, m), 4.12 (1H, dd, J=12.3, 6.3 Hz), 4.60 (1H, dd, J=12.3, 2.1 Hz), 6.61 (1H, dd, J=7.8, 0.9 Hz), 6.95–6.99 (2H, m), 7.06 (1H, t, J=7.8 Hz), 8.12 (1H, br s) |
| 19-13 | H | H | | tetrahydropyranyl | 207–208 | 2.46–2.56 (2H, m), 2.62–2.72 (2H, m), 2.76–2.98 (2H, m), 3.08–3.18 (1H, m), 3.53–3.62 (4H, m), 4.06 (1H, dd, J=12.3, 6.6 Hz), 4.45 (1H, d, J=12.3 Hz), 6.40 (1H, dd, J=6.6, 2.1 Hz), 6.86–6.94 (2H, m), 7.11 (1H, d, J=1.8 Hz), 10.95 (1H, br s) DMSO-d₆ |
| 19-14 | H | H | H | CH₂CH₂OH | 154–157 (dec.) oxalate | 2.85–3.11 (4H, m), 3.25–3.30 (2H, m), 3.62 (2H, t, J=5.4 Hz), 4.26–4.42 (2H, m), 6.64 (1H, dd, J=7.5, 0.9 Hz), 6.96–7.10 (3H, m), 8.16 (1H, br s) |
| 19-15 | H | Br | H | Me | 茶色油 | 2.58 (3H, s), 2.91–3.22 (3H, m), 4.34(1H, dd, J=12.6, 6.9 Hz), 4.44(1H, d, J=12.6 Hz), 6.86 (1H, d, J=8.4 Hz), 6.97 (1H, m), 7.28 (1H, d, J=8.4 Hz), 8.17 (1H, br s) |
| 19-16 | H | Br | Me | Me | 142–143 | 2.43 (6H, s), 2.92–3.23 (3H, m), 4.22 (1H, dd, J=12.3, 6.9 Hz), 4.67 (1H, dd, J=12.3, 1.8 Hz), 6.85 (1H, d, J=8.7 Hz), 6.98 (1H, m), 7.26 (1H, d, J=8.7 Hz), 8.13 (1H, br s) |
| 19-17 | Me | Me | Me | Me | 144–146 | 2.28 (3H, s), 2.34 (3H, s), 2.47 (6H, s), 2.82–3.11 (3H, m), 4.10 (1H, dd, J=12.0 Hz, 6.6 Hz), 4.58 (1H, d, J=12.0 Hz), 6.79 (1H, d, J=8.1 Hz), 6.87 (1H, d, J=8.1 Hz), 7.74 (1H, br s) |
| 19-18 | Me | Me | H | Me | 173–175 (dec.) oxalate | 2.29 (3H, s), 2.31 (6H, s), 2.57 (3H, s), 2.80–2.87 (1H, m), 2.97–3.03 (1H, m), 3.12–3.20 (1H, m), 4.29–4.32 (2H, m), 6.79 (1H, d, J=8.1 Hz), 6.87 (1H, d, J=8.1 Hz), 7.79 (1H, br s), |
| 19-19 | H | H | H | cyclopropyl | 130–131 | 0.34–0.55 (4H, m), 2.27–2.34 (1H, m), 3.02–3.18 (2H, m), 3.38–3.44 (1H, m), 4.33–4.44 (2H, m), 6.65 (1H, dd, J=7.5, 0.9 Hz), 6.94–7.07 (3H, m), 8.27 (1H, br s) |

-continued

| Compd No | $R^7$ | $R^{11}$ | $R^{16}$ | $R^{17}$ | m.p. (° C.) | $^1$H-NMR (CDCl$_3$) |
|---|---|---|---|---|---|---|
| 19-20 | H | H | H | CH$_2$CF$_3$ | 108–109 | 3.13 (2H, d, J=5.1 Hz), 3.27–3.44 (3H, m), 4.25 (1H, d, J=12.6 Hz), 4.40 (1H, dd, J=12.6, 6.9 Hz), 6.64 (1H, dd, J=8.1, 0.9 Hz), 6.98 (1H, s), 7.00 (1H, dd, J=8.1, 0.9 Hz), 7.08 (1H, t, J=8.1 Hz), 8.10 (1H, br s) |
| 19-21 | H | H | Me | Et | 122–124 | 1.13 (3H, t, J=7.2 Hz), 2.39 (3H, s), 2.54–2.79 (2H, m), 2.97–3.27 (3H, m), 4.12 (1H, dd, J=12.3, 6.3 Hz), 4.59 (1H, dd, J=12.3, 1.8 Hz), 6.62 (1H, dd, J=7.5, 0.9 Hz), 6.96–7.09 (3H, m), 8.12 (1H, br s) |
| 19-22 | H | H | H | Et | 139–141 | 1.14 (3H, t, J=7.2 Hz), 2.73–2.93 (2H, m), 3.00–3.19 (2H, m), 3.26–3.33 (1H, m), 4.27–4.37 (1H, m), 6.64 (1H, dd, J=7.5, 0.9 Hz), 6.96–6.99 (2H, m), 7.07 (1H, t, J=7.5 Hz), 8.15 (1H, br s) |

Example 13

(Method 1)

(2-Benzenesulfonyl-2,7,8,9-tetrahydro-6-oxo-2-azabenzo[cd]azulen-8-yl)dimethylamine oxalate (20-1) ($R^7$=$R^{11}$=H)

60% Sodium hydride 17 mg was added to a solution of compound (19-1) 75 mg in dry dimethylformamide 2.5 ml with cooling in ice. The mixture was stirred at 45° C. for 1 h. Benzenesulfonyl chloride 1 ml was added with cooling in ice. The mixture was stirred at room temperature for 21 h. Ice-water and an aqueous sodium hydrogen carbonate solution were added to the mixture, which was extracted with ether. The extracts were washed with brine, dried over anhydrous magnesium sulfate and concentrated under reduced pressure. The residue obtained was chromatographed on aluminum oxide in chloroform:hexane (1:2) to give the titled compound, 46 mg (yield 37%). This compound was treated with 1 eq. of oxalic acid to give the oxalic acid salt, which was recrystallized from ether-ethanol to give colorless crystals. m.p. 106–109° C.(dec.).

$^1$H-NMR(CDCl$_3$): 2.36 (6H, s), 2.80–3.12 (3H, m), 4.13 (1H, dd, J=12.3, 6.6 Hz), 4.42 (1H, dd, J=12.3, 0.6 Hz), 6.75 (1H, d, J=8.1 Hz), 7.14–7.20 (1H, m), 7.34 (1H, s), 7.41–7.61 (4H, m), 7.86–7.89 (2H, m)

Following compounds were obtained, according to the similar treatment.

| Comp No. | $R^7$ | $R^8$ | $R^{11}$ | m.p. | $^1$H-NMR (CDCl$_3$) |
|---|---|---|---|---|---|
| 20-2 | H | COPh | H | 126–129 (dec.) oxalate | 2.40 (6H, s), 2.86–3.16 (3H, m), 4.20 (1H, dd, J=12.3, 6.3 Hz), 4.50 (1H, d, J=12.3 Hz), 6.85 (1H, dd, J=7.2, 0.9 Hz), 7.06 (1H, s), 7.23–7.28 (1H, m), 7.49–7.63 (3H, m), 7.71 (2H, dd, J=8.4, 1.8 Hz), 8.04 (1H, dd, J=8.1, 0.9 Hz) |
| 20-3 | H | CH$_2$Ph | H | 183–186 (dec.) oxalate | 2.41 (6H, s), 2.88–3.06 (2H, m), 3.15–3.22 (1H, m), 4.15 (1H, dd, J=12.0, 6.3 Hz), 4.54 (1H, dd, J=12.0, 1.8 Hz), 5.23 (2H, s) 6.61 (1H, dd, J=7.8, 0.6 Hz), 6.85–6.89 (2H, m), 7.02–7.15 (3H, m), 7.25–7.33 (3H, m) |
| 20-4 | H | CH$_2$CONMe$_2$ | H | 119–124 (dec.) oxalate | 2.40 (6H, s), 2.99 (3H, s), 3.04 (3H, s), 2.88–3.22 (2H, m), 3.15–3.22 (1H, m), 4.13 (1H, dd, J=12.3, 6.6 Hz), 4.53 (1H, dd, J=12.3, 1.8 Hz), 4.82 (2H, s), 6.61 (1H, dd, J=8.1, 0.9 Hz), 6.79–7.10 (3H, m) |
| 20-5 | H | SO$_2$-naphthyl | H | 148–149 | 2.37 (6H, s), 2.89 (1H, m), 3.06–3.16 (2H, m), 4.15 (1H, dd, J=12.9, 6.9 Hz), 4.43 (1H, d, J=12.9 Hz), 6.71 (1H, dd, J=7.8, 0.6 Hz), 7.10 (1H, t, J=8.1 Hz), 7.39–7.67 (5H, m), 7.86–8.15 (3H, m), 8.76 (1H, d, J=8.7 Hz) |

| Comp No. | R$^7$ | R$^8$ | R$^{11}$ | m.p. | $^1$H-NMR (CDCl$_3$) |
|---|---|---|---|---|---|
| 20-6 | H | O$_2$S—(4-Cl-C$_6$H$_4$) | H | 114–118 (dec.) oxalate | 2.36 (6H, s), 2.81–3.11 (3H, m), 4.14 (1H, dd, J=12.6, 6.6 Hz), 4.43 (1H, d, J=12.6 Hz), 6.76 (1H, dd, J=7.8, 0.9 Hz), 7.18 (1H, t, J=8.4 Hz), 7.23 (1H, t, J=1.5 Hz), 7.38–7.42 (2H, m), 7.57 (1H, dd, J=8.4, 0.9 Hz), 7.77–7.82 (2H, m) |
| 20-7 | H | SO$_2$Et | H | 153–155 (dec.) oxalate | 1.23 (3H, t, J=7.5), 2.41 (6H, s), 2.87–3.14 (3H, m), 3.28 (3H, q, J=7.5 Hz), 4.22 (1H, dd, J=12.3, 6.6 Hz), 4.49 (1H, d, J=12.3 Hz), 6.82 (1H, d, J=7.8 Hz), 7.19–7.27 (2H, m), 7.50 (1H, J=8.4 Hz) |
| 20-8 | H | IPr | H | 191–194 (dec.) oxalate | 1.49 (3H, t, J=6.3 Hz), 1.50 (3H, t, J=6.3 Hz), 2.42 (6H, s), 2.93–3.24 (3H, m), 4.13 (1H, dd, J=12.3, 6.6 Hz), 4.54 (1H, dd, J=12.3, 1.8 Hz), 4.57–4.66 (1H, m), 6.59 (1H, dd, J=7.8, 1.2 Hz), 6.94 (1H, d, J=7.5 Hz), 7.01 (1H, s), 7.07 (1H, d, J=7.8 Hz) |
| 20-9 | H | O$_2$S—(2-thienyl) | H | 142–144 (dec.) oxalate | 2.37 (6H, s), 2.81–3.10 (3H, m), 4.16 (1H, dd, J=12.3, 6.6 Hz), 4.43 (1H, dd, J=12.3 Hz), 6.78 (1H, d, J=8.4 Hz), 7.00 (1H, dd, J=4.8, 3.9 Hz), 7.21 (1H, t, J=8.4 Hz), 7.30 (1H, s), 7.53 (1H, dd, J=5.1, 1.5 Hz), 7.62 (1H, d, J=8.4 Hz), 7.67 (1H, dd, J=4.2, 1.5 Hz) |
| 20-10 | H | O$_2$S—(4-CF$_3$-C$_6$H$_4$) | H | 119–122 (dec.) oxalate | 2.37 (6H, s), 2.82–2.88 (1H, m), 2.96–3.11 (2H, m), 4.16 (1H, dd, J=12.6, 6.6 Hz), 4.43 (1H, d, J=12.6 Hz), 6.78 (1H, dd, J=8.1, 0.9 Hz), 7.17–7.32 (2H, m), 7.59 (1H, dd, J=8.1, 0.6 Hz), 7.71 (2H, d, J=8.4 Hz), 8.00 (2H, d, J=8.1 Hz) |
| 20-11 | H | O$_2$S—(4-Br-C$_6$H$_4$) | H | 147–150 (dec.) oxalate | 2.37 (6H, s), 2.82–3.12 (3H, m), 4.14 (1H, dd, J=12.6, 6.6 Hz), 4.43 (1H, d, J=12.6 Hz), 6.77 (1H, dd, J=7.8, 0.6 Hz), 7.18 (1H, t, J=8.1 Hz), 7.30 (1H, s), 7.55–7.58 (2H, m), 7.71–7.74 (2H, m) |
| 20-12 | H | O$_2$S—(3-Br-C$_6$H$_4$) | H | 168–171 (dec.) oxalate | 2.37 (6H, s), 2.81–3.11 (3H, m), 4.16 (1H, dd, J=12.3, 6.6 Hz), 4.42 (1H, d, J=12.3 Hz), 6.77 (1H, dd, J=8.1, 0.3 Hz), 7.20 (1H, t, J=8.1 Hz), 7.30–7.34 (2H, m), 7.57 (1H, d, J=8.1 Hz), 7.64–7.81 (2H, m), 8.01 (1H, t, J=1.8 Hz) |
| 20-13 | H | O$_2$S—(2-Br-C$_6$H$_4$) | H | 173–176 (dec.) oxalate | 2.40 (6H, s), 2.86–3.11 (3H, m), 4.21 (1H, dd, J=12.3, 6.6 Hz), 4.60 (1H, d, J=12.3 Hz), 6.75 (1H, dd, J=8.1, 0.6 Hz), 7.09 (1H, t, J=8.1 Hz), 7.23–7.26 (1H, m), 7.36–7.50 (2H, m), 7.55 (1H, s), 7.67 (1H, dd, J=7.8, 1.5 Hz), 8.09 (1H, dd, J=7.8, 1.5 Hz) |
| 20-14 | H | O$_2$S—(4-OMe-C$_6$H$_4$) | H | 140–142 (dec.) oxalate | 2.37 (6H, s), 2.81–3.11 (3H, m), 3.80 (3H, s), 4.13 (1H, dd, J=12.3, 6.6 Hz), 4.43 (1H, d, J=12.3 Hz), 6.74 (1H, d, J=8.1 Hz), 6.88 (2H, dd, J=6.9, 2.1 Hz), 7.17 (1H, t, J=8.4 Hz), 7.33 (1H, s), 7.58 (1H, d, J=8.1 Hz), 7.82 (1H, dd, J=6.9, 2.1 Hz) |
| 20-15 | H | O$_2$S—(3,4-diOMe-C$_6$H$_3$) | H | 123–126 (dec.) oxalate | 2.37 (6H, s), 2.82–3.11 (3H, m), 3.85 (3H, s), 3.87 (3H, s), 4.14 (1H, dd, J=12.3, 5.7 Hz), 4.44 (1H, d, J=12.3 Hz), 6.75 (1H, dd, J=7.8, 0.9 Hz), 6.84 (2H, d, J=8.7 Hz), 7.17 (1H, t, J=8.1 Hz), 7.26–7.32 (2H, m), 7.51 (1H, dd, J=8.4, 2.1 Hz), 7.61 (1H, dd, J=8.4, 0.6 Hz) |

-continued

| Comp No. | R⁷ | R⁸ | R¹¹ | m.p. | ¹H-NMR (CDCl₃) |
|---|---|---|---|---|---|
| 20-16 | H | O₂S-CH=CH-Ph (styryl sulfonyl) | H | 169–171 (dec.) oxalate | 2.39 (6H, s), 2.85–3.13 (3H, m), 4.19 (1H, dd, J=12.6, 6.3 Hz), 4.46 (1H, d, J=12.6 Hz), 6.74 (1H, d, J=15.3 Hz), 6.80 (1H, dd, J=8.4, 0.6 Hz), 7.20 (1H, t, J=8.4 Hz), 7.27–7.45 (6H, m), 7.52 (1H, dd, J=8.1, 0.9 Hz), 7.70 (1H, d, J=15.5 Hz) |
| 20-17 | H | O₂S-(2,5-dichlorophenyl) | H | 161–163 (dec.) oxalate | 2.39 (6H, s), 2.84–3.09 (3H, m), 4.21 (1H, dd, J=12.3, 5.4 Hz), 4.44 (1H, d, J=12.3 Hz), 6.77 (1H, dd, J=8.4, 0.9 Hz), 7.13 (1H, t, J=8.4 Hz), 7.25 (1H, dd, J=8.1, 0.9 Hz), 7.35 (1H, d, J=8.4 Hz), 7.43–7.48 (2H, m), 8.19 (1H, d, J=2.4 Hz) |
| 20-18 | H | SO₂Ph | Br | 89–90 | 2.39 (6H, s), 2.85–3.10 (3H, m), 4.24 (1H, dd, J=12.3, 6.3 Hz), 4.54 (1H, d, J=12.3 Hz), 7.34 (1H, s), 7.39–7.59 (5H, m), 7.84–7.87 (2H, m) |
| 20-19 | H | O₂S-(4-fluorophenyl) | H | 143–144 (dec.) oxalate | 2.37 (6H, s), 2.82–2.88 (1H, m), 2.96–3.11 (2H, m), 4.15 (1H, dd, J=12.6, 6.6 Hz), 4.42 (1H, d, J=12.6 Hz), 6.76 (1H, d, J=7.8 Hz), 7.08–7.21 (3H, m), 7.25 (1H, dd, J=8.1, 0.9 Hz), 7.31 (1H, s), 7.56 (1H, d, J=8.4 Hz), 7.87–7.92 (2H, m) |
| 20-20 | H | O₂S-(4-bromo-2,5-difluorophenyl) | H | 128–131 (dec.) oxalate | 2.40 (6H, s), 2.85–2.91 (1H, m), 3.07–3.10 (2H, m), 4.21 (1H, dd, J=12.6, 6.6 Hz), 4.44 (1H, d, J=12.6 Hz), 6.79 (1H, dd, J=8.1, 0.9 Hz), 7.12 (1H, t, J=8.1 Hz), 7.33–7.42 (3H, m), 7.78 (1H, dd, J=7.2, 6.0 Hz) |
| 20-21 | H | O₂S-(5-chlorothien-2-yl) | H | 154–156 (dec.) oxalate | 2.38 (6H, s), 2.83–3.13 (3H, m), 4.18 (1H, dd, J=12.6, 6.6 Hz), 4.44 (1H, d, J=12.6 Hz), 6.80 (1H, dd, J=8.1, 0.6 Hz), 6.83 (1H, d, J=4.2 Hz), 7.19–7.25 (2H, m), 7.46 (1H, d, J=4.1 Hz), 7.56 (1H, dd, J=8.1, 0.6 Hz) |
| 20-22 | H | O₂S-(2,4-difluorophenyl) | H | 163–164 (dec.) oxalate | 2.38 (6H, s), 2.82–3.09 (3H, m), 4.19 (1H, dd, J=12.3, 6.3 Hz), 4.44 (1H, d, J=12.3 Hz), 6.75–7.03 (3H, m), 7.13 (1H, t, J=8.1 Hz), 7.38–7.41 (2H, m), 8.02–8.11 (1H, m) |
| 20-23 | H | O₂S-(2,5-dimethoxyphenyl) | H | 147–150 (dec.) oxalate | 2.39 (6H, s), 2.84–3.10 (3H, m), 3.66 (3H, s), 3.82 (3H, s), 4.18 (1H, dd, J=12.3, 6.6 Hz), 4.44 (1H, d, J=12.3 Hz), 6.72 (1H, dd, J=8.1, 0.9 Hz), 6.81 (1H, d, J=9.0 Hz), 7.04 (1H, dd, J=9.0, 3.3 Hz), 7.09 (1H, t, J=8.1 Hz), 7.36 (1H, d, J=8.1 Hz), 7.43 (1H, s), 7.60 (1H, d, J=3.3 Hz) |
| 20-24 | H | O₂S-(3-methoxyphenyl) | H | 103–104 | 2.37 (6H, s), 2.82–3.12 (3H, m), 3.79 (3H, s), 3.82 (3H, s), 4.15 (1H, dd, J=12.6, 6.6 Hz), 4.43 (1H, d, J=12.6 Hz), 6.75 (1H, dd, J=8.1, 0.6 Hz), 7.03–7.07 (1H, m), 7.17 (1H, t, J=8.1 Hz), 7.31–7.46 (4H, m), 7.60 (1H, dd, J=8.1, 0.6 Hz) |

-continued

| Comp No. | R⁷ | R⁸ | R¹¹ | m.p. | ¹H-NMR (CDCl₃) |
|---|---|---|---|---|---|
| 20-25 | H | (5-sulfonylthiophen-2-yl)isoxazol-3-yl group (O₂S-thiophene-isoxazole) | H | 113–115 (dec.) oxalate | 2.32 (6H, s), 2.81–3.12 (3H, m), 4.17 (1H, dd, J=12.6, 6.3 Hz), 4.44 (1H, d, J= 12.6 Hz), 6.46 (1H, d, J=1.8 Hz), 6.80 (1H, d, J=7.8 Hz), 7.24 (1H, t, J=8.1 Hz), 7.29 (1H, d, J=3.9 Hz), 7.33 (1H, d, J=3.9 Hz), 7.61 (1H, d, J=7.8 Hz), 7.64 (1H, d, J=3.9 Hz), 8.27 (1H, d, J =1.8 Hz) |
| 20-26(*) | H | SO₂Ph | H | 98–98 (dec.) oxalate | 1.09 (3H, t, J=7.2 Hz), 2.34 (3H, s), 2.50–2.74 (2H, m), 2.91–3.16 (3H, m), 4.05 (1H, dd, J=12.0, 6.6 Hz), 4.51 (1H, dd, J=12.0, 0.9 Hz), 6.74 (1H, dd, J= 8.1, 0.6 Hz), 7.17 (1H, t, J=8.1 Hz), 7.34 (1H, s), 7.41–7.61 (5H, m), 7.86–7.89 (2H, m) |
| 20-27 | Me | SO₂Ph | Me | 155–158 (dec.) oxalate | 2.24 (3H, s), 2.39 (6H, s), 2.52 (3H, s), 4.05 (1H, dd, J=12.6, 5.7 Hz), 4.46 (1H, d, J=12.6 Hz), 7.01 (1H, d, J=8.7 Hz), 7.38–7.43 (2H, m), 7.49–7.55 (1H, m), 7.71–7.77 (3H, m) |

(*)20-26; R⁴=N(Me)Et (Method 2)

(2-Benzenesulfonyl-2,7,8,9-tetrahydro-6-oxo-2-azabenzo[cd]azulen-8-yl)dimethylamine (20-1)

n-BuLi (1.56 mol/l hexane solution) 1.39 ml was added to a solution of compound (19-1) 432 mg in dry tetrahydrofuran 10 ml at −70° C. under nitrogen atmosphere. The solution was stirred at that temperature for 1 h and at −30° C. for 1 h. Then, the temperature was again lowered to −70° C. and benezenesulofonyl chloride 396 mg was added dropwise. The reaction temperature was allowed to raise gradually to the room temperature. The mixture was stirred at room temperature, poured to ice and an aqueous ammonium chloride solution and extracted with chloroform. The chloroform layer was washed with brine, dried over anhydrous magnesium sulfate and concentrated under reduced pressure. The residue obtained was choromatographed on aluminum oxide 12 g in chloroform:hexane (8:1) to give the titled compound as crystals. Yield 83%. The product was recrystallized from ethyl acetate isopropyl ether to give colorless crystals. m.p. 114–116° C.

¹H-NMR(CDCl₃): 2.36 (6H, s), 2.80–3.12 (3H, m), 4.13 (1H, dd, J=12.3, 6.6 Hz), 4.42 (1H, dd, J=12.3, 0.6 Hz), 6.75 (1H, d, J=8.1 Hz), 7.14–7.20 (1H, m), 7.34 (1H, s), 7.41–7.61 (4H, m), 7.86–7.89 (2H, m)

Example 14

(1-Bromo-2,7,8,9-tetrahydro-6-oxa-2-azabenzo[cd]azulen-8-yl)dimethylamine (21), (1,5-Dibromo-2,7,8,9-tetrahydro-6-oxa-2-azabenzo[cd]azulen-8-yl)dimethyl-amine (22) and (1,3-Dibromo-2,7,8,9-tetrahydro-6-oxa-2-azabenzo[cd]azulen-8-yl)dimethyl-amine (23)

N-Bromosuccinimide 214 mg was added to a warm solution of compound (19-1) 216 mg in carbon tetrachloride 33 ml and the mixture was heated under reflux for 2 h. After the reaction ceased, the insoluble materials were removed by filtration and washed with chloroform. The filtrate was concentrated under reduced pressure. The residue obtained was chromatographed on silica gel in chloroform:methanol (30:1). The eluent was chromatographed on thin silica gel plates in chloroform:methanol (30:1) to give the titled compound (21) 51 mg. Yield 17%. This was recrystallized from ethyl acetate-ether to give crystals, m.p. 170–172° C.

¹H-NMR(CDCl₃): 2.43 (6H, s), 2.88–3.08 (3H, m), 4.15 (1H, dd, J=12.3, 6.0 Hz), 4.52 (1H, d, J=12.3 Hz), 6.62 (1H, dd, J=7.8, 0.9 Hz), 6.89 (1H, dd, J=8.1, 0.9 Hz), 7.04 (1H, t, J=7.8 Hz), 8.07 (1H, br s)

1,5-Dibromo compound (22) 15 mg was isolated from another fraction. Yield 4% Purifying from ether gave crystals, m.p. 123–126° C.

¹H-NMR(CDCl₃): 2.44 (6H, s), 2.84–3.08 (3H, m), 4.21 (1H, dd, J=12.0, 6.9 Hz), 4.66 (1H, d, J=12.0 Hz), 6.78 (1H, d, J=8.7 Hz), 7.25 (1H, d, J=8.7 Hz), 8.49 (1H, br s)

The mother liquor of the above mentioned 1,5-dibromo compound (22) was concentrated under reduced pressure and again chromatographed on thin silica gel plates in chloroform:methanol (30:1) to give the 1,3-dibromo compound (23) 8 mg (yield 2%). This was treated with 1 eq. oxalic acid to give the salt, m.p. 147–152° C. (dec.).

¹H-NMR(CDCl₃): 2.42 (6H, s), 2.90–3.05 (3H, m), 4.09–4.16 (1H, m), 4.50 (1H, d, J=12.0 Hz), 6.53 (1H, d, J=8.1 Hz), 7.15 (1H, d, J=8.1 Hz), 8.22 (1H, br s)

Example 15

2-Chloro-N-(2,7,8,9-tetrahydro-6-oxo-2-azabenzo[cd]azulen-8-yl)acetamide (24-1) (R=COCH₂Cl)

Compound (8-1) 535 mg was dissolved in dry tetrahydrofuran 15 ml. Triethylamine 345 mg and chloroacetyl chloride 0.25 ml were added to the solution with cooling in ice. The mixture was stirred for 1 h and at room temperature for 30 min. Ice-water was added to the mixture with cooling in ice. The mixture was extracted with ethyl acetate. The extracts were washed with brine, dried over anhydrous magnesium sulfate and concentrated under reduced pressure. The residue obtained was chromatographed on silica gel 25 g in ethyl acetate:hexane (2:1) to give the titled compound 706 mg (94%) as a colorless oil.

$^1$H-NMR(CDCl$_3$): 3.06–3.14 (1H, m), 3.36–3.43 (1H, m), 3.95–4.06 (2H, m), 4.08–4.16 (1H, m), 4.27 (1H, d, J=11.4 Hz), 4.54–4.64 (2H, m), 6.70 (1H, dd, J=7.5, 1.2 Hz), 6.99 (1H, s), 7.03–7.13 (2H, m), 8.18 (1H, br s)

Following compounds were obtained, according to the similar treatment.

| Compd No | R | m.p. | $^1$H-NMR (CDCl$_3$) |
|---|---|---|---|
| 24-2 | COOMe | Colorless oil | 3.02–3.07 (1H, m), 3.33–3.39 (1H, m), 3.63 (3H, s), 4.23 (1H, d, J=9.3 Hz), 4.34–4.41 (1H, m), 4.53–4.60 (1H, m), 5.25 (1H, br d), 6.67 (1H, d, J=7.8 Hz), 6.97 (1H, s), 7.00–7.11 (2H, m), 8.14 (1H, br s) |
| 24-3 | Ms | Colorless oil | 3.02 (3H, s), 3.07–3.14 (1H, m), 3.35–3.42 (1H, m), 4.19–4.27 (2H, m), 4.54–4.61 (1H, m), 4.84 (1H, d, J=8.7 Hz), 6.68 (1H, d, J=7.5 Hz), 7.00–7.12 (3H, m), 8.22 (1H, br s) |
| 24-4 | SO$_2$NHMe | Yellow oil | 2.70 (3H, d, J=5.4 Hz), 3.04–3.11 (1H, m), 3.35–3.42 (1H, m), 4.03–4.28 (3H, m), 4.53–4.60 (1H, m), 4.81 (1H, d, J=8.4 Hz), 6.67 (1H, dd, J=7.2, 1.2 Hz), 6.98–7.11 (3H, m), 8.24 (1H, br s) |
| 24-5 | COMe | 174–176 | 1.92 (3H, s), 2.99–3.06 (1H, m), 3.35–3.41 (1H, m), 4.21–4.25 (1H, m), 4.53–4.68 (2H, m), 6.03 (1H, br s), 6.69 (1H, d, J=7.2 Hz), 6.98 (1H, s), 7.03–7.13 (2H, m), 8.21 (1H, br s) |

Example 16

2-Cyclohexylamino-N-(2,7,8,9-tetrahydro-6-oxo-2-azabenzo[cd]azulen-8-yl)acetamide (25-1)

A solution of compound (24-1) 160 mg and cyclohexylamine 360 mg in benzene 4 ml and methanol 4 ml was heated at 60° C. for 21 h and concentrated under reduced pressure. Water was added to the residue obtained. The mixture was extracted with chloroform. The extracts were washed with brine, dried over anhydrous magnesium sulfate and concentrated under reduced pressure. The residue obtained was chromatographed on silica gel in ethyl acetate-:methanol (30:1) to give the titled compound 161 mg as crystals. Yield 81%. The crude crystalline materials were recrystallized from methanol-ethyl acetate to give colorless crystals, m.p. 184–186° C.

$^1$H-NMR(CDCl$_3$): 0.43–1.04 (4H, m), 1.22–1.57 (6H, m), 1.98–2.07 (1H, m), 3.02–3.46 (4H, m), 4.24–4.29 (1H, m), 4.54–4.59 (2H, m), 6.69 (1H, dd, J=7.5, 0.9 Hz), 6.96–7.11 (3H, m), 7.96 (1H, br s), 8.13 (1H, br s)

Following compounds were obtained, according to the similar treatment.

| Compd No | R | m.p. | $^1$H-NMR (CDCl$_3$) |
|---|---|---|---|
| 25-2 | NMe$_2$ | 161–162.5 | 2.06 (6H, s), 2.84–2.96 (2H, m), 3.06–3.13 (1H, m), 3.31–3.39 (1H, m), 4.26 (1H, d, J=11.4 Hz), 4.52–4.62 (2H, m), 6.68 (1H, dd, J=7.5, 0.9 Hz), 6.97–7.11 (3H, m), 7.53 (1H, br s), 8.21 (1H, br s) |

Scheme of Reactions, Examples 17–25

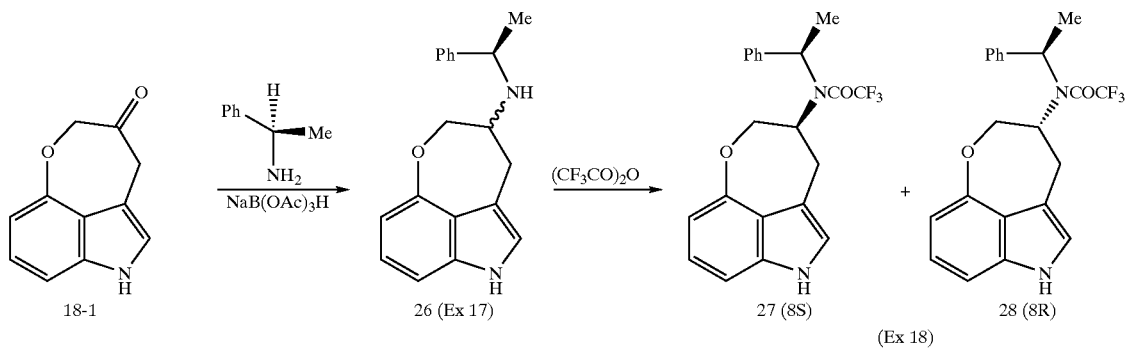

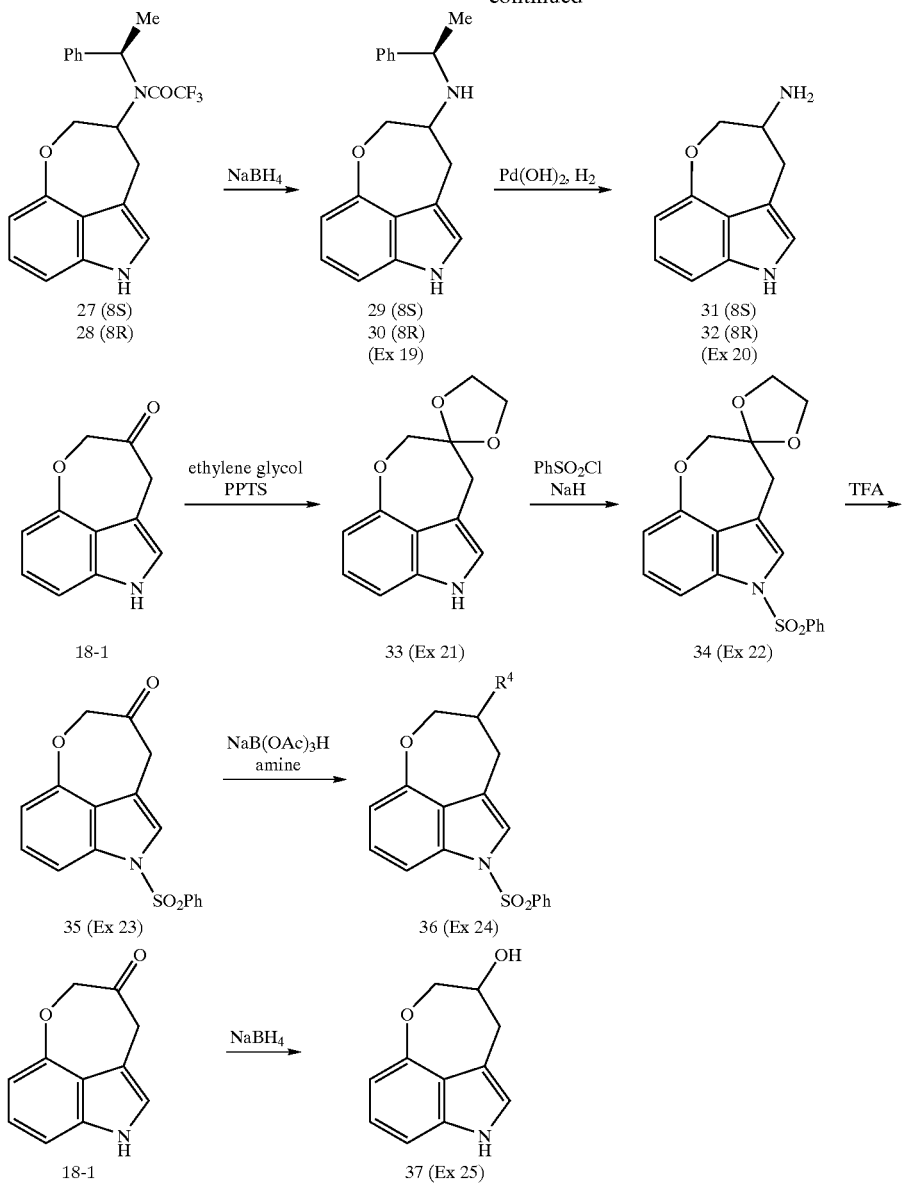

Example 17

((R)-1-Phenylethyl)-2,7,8,9-tetrahydro-6-oxa-2-azabenzo[cd]azulen-8-ylamine (26)

Sodium triacetoxyborohydride 318 mg and acetic acid 57 μl were added to a solution of compound (18-1) 187.6 mg and (R)-(+)-α-methylbenzylamine 13.7 mg in dry tetrahydrofuran 8 ml at room temperature and the mixture was stirred for 18 h. Water was added. The reaction mixture was made alkaline with an aqueous saturated sodium hydrogencarabonate solution and extracted with ether. The extracts were washed with brine, dried over anhydrous magnesium sulfate and concentrated under reduced pressure. The residue obtained was chromatographed on aluminum oxide 40 g in ethyl acetate:hexane (1:2) to give the titled compound 250 mg as a colorless oil. Yield 86%. The $^1$H-NMR shows the titled compound is a mixture of their diastereomers.

$^1$H-NMR(CDCl$_3$): 1.33 (total 6H, d, J=6.6 Hz), 2.98–3.22 (total 6H, m), 4.04–4.41 (total 6H, m), 6.61–6.65 (total 2H, m), 6.91–7.41 (total 16H, m), 8.07 (total 2H, br s).

Example 18

2,2,2-Trifluoro-N-((R)-1-phenylethyl)-N-(S)-2,7,8,9-tetrahydro-6-oxa-2-azabenzo[cd]azulen-8-ylacetamide (27) and 2,2,2-Trifluoro-N-((R)-1-phenylethyl)-N-(R)-2,7,8,9-tetrahydro-6-oxa-2-azabenzo[cd]azulen-8-ylacetamide (28)

Compound (26) 2.548 g was dissolved in dry tetrahydrofuran 8 ml. A solution of triethylamine 1.34 ml and trifluoroacetic anhydride 2.014 g in dry tetrahydrofuran 1 ml was added to the solution with cooling in ice. The mixture was stirred for 1 h. Furthermore, triethylamine 177 mg, trifluoroacetic anhydride 366 mg were added and the mixture was stirred for 1 h with cooling in ice. The solvents were removed by distillation under reduced pressure. Water was added to the residue. The mixture was extracted with ether. The extracts were washed with brine, dried over anhydrous magnesium sulfate and concentrated under reduced pressure. The residue obtained was chromatographed on silica gel in ethyl acetate:hexane (1:5) repeatedly to give the titled compound (27) as a colorless oil, 990 mg (yield 29%) and the titled compound (28) as a colorless oil 1.672 g (yield 49%).

Compound (27)

$^1$H-NMR(CDCl$_3$): 1.82 (3H, d, J=6.9 Hz), 2.07–2.19 (1H, m), 3.54–3.66 (2H, m), 4.43 (1H, dd, J=12.9, 2.4 Hz), 4.81 (1H, dd, J=12.9, 6.0 Hz), 5.40 (1H, q, J=6.9 Hz), 6.61 (1H, dd, J=7.5, 0.9 Hz), 6.64 (1H, m), 6.94 (1H, dd, J=7.5, 0.9 Hz), 7.04 (1H, t, J=7.5 Hz), 7.27–7.40 (5H, m), 7.96 (1H, br s).

Compound (28)

$^1$H-NMR(CDCl$_3$): 1.72 (3H, d, J=6.9 Hz), 3.00–3.08 (1H, m), 3.55–3.63 (1H, m), 3.85–3.96 (1H, m), 4.10 (1H, dd, J=12.6, 2.4 Hz), 4.63 (1H, dd, J=12.6, 6.3Hz), 5.39 (1H, q, J=6.9 Hz), 6.43 (1H, dd, J=7.5, 1.2 Hz), 6.91–7.01 (3H, m), 7.34–7.44 (5H, m), 8.08 (1H, br s).

Example 19

((R)-1-Phenylethyl)-(S)-2,7,8,9-tetrahydro-6-oxa-2-azabenzo[cd]azulen-8-ylamine (29)

Compound (27) 934 mg was dissolved in ethanol 19 ml and sodium borohydride 364 mg was added to the solution at room temperature. The mixture was stirred for 17 h. Water was added with cooling in ice. The mixture was extracted with ethyl acetate. The extracts were washed with brine, dried over anhydrous magnesium sulfate and concentrated under reduced pressure. The residue obtained was chromatographed on silica gel in ethyl acetate:hexane (1:1) to give the titled compound (29) 695 mg. Yield 99.9%. Furthermore, the titled compound (29) was treated with a solution of hydrogen chloride in methanol to give the HCl salt, which was recrystallized from methanol-isopropanol to give colorless crystals, m.p. 233–240° C. (dec.). The absolute configuration was determined by an X-ray crystal structure analysis on a single crystal.

$^1$H-NMR(CDCl$_3$): 1.33 (3H, d, J=6.3 Hz), 3.00–3.22 (3H, m), 4.03 (1H, q, J=6.3 Hz), 4.21 (1H, d, J=11.7 Hz), 4.29–4.36 (1H, m), 6.63 (1H, dd, J=7.8, 0.9 Hz), 6.95–6.99 (2H, m), 7.06 (1H, t, J=7.8 Hz), 7.20–7.42 (5H, m), 8.07 (1H, br s).

According to the similar manner, ((R)-1-Phenylethyl)-(R)-2,7,8,9-tetrahydro-6-oxa-2-azabenzo[cd]azulen-8-ylamine (30) was obtained.

$^1$H-NMR(CDCl$_3$): 1.33 (3H, d, J=6.6 Hz), 2.80–3.15 (3H, m), 4.11 (1H, q, J=6.3 Hz), 4.26 (1H, d, J=12.0 Hz), 4.37 (1H, dd, J=12.0, 6.3 Hz), 6.64 (1H, dd, J=7.8, 0.9 Hz), 6.91–6.93 (1H, m), 6.96 (1H, dd, J=7.8, 0.9 Hz), 7.06 (1H, t, J=7.8 Hz), 7.20–7.41 (5H, m), 8.06 (1H, br s).

Example 20

(S)-2,7,8,9-Tetrahydro-6-oxa-2-azabenzo[cd]azulen-8-ylamine (31)

Compound (29) 609 mg was dissolved in tetrahydrofuran 20 ml. 20% Palladium(II)hydroxide 200 mg was added. A mixture was stirred in a hydrogen atomosphere for 22 h. The catalyst was filtered off and the filtrate was concentrated under reduced pressure. The residue obtained was chromatographed on aluminum oxide in chloroform to give the titled compound (31) as pale brown crystals, 337 mg. Yield 86%. Furthermore, this was recrystallized from methanol-isopropanol to give the titled compound (31) as pale brown crystals, m.p. 202–203° C.

$[\alpha]_D$+38.7±1.6° (C=0.509, methanol, 25° C.)

According to the similar manner, (R)-2,7,8,9-Tetrahydro-6-oxa-2-azabenzo[cd]azulen-8-ylamine (32) was obtained.

m.p. 202–203° C. $[\alpha]_D$−38.8±1.6° (C=0.508, methanol, 25° C.)

Example 21

2,9-Dihydro-6-oxa-2-azabenzo[cd]azulen-8-one ethylene ketal (33)

Ethylene glycol 2.56 g and pyridinium p-toluenesulfonate 250 mg were added to a solution of compound (18-1) 1.877 g in benzene 50 ml. The mixture was heated under reflux for 14 h by use of a Dean-Stark apparatus. The reaction mixture separated into two layers. The upper layer was separated by decantation. Water and dioxane were added to the remained black oily part. The insoluble materials were removed by filtration and the filtrate was extracted with toluene. The extracts were washed with brine, treated with char coal, dried over anhydrous magnesium sulfate and concentrated under reduced pressure to give brown crystals. The above obtaied upper layer was washed with water, an aqueous saturated sodium hydrogen carbonate solution and brine successively, treated with char-coal and dried over anhydrous magnesium sulfate and concentrated under reduced pressure to give colorless crystals. The combined crystals were recrystallized from tetrahydrofuran to give the titled compound (33) as colorless crystals, m.p. 200–202° C., 925 mg. Yield 40%.

$^1$H-NMR(DMSO-d$_6$): 3.16 (2H, s), 3.97 (4H, s), 4.13 (2H, s), 6.41 (1H, dd, J=6.6, 1.8 Hz), 6.88–6.96 (2H, m), 7.07 (1H, m), 10.94 (1H, br s).

Example 22

2-Benzenesulfonyl-2,9-dihydro-6-oxa-2-azabenzo[cd]azulen-8-one ethylene ketal (34)

60% Sodium hydride 33 mg was added to a solution of compound (33) in dry dimethylformamide 2 ml with cooling in ice and the mixture was stirred for 10 min. Then, benzenesulfonyl chloride 152 mg was added. The mixture was heated at 60° C. for 14 h. Ice-water was added to the reaction mixtures, which was extracted with ethyl acetate. The extracts were washed with brine, dried over anhydrous magnesium sulfate and concentrated under reduced pressure. The residue obtained was choromatographed on aluminum oxide in chloroform:hexane (1:1) to give the titled compound (34) as a pale yellow oil, 187 mg. Yield 69%.

$^1$H-NMR(CDCl$_3$): 3.22 (2H, s), 4.07 (4H, s), 4.16 (2H, s), 6.80 (1H, dd, J=8.1, 0.9 Hz), 7.18 (1H, t, J=8.1 Hz), 7.33 (1H, m), 7.42–7.58 (3H, m), 7.62 (1H, dd, J=8.4, 0.9 Hz), 7.88–7.92 (2H, m).

Example 23

2-Benzenesulfonyl-2,9-dihydro-6-oxa-2-azabenzo[cd]azulen-8-one (35)

Trifluoroacetic acid 1 ml and water 0.1 ml were added to compound (34) 48.4 mg. The mixture was heated at 80° C. for 15 min and concentrated under reduced pressure. Ice-water was added to the residue, which was made alkaline with an aqueous saturated sodium hydrogen carbonate solution and extracted with ethyl acetate. The extracts were washed with brine, dried over anhydrous magnesium sulfate and concentrated under reduced pressure. The residue obtained was chromatographed on silica gel in ethyl acetate-:hexane (1:2) to give the titled compound (35) as a colorless oil, 33.2 mg. Yield 78%.

$^1$H-NMR(CDCl$_3$): 4.03 (2H, d, J=1.2 Hz), 4.62 (2H, s), 6.90 (1H, dd, J=7.8, 0.6 Hz), 7.25 (1H, t, J=7.8 Hz), 7.30 (1H, m), 7.44–7.61 (3H, m), 7.73 (1H, dd, J=7.8, 0.6 Hz), 7.88–7.93 (2H, m).

Example 24

2-Benzenesulfonyl-8-pyrrolidin-1-yl-2,7,8,9-tetrahydro-6-oxa-2-azabenzo[cd]azulene (36-1) ($R^4$=pyrrolidinyl)

A solution of pyrrolidine 35.4 mg in dry tetrahydrofuran 0.5 ml, sodium triacetoxyborohydride 133.7 mg and acetic acid 26 µl were added to a solution of compound (35) 135.9 mg in dry tetrahydrofuran 3.5 ml at room temperature and the mixture was stirred for 24 h. Water was added to the reaction mixture, which was made alkaline with an aqueous saturated sodium hydrogencarbonate solution and extracted with ethyl acetate. The extracts were washed with brine, dried over anhydrous magnesium sulfate and concentrated under reduced pressure. The residue obtained was chromatographed on aluminum oxide 20 g in chloroform to give the titled compound (36-1) as a brown oil, 97.7 mg. Yield 62%. This was treated with 1 eq. oxalic acid to give the salt which was recrystallized from ether-methanol to give colorless crystals, m.p. 170–173° C.(dec.).

$^1$H-NMR(CDCl$_3$): 1.76–1.84 (4H, m), 2.60–3.26 (7H, m), 4.12 (1H, dd, J=12.9, 6.3 Hz), 4.47 (1H, d, J=12.9 Hz), 6.73 (1H, dd, J=8.1, 0.9 Hz), 7.17 (1H, t, J=8.1 Hz), 7.33 (1H, s), 7.41–7.61 (4H, m), 7.86–7.90 (2H, m).

Following compounds were obtained, according to the similar treatment.

| Compd No | $R^4$ | m.p. (° C.) | $^1$H-NMR (CDCl$_3$) |
|---|---|---|---|
| 36-2 | NHMe | 208–213 (dec.) oxalate | 2.52 (3H, s), 2.91–3.15 (3H, m), 4.22–4.27 (2H, m), 6.76 (1H, dd, J=8.1, 0.9 Hz), 7.18 (1H, t, J=8.1 Hz), 7.32–7.34 (1H, m), 7.41–7.58 (3H, m), 7.61 (1H, dd, J=8.1, 0.9 Hz), 7.86–7.90 (2H, m) |
| 36-3 | NEt$_2$ | 106–108 | 1.07 (6H, t, J=6.9 Hz), 2.50–3.30 (7H, m), 3.98–4.05 (1H, m), 4.52 (1H, d, J=11.7 Hz), 6.74 (1H, dd, J=7.8, 0.9 Hz), 7.17 (1H, t, J=7.8 Hz), 7.33 (1H, s), 7.42–7.62 (4H, m), 7.86–7.90 (2H, m) |
| 36-4 | NHBn | 208–209 (dec.) oxalate | 2.94–3.11 (2H, m), 3.20–3.27 (1H, m), 3.86 (1H, d, J=13.2 Hz), 3.95 (1H, d, J=13.2 Hz), 4.27 (2H, d, J=3.9 Hz), 6.77 (1H, d, J=7.8 Hz), 7.15–7.62 (11H, m), 7.86–7.90 (2H, m) |

Example 25

2,7,8,9-Tetrahydro-6-oxa-2-azabenzo[cd]azulen-8-ol (37)

Compound (18-1) 374.4 mg was suspended in methanol 5 ml and sodium borohydride 75.7 mg was added to the suspension with cooling in ice. The mixture was stirred for 1 h. Water was added with cooling in ice. The mixture was extracted with ethyl acetate. The extracts were washed with brine, dried over anhydrous magnesium sulfate and concentrated under reduced pressure. The residue obtained was recrystallized from acetone-isopropanol to give the titled compound (37) as colorless crystals m.p. 169–170° C., 356.5 mg. Yield 94%.

$^1$H-NMR(CD$_3$OD): 2.83–2.93 (1H, m), 3.29–3.38 (1H, m), 4.03–4.17 (2H, m), 4.32 (1H, dd, J=5.4, 2.1 Hz), 6.42–6.48 (1H, m), 6.88–6.95 (1H, m), 6.99 (1H, br s).

Scheme of Reactions, Examples 26–34

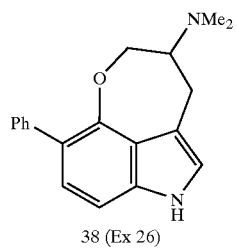
38 (Ex 26)

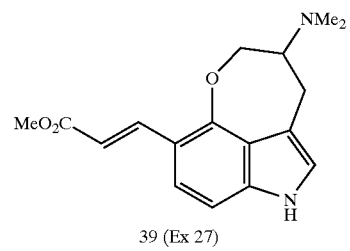
39 (Ex 27)

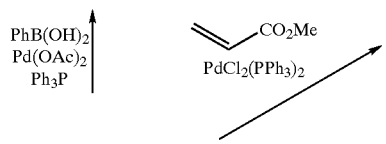

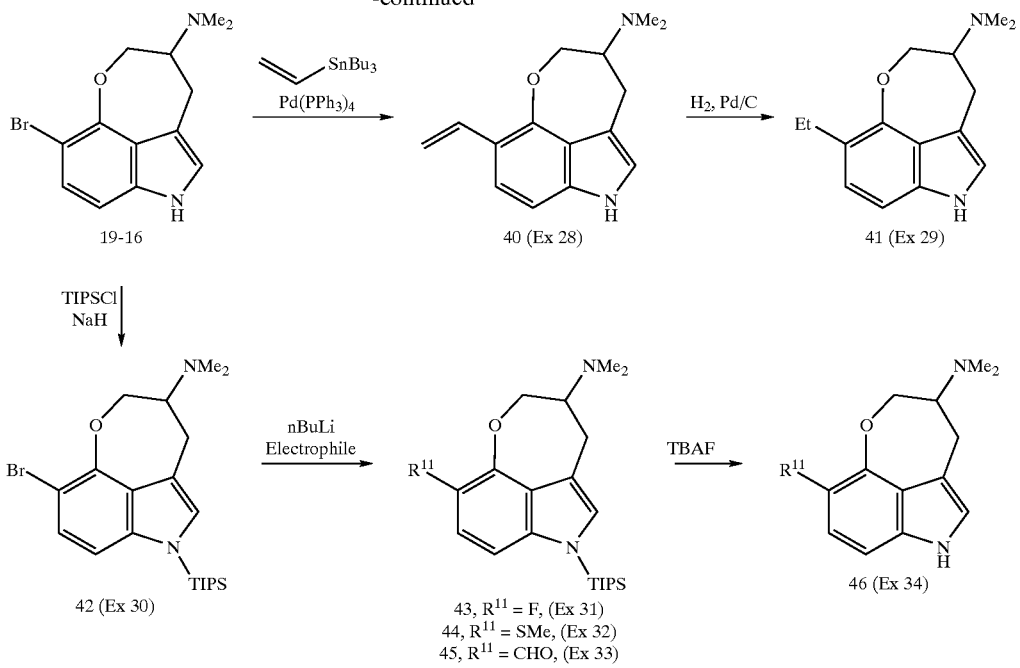

Example 26

Dimethyl-(5-phenyl-2,7,8,9-tetrahydro-6-oxa-2-azabenzo[cd]azulen-8-yl)amine (38)

Phenylboronic acid 190.1 mg, palladium acetate 13.0 mg, tris(2-methylphenyl)phosphine 30.9 mg and potassium carbonate 691.0 mg were added to a solution of compound (19-16) 296 mg in dry dimethylformamide 6 ml under nitrogen atmosphere. The mixture was heated at 120° C. for 2 h. After cooling, water was added. The mixture was extracted with ethyl acetate. The extracts were washed with brine, dried over anhydrous magnesium sulfate and concentrated under reduced pressure. The residue obtained was chromatographed on aluminum oxide in ethyl acetate:toluene (1:2) to give the titled compound (38) as colorless crystals, 33.0 mg. Yield 11%. Furthermore, the titled compound was recrystallized from acetone-isopropyl ether to give colorless crystals, m.p. 168–170° C.

$^1$H-NMR(CDCl$_3$): 2.42 (6H, s), 2.96–3.28 (3H, m), 4.17 (1H, dd, J=12.3, 6.3 Hz), 4.53 (1H, d, J=12.3 Hz), 7.02 (1H, s), 7.03 (1H, d, J=8.4 Hz), 7.15 (1H, d, J=8.4 Hz), 7.27–7.60 (5H, m).

Example 27

(E)-3-(8-Dimethylamino-2,7,8,9-tetrahydro-6-oxa-2-azabenzo[cd]azulen-5-yl)acrylic acid methyl ester (39)

Methyl acrylate 140 μl, triethylamine 217 μl and bis(triphenylphosphine)palladium dichloride 0.2 mg were added to a solution of compound (19-16) 306 mg in dry dimethylformamide 5 ml under nitrogen atmosphere. The mixture was heated at 100° C. for 19 h. Water was added with cooling in ice. The mixture was extracted with ethyl acetate. The extracts were washed with brine, dried over anhydrous magnesium sulfate and concentrated under reduced pressure. The residue obtained was chromatographed on aluminum oxide in ethyl acetate:hexane (1:1) to give the titled compound as yellow crystals 146.5 mg. Yield 47%. The titled compound was recrystallized from acetone-isopropyl ether to give pale yellow crystals, m.p. 168–170° C.

$^1$H-NMR(CDCl$_3$): 2.43 (6H, s), 2.90–3.22 (3H, m), 3.80 (3H, s), 4.24 (1H, dd, J=12.0, 6.6 Hz), 4.63 (1H, dd, J=12.6, 0.9 Hz), 6.39 (1H, d, J=16.2 Hz), 6.94 (1H, d, J=8.7 Hz), 6.97 (1H, m), 7.34 (1H, d, J=8.7 Hz), 8.22 (1H, br s), 8.25 (1H, d, J=16.2 Hz).

Example 28

Dimethyl-(5-vinyl-2,7,8,9-tetrahydro-6-oxa-2-azabenzo[cd]azulen-8-yl)amine (40)

Tri-n-butylvinyltin 952.0 mg, tetrakistriphenylphosphine-palladium 116.1 mg and lithium chloride 254.0 mg were added to a solution of compound (19-16) 592.2 mg in dry dimethylformamide 30 ml under a nitrogen atmosphere. The mixture was heated at 120° C. for 4 h and diluted with ethyl acetate, after cooling. The insoluble materials were removed by filtration through cerite. The filtrate was washed with an aqueous saturated sodium hydrogencarbonate solution and brine, dried over anhydrous magnesium sulfate and concentrated under reduced pressure. The residue obtained was chromatographed on aluminum oxide in ethyl acetate:toluene (1:2) to give a colorless oil 602.2 mg. This was chromatographed on silica gel in chloroform:methanol:aq. ammonia (46:10:1) to give a yellow oil 500 mg, which was crystallized from hexane giving the titled compound as colorless crystals, 324 mg. Yield 67%. Furthermore, the titled compound was recrystallized from ether-petroleumether to give colorless crystals, m.p.119–120° C.

$^1$H-NMR(CDCl$_3$): 2.43 (6H, s), 2.93–3.23 (3H, m), 4.12–4.19 (1H, m), 4.61 (1H, dd, J=12.6, 1.5 Hz), 5.13 (1H, dd, J=11.4, 1.5 Hz), 5.62 (1H, dd, J=18.0, 1.5 Hz), 6.91–6.96 (2H, m), 7.22 (1H, dd, J=18.0, 11.4 Hz), 7.34 (1H, d, J=8.4 Hz), 8.08 (1H, br s).

Example 29

(5-Ethyl-2,7,8,9-tetrahydro-6-oxa-2-azabenzo[cd]azulen-8-yl)dimethylamine (41)

Compound (40) 242 mg was dissolved in methanol 4 ml and 5% palladium/C 60 mg was added. A mixture was stirred in hydrogen atmosphere at room temperature for 3 h. The catalyst was filtered off and the filtrate was concentrated under reduced pressure. The residue obtained was chromatographed on aluminum oxide in ethyl acetate:hexane (1:2) to give the titled compound as colorless crystals 241.6 mg. Yield 99%. This was recrystallized from acetone-hexane to give the titled compound as colorless crystals, m.p. 91–92° C.

$^1$H-NMR(CDCl$_3$): 1.21 (3H, t, J=7.5 Hz), 2.44 (6H, s), 2.65–2.78 (2H, m), 2.94–3.23 (3H, m), 4.12–4.18 (1H, m), 4.54–4.59 (1H, m), 6.90 (1H, d, J=8.4 Hz), 6.94–6.96 (1H, m), 6.97 (1H, d, J=8.4 Hz), 7.96 (1H, br s).

Example 30

(5-Bromo-2-triisopropylsilanyl-2,7,8,9-tetrahydro-6-oxa-2-azabenzo[cd]azulen-8-yl)dimethylamine (42)

Compound (19-16) 2.00 g was added to a suspension of 60% sodium hydride 300.8 mg in tetrahydrofuran 30 ml with cooling in ice. The mixture was stirred for 1 h. Then, triisopropylsilyl chloride (TIPSCl) 1.6 ml was added with cooling in ice. The mixture was stirred for 4 h with cooling in ice. Water was added to reaction mixture with cooling in ice. The mixture was extracted with ethyl acetate. The extracts were washed with brine, dried over anhydrous magnesium sulfate and concentrated under reduced pressure. The residue obtained was chromatographed on aluminum oxide in ethyl acetate:hexane (1:4) to give a pale brown oil 2.67 g. This was recrystallized from isopropyl ether to give colorless crystals, m.p. 119–121° C. 1.85 g. Yield 60%.

$^1$H-NMR(CDCl$_3$): 1.13 (18H, dd, J=7.5, 0.9 Hz), 1.58–1.72 (3H, m), 2.45 (6H, s), 3.03–3.26 (3H, m), 4.18–4.24 (1H, m), 4.66 (1H, dd, J=12.3, 1.5 Hz), 6.96 (1H, d, J=8.7 Hz), 7.00 (1H, s), 7.20 (1H, d, J=8.7 Hz).

Example 31

(5-Fluoro-2-triisopropylsilanyl-2,7,8,9-tetrahydro-6-oxa-2-azabenzo[cd]azulen-8-yl)dimethylamine (43)

A solution of compound (42) 451 mg in dry tetrahydrofuran 5 ml was cooled at −70° C. n-BuLi (1.56 mol/l hexane solution) 1.3 ml was added dropwise to the mixture, which was stirred for 1 h. Then, N-fluorobenzenesulfonimide 694 mg was added and the mixture was stirred for 3.5 h. The reaction mixtures was diluted with an aqueous ammonium chloride solution, extracted with ethyl acetate. The extracts were washed with brine, dried over anhydrous magnesium sulfate and concentrated under reduced pressure. The residue obtained was chromatographed on aluminum oxide in ethyl acetate:hexane (1:5) to give a yellow oil. This was chromatographed on thin aluminum oxide plates (Merck precoated TLC plate alumina 60F254 in ethyl acetate:hexane (1:5)) to give the titled compound as a pale yellow oil, 100 mg.

$^1$H-NMR(CDCl$_3$): 1.28 (18H, dd, J=7.5, 0.9 Hz), 1.58–1.70 (3H, m), 2.45 (6H, s), 2.95–3.28 (3H, m), 4.20–4.26 (1H, m), 4.62 (1H, dd, J=11.7, 1.2 Hz), 6.86–6.97 (2H, m), 7.03 (1H, s).

Example 32

Dimethyl-(5-methylsulfanyl-2-triisopropylsilanyl-2,7,8,9-tetrahydro-6-oxa-2-azabenzo[cd]-azulen-8-yl) amine (44)

A solution of compound (42) 451 mg in dry tetrahydrofuran 5 ml was cooled at −70° C. n-BuLi (1.56 mol/l hexane solution) 1.3 ml was added dropwise to the solution and the mixture was stirred for 1 h. Then, dimethyldisulfide 185 μl was added and the mixture was stirred for 2 h. The reaction mixtures was diluted with an aqueous ammonium chloride solution and extracted with ethyl acetate. The extracts were washed with brine, dried over anhydrous magnesium sulfate and concentrated under reduced pressure. The residue obtained was chromatographed on aluminum oxide in ethyl acetate:hexane (1:5) to give the titled compound as colorless crystals, 289.8 mg. Yield 69%. This was recrystallized from hexane to give the titled compound as colorless crystals, m.p. 77–79° C.

$^1$H-NMR(CDCl$_3$): 1.13 (18H, d, J=7.5 Hz), 1.58–1.74 (3H, m), 2.45 (total 9H, each s), 2.97–3.30 (3H, m), 4.22 (1H, d, J=12.0, 6.3 Hz), 4.68 (1H, dd, J 12.0, 1.2 Hz), 6.99 (1H, s), 7.04 (1H, d, J=8.4 Hz), 7.10 (1H, d, J=8.7 Hz).

Example 33

8-Dimethylamino-2-triisopropylsilanyl-2,7,8,9-tetrahydro-6-oxa-2-azabenzo[cd]-azulene-5-carbaldehyde (45)

A solution of compound (42) 750 mg in dry tetrahydrofuran 7 ml was cooled at −70° C. and n-BuLi (1.56 mol/l hexane solution) 2.2 ml was added dropwise to the solution. The mixture was stirred for 1 h. Dimethylformamide 257 μl was added and the mixture was stirred for 2 h. The reaction mixtures was diluted with an aqueous ammonium chloride solution and extracted with ethyl acetate. The extracts were washed with brine, dried over anhydrous magnesium sulfate and concentrated under reduced pressure. The residue obtained was chromatographed on aluminum oxide in ethyl acetate:hexane (1:4) to give the titled compound as yellow oil, 556 mg. This was recrystallized from hexane to give the titled compound as colorless crystals, m.p. 104–106° C., 395 mg. Yield 59%

$^1$H-NMR(CDCl$_3$): 1.14 (18H, d, J=7.5 Hz), 1.55–1.72 (3H, m), 2.45 (6H, s), 2.97–3.30 (3H, m), 4.29 (1H, dd, J=12.6, 6.3 Hz), 4.65 (1H, d, J=12.6 Hz), 7.04 (1H, s), 7.07 (1H, d, J=9.0 Hz), 7.60 (1H, d, J=8.7 Hz), 10.50 (1H, s).

Example 34

8-Dimethylamino-2,7,8,9-tetrahydro-6-oxa-2-azabenzo[cd]-azulene-5-carbaldehyde (46-1)
(R$_{11}$=CHO)

Tetra-n-butylammoniumfluoride (1 mol/l tetrahydrofuran solution) 2.2 ml was added to compound (45) 496 mg in tetrahydrofuran 10 ml with cooling in ice. The mixture was stirred for 3 h, diluted with water and ethyl acetate and, extracted with ethyl acetate. The extracts were washed with brine, dried over anhydrous magnesium sulfate and concentrated under reduced pressure. The residue obtained was chromatographed on aluminum oxide in ethyl acetate:hexane (2:1) to give colorless crystals, 273.2 mg. This was recrystallized from acetone-isopropyl ether to give the titled compound as colorless crystals, m.p.175–176° C., 2654 mg. Yield 88%.

$^1$H-NMR(DMSO-d$_6$): 2.29 (6H, s), 2.78–3.13 (3H, m), 4.31 (1H, dd, J=12.3, 6.6 Hz), 4.58 (1H, d, J=12.3 Hz), 6.99 (1H, dd, J=8.4, 0.9 Hz), 7.23 (1H, s), 7.40 (1H, d, J=8.4 Hz), 10.36 (1H, d, J=0.9 Hz), 11.48 (1H, br s).

Following compounds were obtained, according to the similar treatment.

| Compd No | R[11] | m.p. (° C.) | $^1$H-NMR (CDCl$_3$) |
|---|---|---|---|
| 46-2 | F | 148–150 | 2.44 (6H, s), 2.93–3.25 (3H, m), 4.24 (1H, dd, J=12.3, 6.6 Hz), 4.63 (1H, dd, J=12.3, 1.2 Hz), 6.83 (1H, dd, J=8.7, 3.6 Hz), 6.97 (1H, dd, J=11.4, 8.7 Hz), 7.01 (1H, m), 8.04 (1H, br s) |
| 46-3 | SMe | 112–113 | 2.44 (3H, s), 2.44 (6H, s), 2.97–3.24 (3H, m), 4.24 (1H, dd, J=12.3, 6.3 Hz), 4.69 (1H, dd, J=12.3, 2.1 Hz), 6.94 (1H, d, J=8.4 Hz), 6.97–6.99 (1H, m), 7.19 (1H, d, J=8.7 Hz), 8.09 (1H, br s) |

Scheme of Reactions, Examples 35–37

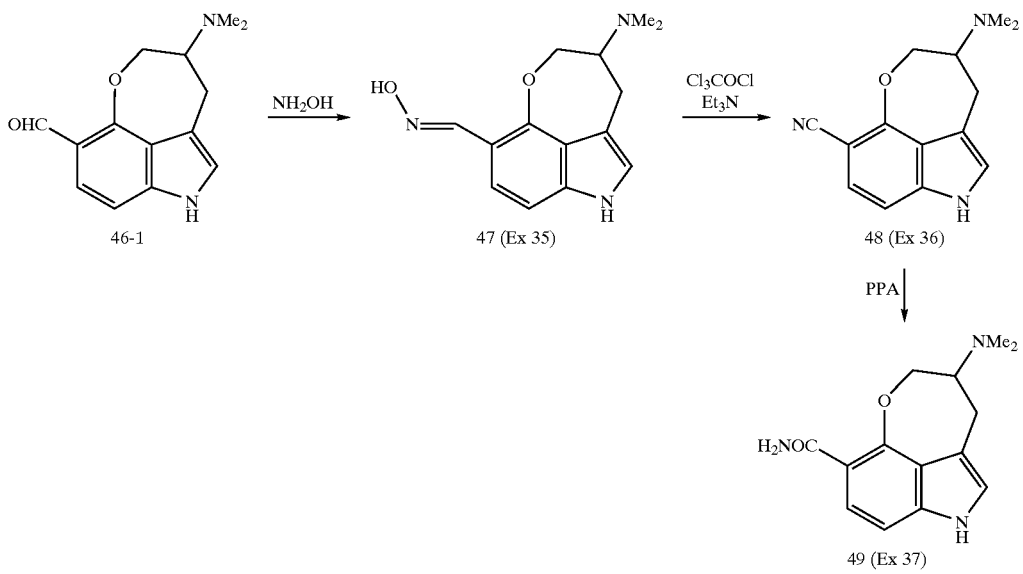

Example 35

8-Dimethylamino-2,7,8,9-tetrahydro-6-oxa-2-azabenzo[cd]-azulene-5-carbaldehyde Oxime (47)

Hydroxylamine hydrogenchloride 83.4 mg and sodium acetate 98.4 mg were added to a suspension of compound (46-1) 244 mg in 95% ethanol 10 ml. The mixture was stirred at room temperature for 2 h and concentrated under reduced pressure. Water was added to the residue, which was made alkaline with an aqueous saturated sodium hydrogencarbonate solution. Colorless precipitates appeared and were collected by filtration, washed with methanol-ethyl acetate to give the titled compound as colorless crystals, m.p. 230–235° C.(dec.), 228 mg. Yield 88%.

$^1$H-NMR(DMSO-d$_6$): 2.28 (6H, s), 2.73–3.12 (3H, m), 4.15 (1H, dd, J=12.0, 6.6 Hz), 4.49 (1H, d, J=12.3 Hz), 6.93 (1H, d, J=7.8 Hz), 7.13 (1H, br d, J=2.7 Hz), 7.38 (1H, d, J=8.7 Hz), 8.39 (1H, s), 10.66 (1H, s), 11.12 (1H, br s).

Example 36

8-Dimethylamino-2,7,8,9-tetrahydro-6-oxa-2-azabenzo[cd]-azulene-5-carbonitrile (48)

Triethylamine 33 μl and trichloroacetyl chloride 13 μl were added to a solution of compound (47) 28.9 mg in dichloromethane 2 ml with cooling ice and the mixture was stirred with cooling in ice and at room temperature for 18 h. A saturated sodium hydrogencarbonate solution was added thereto for alkalinization. The mixture was extracted with chloroform. The extracts were washed with brine, dried over anhydrous magnesium sulfate and concentrated under reduced pressure. The residue obtained was chromatographed on aluminum oxide in chloroform:methanol (97:3) to give the titled compound 26.3 mg as colorless crystals. Yield 98%. Furthermore, the titled compound was recrystallized from methanol-isopropyl ether to give colorless crystals, m.p. 205–207° C.

$^1$H-NMR(CD$_3$OD): 2.41 (6H, s), 2.89–3.23 (3H, m), 4.39 (1H, dd, J=12.6, 6.9 Hz), 4.64 (1H, d, J=12.6 Hz), 7.03 (1H, d, J=8.7 Hz), 7.17 (1H, d, J=8.7 Hz), 7.18 (1H, m).

Example 37

8-Dimethylamino-2,7,8,9-tetrahydro-6-oxa-2-azabenzo [cd]azulene-5-carboxylic acid amide (49)

Polyphophoric acid 420 mg was added to compound (48) 31.6 mg under an argon atmosphere and the mixture was heated at 90° C. for 6 h. Ice-water was added to the reaction mixture, which was made alkaline with an aqueous 5 N-sodium hydroxide solution and extracted with chloroform. The extracts were washed with brine, dried over anhydrous magnesium sulfate and concentrated under reduced pressure. The residue obtained was chromatographed on aluminum oxide in chloroform:methanol (97:3) to give the titled compound as colorless crystals, 20.9 mg. Yield 62%. Furthermore, the titled compound was recrystallized from acetone-isopropyl ether to give colorless crystals, m.p. 182–183° C.

$^1$H-NMR(DMSO-d$_6$): 2.29 (6H, s), 2.76–3.13 (3H, m), 4.24 (1H, dd, J=12.0, 6.0 Hz), 4.64 (1H, d, J=12.3 Hz), 6.97 (1H, d, J=8.7 Hz), 7.18 (1H, d, J=2.1 Hz), 7.22 (1H, br s), 7.66 (1H, d, J=8.7 Hz), 7.68(1H, br s), 11.20 (1H, br s)

Scheme of Reactions, Examples 38–40

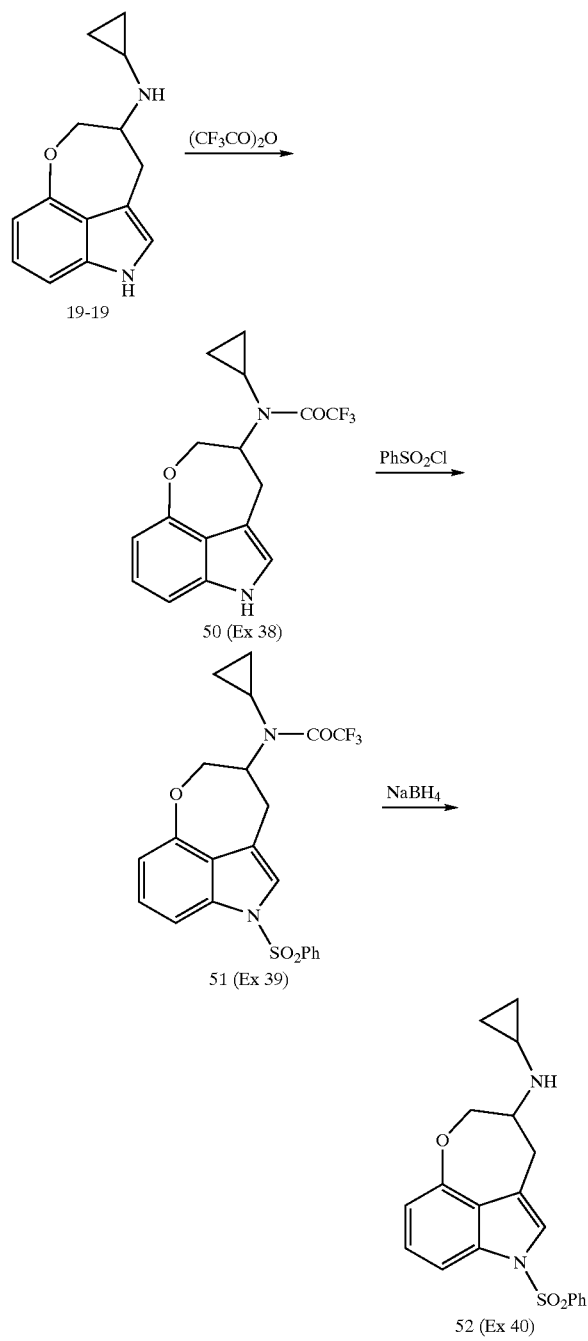

Example 38

N-Cyclopropyl-2,2,2-trifluoromethyl-N-(2,7,8,9-tetrahydro-6-oxa-2-azabenzo[cd]azulen-8-yl)acetamide (50)

Compound (19-19) 355 mg was dissolved in dry tetrahydrofuran 11 ml. A solution of triethylamine 178 mg and trifluoroacetic anhydride 344 mg in dry tetrahydrofuran 0.5 ml was added to the solution with cooling in ice. The mixture was stirred with cooling in ice for 2 h. Triethylamine 78 mg and trifluoroacetic anhydride 156 mg in dry tetrahydrofuran 0.2 ml were again added. The mixture was stirred with cooling in ice for 2 h and concentrated under reduced pressure. Water was added to the residue, which was extracted with ether. The extracts were washed with brine, dried over anhydrous magnesium sulfate and concentrated under reduced pressure. The residue obtained was chromatographed on aluminum oxide 15 g in chloroform:hexane (4:1) to give the titled compound as pale yellow crystals, 415 mg (yield 82%), m.p. 49–53° C.

$^1$H-NMR(CDCl$_3$): 0.94–1.06 (4H, m), 3.04–3.14 (2H, m), 3.64–3.74 (1H, m), 4.10–4.15 (1H, m), 4.46 (1H, dd, J=12.6, 1.8 Hz), 4.70 (1H, dd, J=12.6, 6.6 Hz), 6.64 (1H, dd, J=7.5, 1.2 Hz), 6.97 (1H, s), 7.00 (1H, dd, J=8.1, 1.2 Hz), 7.08 (1H, d, J=8.1 Hz), 8.17 (1H, br s)

Example 39

N-(2-Benzenesulfonyl-2,7,8,9-tetrahydro-6-oxo-2-aza-benzo[cd]azulen-8-yl)-N-cyclopropyl-2,2,2,-trifluoroacetamide (51)

60% Sodium hydride 56 mg was added to a solution of compound (50) 324 mg in dimethylformamide 12 ml with cooling in ice and the mixture was stirred at room for 1 h. Benzenesulfonyl chloride 238 mg was added dropwise with cooling in ice and then, the mixture was stirred at 40° C. for 21 h. Ice-water and then an aqueous sodium hydrogencarbonate solution were added to the reaction mixture, which was extracted with ethyl acetate. The extracts were washed with brine, dried over anhydrous magnesium sulfate and concentrated under reduced pressure. The residue obtained was chromatographed on aluminum oxide in chloroform:hexane (1:2) to give the titled compound as a colorless oil, 130 mg (yield 28%).

$^1$H-NMR(CDCl$_3$): 0.88–1.05 (4H, m), 3.03–3.09 (2H, m), 3.58–3.68 (1H, m), 3.99–4.06 (1H, m), 4.40 (1H, dd, J=12.9, 1.5 Hz), 4.59 (1H, dd, J=12.9, 6.3 Hz), 6.77 (1H, dd, J=7.8, 0.6 Hz), 7.20 (1H, t, J=8.1 Hz), 7.34 (1H, s), 7.44–7.66 (4H, m), 7.86–7.90 (2H, m)

Example 40

(2-Benzenesulfonyl-2,7,8,9-tetrahydro-6-oxo-2-aza-benzo[cd]azulen-8-yl)cyclopropylamine (52)

Compound (51) 129 mg was dissolved in ethanol 3 ml. Sodium hydrogenborohydride 42 mg was added to the solution at room temperature and the mixture was stirred for 23 h. Water was added with cooling in ice to the reaction mixture, which was extracted with chloroform. The extracts were washed with brine, dried over anhydrous magnesium sulfate and concentrated under reduced pressure. The residue obtained was chromatographed on aluminum oxide in chloroform:hexane (1:1) to give the titled compound as a colorless oil, 98 mg. Yield 96%. The titled compound was treated with 1 eq. of oxalic acid to give the salt, which was recrystallized from isopropanol-ether to give colorless crystals, m.p. 119–122° C. (dec.).

$^1$H-NMR(CDCl$_3$): 0.30–0.49 (4H, m), 2.21–2.27 (1H, m), 2.94–3.12 (2H, m), 3.31–3.37 (1H, m), 4.29–4.31 (2H, m), 6.77 (1H, d, J=7.8 Hz), 7.19 (1H, t, J=8.1 Hz), 7.33 (1H, s), 7.42–7.63 (4H, m), 7.86–7.90 (2H, m)

Scheme of Reactions, Examples 41–44

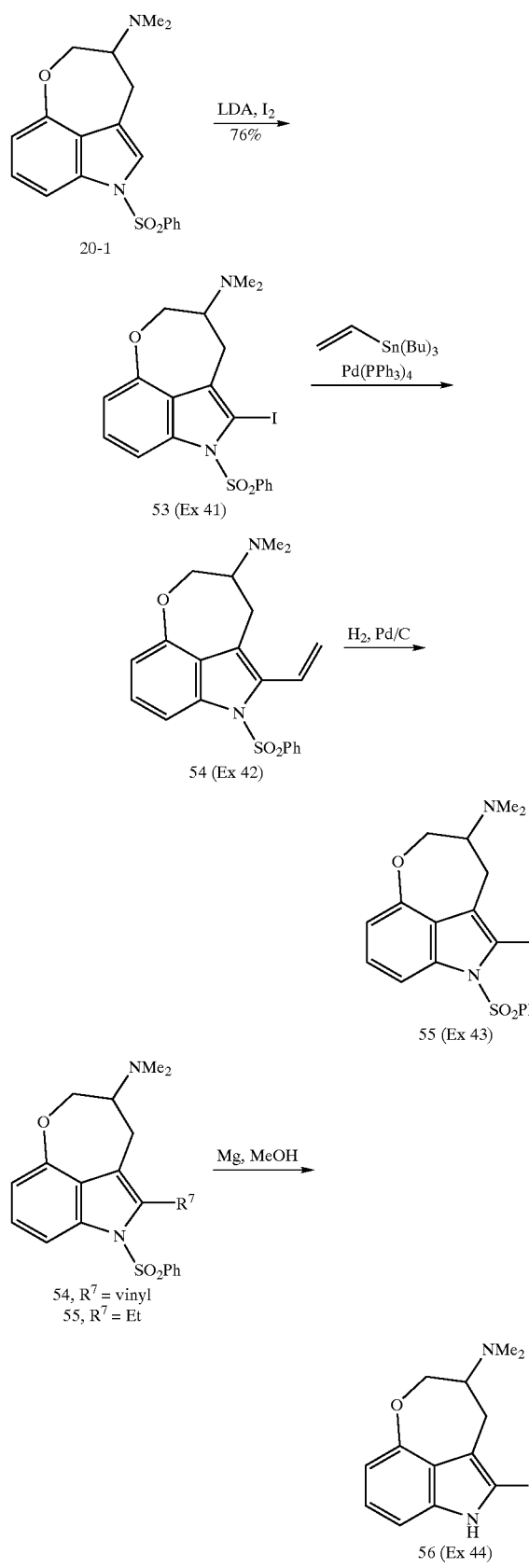

Example 41

(2-Benzenesulfonyl-1-iodo-2,7,8,9-tetrahydro-6-oxa-2-azabenzo[cd]azulen-8-yl)dimethylamine (53)

LDA was prepared by addition of n-BuLi (1.56 mol/l hexane solution) 1.08 ml to a solution of diisopropylamine 255 μl in dry tetrahydrofuran 3 ml at −70° C. Then, a solution of compound (20-1) 500 mg in dry tetrahydrofuran 2 ml was added at that temperature to the mixture, which was stirred for 2 h. Then, a solution of iodine 426 mg in dry tetrahydrofuran 2 ml was added and the mixture was stirred for 2 h. Ice was added to the reaction mixtures, which was extracted with chloroform. The extracts were washed with brine, dried over anhydrous magnesium sulfate and concentrated under reduced pressure. The residue obtained was chromatographed on aluminum oxide in ethyl acetate:hexane (1:5) to give the titled compound as colorless crystals 514 mg. Yield 76%. This was recrystallized from from acetone-isopropyl ether to give colorless crystals, m.p. 136–137° C.

$^1$H-NMR(CDCl$_3$): 2.36 (6H, s), 2.87–2.97 (3H, m), 4.08–4.14 (1H, m), 4.41 (1H, d, J=12.6 Hz), 6.75 (1H, d, J=7.5 Hz), 7.40–7.45 (2H, m), 7.53–7.58 (1H, m), 7.86–7.90 (2H, m), 7.96 (1H, d, J=7.8 Hz).

Example 42

(2-Benzenesulfonyl-1-vinyl-2,7,8,9-tetrahydro-6-oxa-2-azabenzo[cd]azulen-8-yl)dimethylamine (54)

Tri-n-butyl(vinyl)tin 484.4 mg, tetrakis(triphenylphosphine)palladium 690 mg and lithium chloride 127.7 mg were added to a solution of compound (53) 491 mg in dry dimethylformamide 10 ml under nitrogen atmosphere. The mixture was heated at 100° C. for 3 h, diluted with ethyl acetate after cooling and filtered through cerite to remove the insoluble materials. The filtrate was washed with an aqueous saturated sodium hydrogencarbonate solution and brine, dried over anhydrous magnesium sulfate and concentrated under reduced pressure. The residue obtained was pulverized in hexane, collected by filtration and chromatographed on aluminum oxide in chloroform:hexane (1:1) to give the titled compound as colorless crystals 602.2 mg. Yield 79%. Furthermore, the titled compound was recrystallized from acetone-isopropyl ether to give colorless crystals, m.p. 133–134° C.

$^1$H-NMR(CDCl$_3$): 2.53 (6H, s), 2.78–3.10 (3H, m), 4.11 (1H, dd, J=12.6, 6.6 Hz), 4.41 (1H, d, J=12.6 Hz), 5.36 (1H, dd, J=17.7, 1.5 Hz), 5.69 (1H, dd, J=11.4, 1.5 Hz), 6.77 (1H, dd, J=8.1, 0.9 Hz), 7.18 (1H, dd, J=18.0, 11.4 Hz), 7.19 (1H, t, J=8.1 Hz), 7.34–7.53 (3H, m), 7.73–7.76 (2H, m), 7.87 (1H, dd, J=8.4, 0.9 Hz).

Example 43

(2-Benzenesulfonyl-1-ethyl-2,7,8,9-tetrahydro-6-oxa-2-azabenzo[cd]azulen-8-yl)dimethylamine (55)

Compound (54) 200.1 mg was dissolved in a mixture of methanol 8 ml and tetrahydrofuran 4 ml. 10% Pd/C 49.8 mg was added. The mixture was stirred under hydrogen atmosphere for 18 h at room temperature. The catalyst was filtered off and the filtrate was concentrated under reduced pressure. The residue obtained was chromatographed on aluminum oxide in chloroform:hexane (1:1) to give the titled compound as a colorless oil 198 mg. Yield 98%. This was treated with 1 eq. of oxalic acid to give the salt, which was recrystallized from ether-methanol to give colorless crystals, m.p. 193–194° C.(dec.).

¹H-NMR(CDCl₃): 1.28 (3H, t, J=7.5 Hz), 2.41 (6H, s), 2.89–3.07 (5H, m), 4.07–4.13 (1H, m), 4.43 (1H, d, J=12.6 Hz), 6.75 (1H, dd, J=7.8, 0.9 Hz), 7.13 (1H, t, J=8.1 Hz), 7.37–7.43 (2H, m), 7.49–7.54 (1H, m), 7.71–7.75 (2H, m), 7.83 (1H, dd, J=8.1, 0.9 Hz).

Example 44

(1-Ethyl-2,7,8,9-tetrahydro-6-oxa-2-azabenzo[cd]azulen-8-yl)dimethylamine (56-1)

Magnesium (turning) 246 mg was added to compound (55) in methanol 9 ml and the mixture was stirred at room temperature for 3 h. Ice was added to the reaction mixture which was diluted with chloroform. The insoluble materials were filtered off through cerite and the filtrate was extracted with chloroform. The extracts were washed with brine, dried over anhydrous magnesium sulfate and concentrated under reduced pressure. The residue obtained was chromatographed on aluminum oxide in chloroform:hexane (2:1) to give the titled compound as a pale yellow oil 97.8 mg. Yield 79%. This was treated with 1 eq. oxalic acid to give the salt, which was recrystallized from ether-methanol to give colorless crystals, m.p. 236–237° C. (dec.).

¹H-NMR(CDCl₃): 1.29 (3H, t, J=7.5 Hz), 2.45 (6H, s), 2.75 (2H, q, J=7.5 Hz), 2.86–3.13 (3H, m), 4.12 (1H, dd, J=12.3, 6.3 Hz), 4.54 (1H, d, J=12.3 Hz), 6.59 (1H, dd, J=7.5, 0.9 Hz), 6.91 (1H, dd, J=8.1, 0.9 Hz), 6.99 (1H, t, J=7.8 Hz), 7.90 (1H, br s).

Following compounds were obtained, according to the similar treatment.

| Compd No | R⁷ | m.p. | ¹H-NMR (CDCl₃) |
|---|---|---|---|
| 56-2 | vinyl | 195–198 (dec.) oxalate | 2.43 (6H, s), 2.64–3.25 (3H, m), 4.12 (1H, dd, J=12.0, 6.3 Hz), 4.54 (1H, dd, J=12.0, 2.1 Hz), 5.27 (1H, d, J=11.4 Hz), 5.43 (1H, d, J=11.4 Hz), 6.58 (1H, dd, J=7.8, 0.9 Hz), 6.79 (1H, dd, J=17.7, 11.4 Hz), 6.91 (1H, dd, J=8.1, 0.9 Hz), 7.06 (1H, t, J=8.1 Hz), 8.11 (1H, br s), |

Example 45

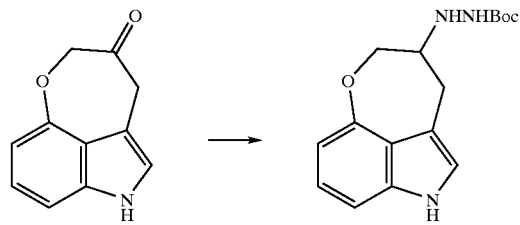

18-1 → 57 (Ex 45)

N-(2,7,8,9-Tetrahydro-6-oxo-2-azabenzo[cd]azulen-8-yl)hydrazinecarboxylic acid tert-butyl ester (57)

t-Butylbuthoxycarbonyl hydrazide 139 mg was added to a solution of compound (18-1) 170 mg in dry tetrahydrofuran 6 ml. The mixture was stirred at room temperature for 4 h and concentrated under reduced pressure. Trifluoroacetic acid 0.7 ml and triethylsilane 212 mg were added to the residue. The mixture was stirred for 80 min. 1N-HCl and then potassium hydroxide pellets were added to the reaction mixture with cooling in ice to alkaline. The mixture was extracted with chloroform. The organic layer was washed with brine, dried over anhydrous magnesium sulfate and concentrated under reduced pressure. The residue obtained was chromatographed on aluminum oxide in chloroform:hexane (4:1) to give the titled compound as crystals, 158 mg (yield 58%). The crude crystalline materials were recrystallized from hexane-ethyl acetate to give pale yellow crystals, m.p. 171–173° C.(dec.).

¹H-NMR(CDCl₃): 1.46 (9H, s), 2.84–2.93 (1H, m), 3.17–3.24 (2H, m), 3.59–3.66 (1H, m), 4.23 (1H, dd, J=12.3, 7.2 Hz), 4.37 (1H, d, J=12.3 Hz), 6.21 (1H, br s), 6.61 (1H, d, J=7.5 Hz), 6.96–7.08 (3H, m), 8.11 (1H, br s)

Example A

As examples of a compound (I), compounds (I-a) and compounds (I-b) shown in Table 7–28 and Table 29–42, respectively.

TABLE 7

(I-a)

| Compd No | R⁴ | R⁷ | R⁸ |
|---|---|---|---|
| 1 | COOH | H | H |
| 2 | COOMe | H | H |
| 3 | COOEt | H | H |
| 4 | COO-tBu | H | H |
| 5 | CONH₂ | H | H |
| 6 | CONHMe | H | H |
| 7 | CONHEt | H | H |
| 8 | CONH-nPr | H | H |
| 9 | CONMe₂ | H | H |
| 10 | CONEt₂ | H | H |
| 11 | CON(nPr)₂ | H | H |
| 12 | CONHPh | H | H |
| 13 | (C(=O)-pyrrolidinyl) | H | H |
| 14 | (C(=O)-piperidinyl) | H | H |
| 15 | (C(=O)-azepanyl) | H | H |
| 16 | NH₂ | H | H |
| 17 | NHMe | H | H |
| 18 | NHEt | H | H |
| 19 | NH-nPr | H | H |
| 20 | NMe₂ | H | H |

TABLE 7-continued (I-a) Structure with R⁴ on oxepine ring fused to indole with R⁷ and R⁸ (on N).

| Compd No | R⁴ | R⁷ | R⁸ |
|---|---|---|---|
| 21 | NEt₂ | H | H |
| 22 | N(nPr)₂ | H | H |
| 23 | pyrrolidin-1-yl | H | H |
| 24 | piperidin-1-yl | H | H |
| 25 | azepan-1-yl (hexamethyleneimino) | H | H |
| 26 | NHCOMe | H | H |
| 27 | NHCOEt | H | H |

TABLE 8

| Compd No | R⁴ | R⁷ | R⁸ |
|---|---|---|---|
| 1 | NHCO-nPr | H | H |
| 2 | NHCOPh | H | H |
| 3 | NMeCOMe | H | H |
| 4 | N(nPr)COMe | H | H |
| 5 | NMeCOPh | H | H |
| 6 | N(nPr)COPh | H | H |
| 7 | NHCOOMe | H | H |
| 8 | NHCOOEt | H | H |
| 9 | NHCOO-tBu | H | H |
| 10 | NHCOOCH₂Ph | H | H |
| 11 | NMeCOOMe | H | H |
| 12 | N(nPr)COOMe | H | H |
| 13 | NMeCOOOH₂Ph | H | H |
| 14 | N(nPr)COOCH₂Ph | H | H |
| 15 | NHSO₂Me | H | H |
| 16 | NHSO₂Et | H | H |
| 17 | NHSO₂Ph | H | H |
| 18 | NHTs | H | H |
| 19 | NMeSO₂Me | H | H |
| 20 | N(nPr)SO₂Me | H | H |
| 21 | NMeSO₂Ph | H | H |
| 22 | N(nPr)SO₂Ph | H | H |
| 23 | COOH | Me | H |
| 24 | COOMe | Me | H |
| 25 | COOEt | Et | H |
| 26 | COO-tBu | nPr | H |
| 27 | CONH₂ | Me | H |
| 28 | CONHMe | Me | H |
| 29 | CONHEt | Et | H |
| 30 | CONH-nPr | nPr | H |
| 31 | CONMe₂ | Me | H |
| 32 | CONEt₂ | Et | H |
| 33 | CON(nPr)₂ | nPr | H |
| 34 | CONHPh | Me | H |
| 35 | CO-pyrrolidin-1-yl | Me | H |
| 36 | CO-piperidin-1-yl | Et | H |
| 37 | CO-azepan-1-yl | nPr | H |
| 38 | NH₂ | Me | H |
| 39 | NHMe | Me | H |
| 40 | NHEt | Et | H |

TABLE 9

| Compd No | R⁴ | R⁷ | R⁸ |
|---|---|---|---|
| 1 | NH-nPr | nPr | H |
| 2 | NMe₂ | Me | H |
| 3 | NEt₂ | Et | H |
| 4 | N(nPr)₂ | nPr | H |
| 5 | pyrrolidin-1-yl | Me | H |
| 6 | piperidin-1-yl | Et | H |
| 7 | azepan-1-yl | nPr | H |
| 8 | NHCOMe | Me | H |
| 9 | NHCOEt | Et | H |
| 10 | NHCO-nPr | nPr | H |
| 11 | NHCOPh | Me | H |
| 12 | NMeCOMe | Me | H |
| 13 | N(nPr)COMe | Et | H |
| 14 | NMeCOPh | nPr | H |
| 15 | N(nPr)COPh | Me | H |
| 16 | NHCOOMe | Me | H |
| 17 | NHCOOEt | Et | H |
| 18 | NHCOO-tBu | nPr | H |
| 19 | NHCOOCH₂Ph | Me | H |
| 20 | NMeCOOMe | nPr | H |
| 21 | N(nPr)COOMe | nPr | H |
| 22 | NMeCOOCH₂Ph | Me | H |
| 23 | N(nPr)COOCH₂Ph | nPr | H |
| 24 | NHSO₂Me | Me | H |
| 25 | NHSO₂Et | Et | H |
| 26 | NHSO₂Ph | nPr | H |
| 27 | NHTs | Et | H |
| 28 | NMeSO₂Me | Me | H |
| 29 | N(nPr)SO₂Me | nPr | H |

TABLE 9-continued

| Compd No | R⁴ | R⁷ | R⁸ |
|---|---|---|---|
| 30 | NMeSO₂Ph | Me | H |
| 31 | N(nPr)SO₂Ph | Me | H |
| 32 | COOH | Br | H |
| 33 | COOMe | Br | H |
| 34 | COOEt | CN | H |
| 35 | COO-tBu | Br | H |
| 36 | CONH₂ | Br | H |
| 37 | CONHMe | Br | H |
| 38 | CONHEt | CN | H |
| 39 | CONHn-Pr | Br | H |
| 40 | CONMe₂ | Br | H |
| 41 | CONEt₂ | CN | H |
| 42 | CON(nPr)₂ | Br | H |

TABLE 10

| Compd No | R⁴ | R⁷ | R⁸ |
|---|---|---|---|
| 1 | CONHPh | CN | H |
| 2 | 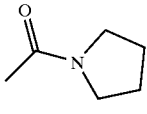 | Br | H |
| 3 | 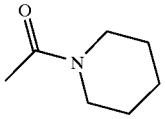 | Br | H |
| 4 | 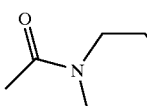 | CN | H |
| 5 | NH₂ | Br | H |
| 6 | NHMe | Br | H |
| 7 | NHEt | CN | H |
| 8 | NH-nPr | Br | H |
| 9 | NMe₂ | Br | H |
| 10 | NEt₂ | CN | H |
| 11 | N(nPr)₂ | Br | H |
| 12 | 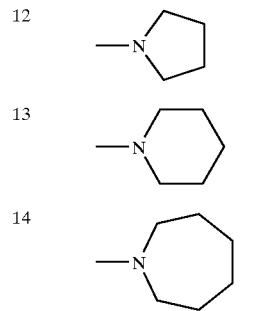 | Br | H |
| 13 | 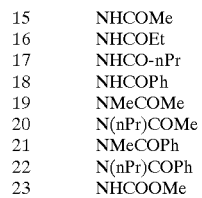 | CN | H |
| 14 | 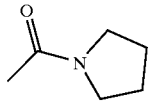 | Br | H |
| 15 | NHCOMe | Br | H |
| 16 | NHCOEt | Br | H |
| 17 | NHCO-nPr | CN | H |
| 18 | NHCOPh | Br | H |
| 19 | NMeCOMe | Br | H |
| 20 | N(nPr)COMe | Br | H |
| 21 | NMeCOPh | CN | H |
| 22 | N(nPr)COPh | Br | H |
| 23 | NHCOOMe | Br | H |

TABLE 10-continued

| Compd No | R⁴ | R⁷ | R⁸ |
|---|---|---|---|
| 24 | NHCOOEt | CN | H |
| 25 | NHCOO-tBu | Br | H |
| 26 | NHCOOCH₂Ph | Br | H |
| 27 | NMeCOOMe | CN | H |
| 28 | N(nPr)COOMe | Br | H |
| 29 | NMeCOOCH₂Ph | Br | H |
| 30 | N(nPr)COOCH₂Ph | CN | H |
| 31 | NHSO₂Me | Br | H |
| 32 | NHSO₂Et | Br | H |
| 33 | NHSO₂Ph | Br | H |
| 34 | NHTs | CN | H |
| 35 | NMeSO₂Me | Br | H |
| 36 | N(nPr)SO₂Me | Br | H |
| 37 | NMeSO₂Ph | Br | H |
| 38 | N(nPr)SO₂Ph | CN | H |
| 39 | COOH | Ph | H |

TABLE 11

| Compd No | R⁴ | R⁷ | R⁸ |
|---|---|---|---|
| 1 | COOMe | Ph | H |
| 2 | COOEt | Ph | H |
| 3 | COO-tBu | Ph | H |
| 4 | CONH₂ | Ph | H |
| 5 | CONHMe | Ph | H |
| 6 | CONHEt | Ph | H |
| 7 | CONH-nPr | Ph | H |
| 8 | CONMe₂ | Ph | H |
| 9 | CONEt₂ | Ph | H |
| 10 | CON(nPr)₂ | Ph | H |
| 11 | CONHPh | Ph | H |
| 12 | 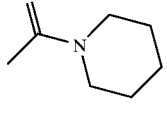 | Ph | H |
| 13 | 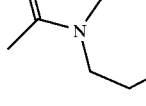 | Ph | H |
| 14 |  | Ph | H |
| 15 | NH₂ | Ph | H |
| 16 | NHMe | Ph | H |
| 17 | NHEt | Ph | H |
| 18 | NH-nPr | Ph | H |
| 19 | NMe₂ | Ph | H |
| 20 | NEt₂ | Ph | H |
| 21 | N(nPr)₂ | Ph | H |
| 22 | 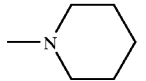 | Ph | H |
| 23 | 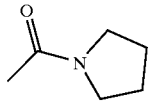 | Ph | H |

TABLE 11-continued

| Compd No | R⁴ | R⁷ | R⁸ |
|---|---|---|---|
| 24 | 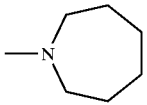 | Ph | H |
| 25 | NHCOMe | Ph | H |
| 26 | NHCOEt | Ph | H |
| 27 | NHCO-nPr | Ph | H |
| 28 | NHCOPh | Ph | H |
| 29 | NMeCOMe | Ph | H |
| 30 | N(nPr)COMe | Ph | H |
| 31 | NMeCOPh | Ph | H |
| 32 | N(nPr)COPh | Ph | H |
| 33 | NHCOOMe | Ph | H |
| 34 | NHCOOEt | Ph | H |
| 35 | NHCOO-tBu | Ph | H |
| 36 | NHCOOCH₂Ph | Ph | H |
| 37 | NMeCOOMe | Ph | H |
| 38 | N(nPr)COOMe | Ph | H |

TABLE 12

| Compd No | R⁴ | R⁷ | R⁸ |
|---|---|---|---|
| 1 | NMeCOOCH₂Ph | Ph | H |
| 2 | N(nPr)COOCH₂Ph | Ph | H |
| 3 | NHSO₂Me | Ph | H |
| 4 | NHSO₂Et | Ph | H |
| 5 | NHSO₂Ph | Ph | H |
| 6 | NHTs | Ph | H |
| 7 | NMeSO₂Me | Ph | H |
| 8 | N(nPr)SO₂Me | Ph | H |
| 9 | NMeSO₂Ph | Ph | H |
| 10 | N(nPr)SO₂Ph | Ph | H |
| 11 | COOH | H | Me |
| 12 | COOMe | H | Me |
| 13 | COOEt | H | Me |
| 14 | COO-tBu | H | Me |
| 15 | CONH₂ | H | Me |
| 16 | CONHMe | H | Me |
| 17 | CONHEt | H | Me |
| 18 | CONHn-Pr | H | Me |
| 19 | CONMe₂ | H | Me |
| 20 | CONEt₂ | H | Me |
| 21 | CON(nPr)₂ | H | Me |
| 22 | CONHPh | H | Me |
| 23 |  | H | Me |
| 24 | 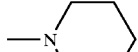 | H | Me |
| 25 | 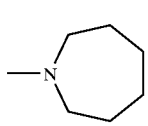 | H | Me |
| 26 | NH₂ | H | Me |
| 27 | NHMe | H | Me |
| 28 | NHEt | H | Me |
| 29 | NH-nPr | H | Me |
| 30 | NMe₂ | H | Me |

TABLE 12-continued

| Compd No | R⁴ | R⁷ | R⁸ |
|---|---|---|---|
| 31 | NEt₂ | H | Me |
| 32 | N(nPr)₂ | H | Me |
| 33 | 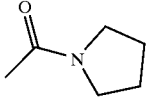 | H | Me |
| 34 | 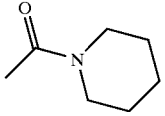 | H | Me |
| 35 | 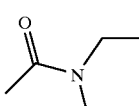 | H | Me |
| 36 | NHCOMe | H | Me |
| 37 | NHCOEt | H | Me |

TABLE 13

| Compd No | R4 | R7 | R8 |
|---|---|---|---|
| 1 | NHCO-nPr | H | Me |
| 2 | NHCOPh | H | Me |
| 3 | NMeCOMe | H | Me |
| 4 | N(nPr)COMe | H | Me |
| 5 | NMeCOPh | H | Me |
| 6 | N(nPr)COPh | H | Me |
| 7 | NHCOOMe | H | Me |
| 8 | NHCOOEt | H | Me |
| 9 | NHCOO-tBu | H | Me |
| 10 | NHCOOCH₂Ph | H | Me |
| 11 | NMeCOOMe | H | Me |
| 12 | N(nPr)COOMe | H | Me |
| 13 | NMeCOOCH₂Ph | H | Me |
| 14 | N(nPr)COOCH₂Ph | H | Me |
| 15 | NHSO₂Me | H | Me |
| 16 | NHSO₂Et | H | Me |
| 17 | NHSO₂Ph | H | Me |
| 18 | NHTs | H | Me |
| 19 | NMeSO₂Me | H | Me |
| 20 | N(nPr)SO₂Me | H | Me |
| 21 | NMeSO₂Ph | H | Me |
| 22 | N(nPr)SO₂Ph | H | Me |
| 23 | COOH | Me | Me |
| 24 | COOMe | Me | Me |
| 25 | COOEt | Et | Me |
| 26 | COO-tBu | Me | Me |
| 27 | CONH₂ | nPr | Me |
| 28 | CONHMe | Me | Me |
| 29 | CONHEt | Et | Me |
| 30 | CONH-nPr | nPr | Me |
| 31 | CONMe₂ | Me | Me |
| 32 | CONEt₂ | Et | Me |
| 33 | CON(nPr)₂ | nPr | Me |
| 34 | CONHPh | Me | Me |
| 35 | 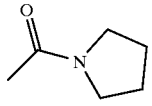 | Me | Me |
| 36 | 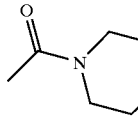 | Et | Me |

TABLE 13-continued

| Compd No | R4 | R7 | R8 |
|---|---|---|---|
| 37 | ![1-acetylazepane] | nPr | Me |

TABLE 14

| Compd No | R⁴ | R⁷ | R⁸ |
|---|---|---|---|
| 1 | NH₂ | Me | Me |
| 2 | NHMe | Me | Me |
| 3 | NHEt | Me | Me |
| 4 | NH-nPr | Et | Me |
| 5 | NMe₂ | Me | Me |
| 6 | NEt₂ | nPr | Me |
| 7 | N(nPr)₂ | nPr | Me |
| 8 | pyrrolidin-1-yl | Me | Me |
| 9 | piperidin-1-yl | Et | Me |
| 10 | azepan-1-yl | Me | Me |
| 11 | NHCOMe | nPr | Me |
| 12 | NHCOEt | Me | Me |
| 13 | NHCO-nPr | Et | Me |
| 14 | NHCOPh | Me | Me |
| 15 | NMeCOMe | nPr | Me |
| 16 | N(nPr)COMe | Me | Me |
| 17 | NMeCOPh | Et | Me |
| 18 | N(nPr)COPh | Me | Me |
| 19 | NHCOOMe | nPr | Me |
| 20 | NHCOOEt | Me | Me |
| 21 | NHCOO-tBu | Et | Me |
| 22 | NHCOOCH₂Ph | Me | Me |
| 23 | NMeCOOMe | nPr | Me |
| 24 | N(nPr)COOMe | Me | Me |
| 25 | NMeCOOCH₂Ph | nPr | Me |
| 26 | N(nPr)COOCH₂Ph | Me | Me |
| 27 | NHSO₂Me | Et | Me |
| 28 | NHSO₂Et | nPr | Me |
| 29 | NHSO₂Ph | Me | Me |
| 30 | NHTs | nPr | Me |
| 31 | NMeSO₂Me | Me | Me |
| 32 | N(nPr)SO₂Me | Et | Me |
| 33 | NMeSO₂Ph | Me | Me |
| 34 | N(nPr)SO₂Ph | Et | Me |
| 35 | COOH | Br | Me |
| 36 | COOMe | Br | Me |
| 37 | COOEt | CN | Me |
| 38 | COO-tBu | CN | Me |

TABLE 15

| Compd No | R⁴ | R⁷ | R⁸ |
|---|---|---|---|
| 1 | CONH₂ | Br | Me |
| 2 | CONHMe | Br | Me |
| 3 | CONHEt | CN | Me |
| 4 | CONH-nPr | Br | Me |
| 5 | CONMe₂ | Br | Me |
| 6 | CONEt₂ | CN | Me |
| 7 | CON(nPr)₂ | Br | Me |
| 8 | CONHPh | CN | Me |
| 9 | 1-acetylpyrrolidine | Br | Me |
| 10 | 1-acetylpiperidine | CN | Me |
| 11 | 1-acetylazepane | Br | Me |
| 12 | NH₂ | Br | Me |
| 13 | NHMe | CN | Me |
| 14 | NHEt | CN | Me |
| 15 | NH-nPr | Br | Me |
| 16 | NMe₂ | Br | Me |
| 17 | NEt₂ | CN | Me |
| 18 | N(nPr)₂ | Br | Me |
| 19 | pyrrolidin-1-yl | Br | Me |
| 20 | piperidin-1-yl | CN | Me |
| 21 | azepan-1-yl | Br | Me |
| 22 | NHCOMe | Br | Me |
| 23 | NHCOEt | Br | Me |
| 24 | NHCO-nPr | CN | Me |
| 25 | NHCOPh | Br | Me |
| 26 | NMeCOMe | Br | Me |
| 27 | N(nPr)COMe | CN | Me |
| 28 | NMeCOPh | Br | Me |
| 29 | N(nPr)COPh | Br | Me |
| 30 | NHCOOMe | CN | Me |
| 31 | NHCOOEt | Br | Me |
| 32 | NHCOO-tBu | Br | Me |
| 33 | NHCOOCH₂Ph | Br | Me |
| 34 | NMeCOOMe | CN | Me |
| 35 | N(nPr)COOMe | Br | Me |

TABLE 16

| Compd No | R⁴ | R⁷ | R⁸ |
|---|---|---|---|
| 1 | NMeCOOCH$_2$Ph | Br | Me |
| 2 | N(nPr)COOCH$_2$Ph | CN | Me |
| 3 | NHSO$_2$Me | Br | Me |
| 4 | NHSO$_2$Et | Br | Me |
| 5 | NHSO2Ph | CN | Me |
| 6 | NHTs | Br | Me |
| 7 | NMeSO$_2$Me | Br | Me |
| 8 | N(nPr)SO$_2$Me | CN | Me |
| 9 | NMeSO$_2$Ph | Br | Me |
| 10 | N(nPr)SO$_2$Ph | Br | Me |
| 11 | COOH | Ph | Me |
| 12 | COOMe | Ph | Me |
| 13 | COOEt | Ph | Me |
| 14 | COO-tBu | Ph | Me |
| 15 | CONH$_2$ | Ph | Me |
| 16 | CONHMe | Ph | Me |
| 17 | CONHEt | Ph | Me |
| 18 | CONH-nPr | Ph | Me |
| 19 | CONMe$_2$ | Ph | Me |
| 20 | CONEt$_2$ | Ph | Me |
| 21 | CON(nPr)$_2$ | Ph | Me |
| 22 | CONHPh | Ph | Me |
| 23 | acetyl-pyrrolidine | Ph | Me |
| 24 | acetyl-piperidine | Ph | Me |
| 25 | acetyl-azepane | Ph | Me |
| 26 | NH$_2$ | Ph | Me |
| 27 | NHMe | Ph | Me |
| 28 | NHEt | Ph | Me |
| 29 | NH-nPr | Ph | Me |
| 30 | NMe$_2$ | Ph | Me |
| 31 | NEt$_2$ | Ph | Me |
| 32 | N(nPr)$_2$ | Ph | Me |
| 33 | methyl-pyrrolidine | Ph | Me |
| 34 | methyl-piperidine | Ph | Me |
| 35 | methyl-azepane | Ph | Me |

TABLE 17

| Compd No | R⁴ | R⁷ | R⁸ |
|---|---|---|---|
| 1 | NHCOMe | Ph | Me |
| 2 | NHCOEt | Ph | Me |
| 3 | NHCO-nPr | Ph | Me |
| 4 | NHCOPh | Ph | Me |
| 5 | NMeCOMe | Ph | Me |
| 6 | N(nPr)COMe | Ph | Me |
| 7 | NMeCOPh | Ph | Me |
| 8 | N(nPr)COPh | Ph | Me |
| 9 | NHCOOMe | Ph | Me |
| 10 | NHCOOEt | Ph | Me |
| 11 | NHCOO-tBu | Ph | Me |
| 12 | NHCOOCH$_2$Ph | Ph | Me |
| 13 | NMeCOOMe | Ph | Me |
| 14 | N(nPr)COOMe | Ph | Me |
| 15 | NMeCOOCH$_2$Ph | Ph | Me |
| 16 | N(nPr)COOCH$_2$Ph | Ph | Me |
| 17 | NHSO$_2$Me | Ph | Me |
| 18 | NHSO$_2$Et | Ph | Me |
| 19 | NHSO$_2$Ph | Ph | Me |
| 20 | NHTs | Ph | Me |
| 21 | NMeSO$_2$Me | Ph | Me |
| 22 | N(nPr)SO$_2$Me | Ph | Me |
| 23 | NMeSO$_2$Ph | Ph | Me |
| 24 | N(nPr)SO$_2$Ph | Ph | Me |
| 25 | COOH | H | COPh |
| 26 | COOMe | H | COPh |
| 27 | COOEt | H | COPh |
| 28 | COO-tBu | H | COPh |
| 29 | CONH$_2$ | H | COPh |
| 30 | CONHMe | H | COPh |
| 31 | CONHEt | H | COPh |
| 32 | CONH-nPr | H | COPh |
| 33 | CONMe$_2$ | H | COPh |
| 34 | CONEt$_2$ | H | COPh |
| 35 | CON(nPr)$_2$ | H | COPh |
| 36 | CONHPh | H | COPh |
| 37 | acetyl-pyrrolidine | H | COPh |
| 38 | acetyl-piperidine | H | COPh |
| 39 | acetyl-azepane | H | COPh |

TABLE 18

| Compd No | R⁴ | R⁷ | R⁸ |
|---|---|---|---|
| 1 | NH$_2$ | H | COPh |
| 2 | NHMe | H | COPh |
| 3 | NHEt | H | COPh |
| 4 | NH-nPr | H | COPh |
| 5 | NMe$_2$ | H | COPh |
| 6 | NEt$_2$ | H | COPh |
| 7 | N(nPr)$_2$ | H | COPh |
| 8 | methyl-pyrrolidine | H | COPh |

TABLE 18-continued

| Compd No | R⁴ | R⁷ | R⁸ |
|---|---|---|---|
| 9 | 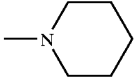 | H | COPh |
| 10 | 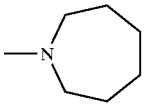 | H | COPh |
| 11 | NHCOMe | H | COPh |
| 12 | NHCOEt | H | COPh |
| 13 | NHCO-nPr | H | COPh |
| 14 | NHCOPh | H | COPh |
| 15 | NMeCOMe | H | COPh |
| 16 | N(nPr)COMe | H | COPh |
| 17 | NMeCOPh | H | COPh |
| 18 | N(nPr)COPh | H | COPh |
| 19 | NHCOOMe | H | COPh |
| 20 | NHCOOEt | H | COPh |
| 21 | NHCOO-tBu | H | COPh |
| 22 | NHCOOCH₂Ph | H | COPh |
| 23 | NMeCOOMe | H | COPh |
| 24 | N(nPr)COOMe | H | COPh |
| 25 | NMeCOOCH₂Ph | H | COPh |
| 26 | N(nPr)COOCH₂Ph | H | COPh |
| 27 | NHSO₂Me | H | COPh |
| 28 | NHSO₂Et | H | COPh |
| 29 | NHSO₂Ph | H | COPh |
| 30 | NHTs | H | COPh |
| 31 | NMeSO₂Me | H | COPh |
| 32 | N(nPr)SO₂Me | H | COPh |
| 33 | NMeSO₂Ph | H | COPh |
| 34 | N(nPr)SO₂Ph | H | COPh |
| 35 | COOH | Me | COPh |
| 36 | COOMe | Me | COPh |
| 37 | COOEt | Et | COPh |
| 38 | COO-tBu | nPr | COPh |
| 39 | CONH₂ | Me | COPh |

TABLE 19

| Compd No | R⁴ | R⁷ | R⁸ |
|---|---|---|---|
| 1 | CONHMe | Et | COPh |
| 2 | CONHEt | nPr | COPh |
| 3 | CONH-nPr | Me | COPh |
| 4 | CONMe₂ | Et | COPh |
| 5 | CONEt₂ | nPr | COPh |
| 6 | CON(nPr)₂ | nPr | COPh |
| 7 | CONHPh | Me | COPh |
| 8 | 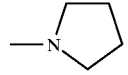 | nPr | COPh |
| 9 | 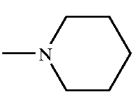 | Et | COPh |
| 10 | 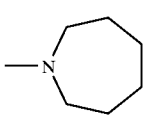 | Me | COPh |

TABLE 19-continued

| Compd No | R⁴ | R⁷ | R⁸ |
|---|---|---|---|
| 11 | NH₂ | Et | COPh |
| 12 | NHMe | Me | COPh |
| 13 | NHEt | Et | COPh |
| 14 | NH-nPr | nPr | COPh |
| 15 | NMe₂ | Me | COPh |
| 16 | NEt₂ | Et | COPh |
| 17 | N(nPr)₂ | nPr | COPh |
| 18 | 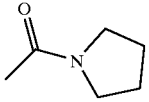 | Me | COPh |
| 19 | 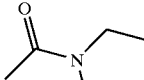 | Me | COPh |
| 20 | 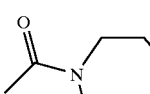 | Me | COPh |
| 21 | NHCOMe | Et | COPh |
| 22 | NHCOEt | Et | COPh |
| 23 | NHCO-nPr | Et | COPh |
| 24 | NHCOPh | nPr | COPh |
| 25 | NMeCOMe | nPr | COPh |
| 26 | N(nPr)COMe | nPr | COPh |
| 27 | NMeCOPh | Et | COPh |
| 28 | N(nPr)COPh | Et | COPh |
| 29 | NHCOOMe | Et | COPh |
| 30 | NHCOOEt | Me | COPh |
| 31 | NHCOO-tBu | Me | COPh |
| 32 | NHCOOCH₂Ph | Me | COPh |
| 33 | NMeCOOMe | Et | COPh |
| 34 | N(nPr)COOMe | nPr | COPh |
| 35 | NMeCOOCH₂Ph | nPr | COPh |
| 36 | N(nPr)COOCH₂Ph | nPr | COPh |
| 37 | NHSO₂Me | Me | COPh |
| 38 | NHSO₂Et | Et | COPh |

TABLE 20

| Compd No | R⁴ | R⁷ | R⁸ |
|---|---|---|---|
| 1 | NHSO₂Ph | nPr | COPh |
| 2 | NHTs | Me | COPh |
| 3 | NMeSO₂Me | Et | COPh |
| 4 | N(nPr)SO₂Me | nPr | COPh |
| 5 | NMeSO₂Ph | Me | COPh |
| 6 | N(nPr)SO₂Ph | Me | COPh |
| 7 | COOH | Br | COPh |
| 8 | COOMe | Br | COPh |
| 9 | COOEt | CN | COPh |
| 10 | COO-tBu | Br | COPh |
| 11 | CONH₂ | CN | COPh |
| 12 | CONHMe | Br | COPh |
| 13 | CONHEt | CN | COPh |
| 14 | CONH-nPr | Br | COPh |
| 15 | CONMe₂ | Br | COPh |
| 16 | CONEt₂ | CN | COPh |
| 17 | CON(nPr)₂ | Br | COPh |
| 18 | CONHPh | Br | COPh |
| 19 | 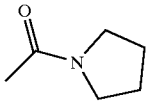 | CN | COPh |

TABLE 20-continued

| Compd No | R⁴ | R⁷ | R⁸ |
|---|---|---|---|
| 20 | 1-acetylpiperidinyl | Br | COPh |
| 21 | 1-acetylazepanyl | Br | COPh |
| 22 | NH₂ | CN | COPh |
| 23 | NHMe | Br | COPh |
| 24 | NHEt | CN | COPh |
| 25 | NH-nPr | Br | COPh |
| 26 | NMe₂ | Br | COPh |
| 27 | NEt₂ | Br | COPh |
| 28 | N(nPr)₂ | CN | COPh |
| 29 | 1-methylpyrrolidinyl | Br | COPh |
| 30 | 1-methylpiperidinyl | Br | COPh |
| 31 | 1-methylazepanyl | CN | COPh |
| 32 | NHCOMe | Br | COPh |
| 33 | NHCOEt | CN | COPh |
| 34 | NHCO-nPr | Br | COPh |
| 35 | NHCOPh | CN | COPh |
| 36 | NMeCOMe | Br | COPh |
| 37 | N(nPr)COMe | CN | COPh |

TABLE 21

| Compd No | R⁴ | R⁷ | R⁸ |
|---|---|---|---|
| 1 | NMeCOPh | CN | COPh |
| 2 | N(nPr)COPh | Br | COPh |
| 3 | NHCOOMe | Br | COPh |
| 4 | NHCOOEt | CN | COPh |
| 5 | NHCOO-tBu | Br | COPh |
| 6 | NHCOOCH₂Ph | Br | COPh |
| 7 | NMeCOOMe | CN | COPh |
| 8 | N(nPr)COOMe | Br | COPh |
| 9 | NMeCOOCH₂Ph | Br | COPh |
| 10 | N(nPr)COOCH₂Ph | CN | COPh |
| 11 | NHSO₂Me | Br | COPh |
| 12 | NHSO₂Et | Br | COPh |
| 13 | NHSO₂Ph | CN | COPh |
| 14 | NHTs | Br | COPh |
| 15 | NMeSO₂Me | Br | COPh |
| 16 | N(nPr)SO₂Me | CN | COPh |
| 17 | NMeSO2Ph | CN | COPh |
| 18 | N(nPr)SO₂Ph | CN | COPh |
| 19 | COOH | Ph | COPh |
| 20 | COOMe | Ph | COPh |
| 21 | COOEt | Ph | COPh |
| 22 | COO-tBu | Ph | COPh |
| 23 | CONH₂ | Ph | COPh |
| 24 | CONHMe | Ph | COPh |

TABLE 21-continued

| Compd No | R⁴ | R⁷ | R⁸ |
|---|---|---|---|
| 25 | CONHEt | Ph | COPh |
| 26 | CONH-nPr | Ph | COPh |
| 27 | CONMe₂ | Ph | COPh |
| 28 | CONEt₂ | Ph | COPh |
| 29 | CON(nPr)₂ | Ph | COPh |
| 30 | CONHPh | Ph | COPh |
| 31 | 1-acetylpyrrolidinyl | Ph | COPh |
| 32 | 1-acetylpiperidinyl | Ph | COPh |
| 33 | 1-acetylazepanyl | Ph | COPh |
| 34 | NH₂ | Ph | COPh |
| 35 | NHMe | Ph | COPh |
| 36 | NHEt | Ph | COPh |

TABLE 22

| Compd No | R⁴ | R⁷ | R⁸ |
|---|---|---|---|
| 1 | NH-nPr | Ph | COPh |
| 2 | NMe₂ | Ph | COPh |
| 3 | NEt₂ | Ph | COPh |
| 4 | N(nPr)₂ | Ph | COPh |
| 5 | 1-methylpyrrolidinyl | Ph | COPh |
| 6 | 1-methylpiperidinyl | Ph | COPh |
| 7 | 1-methylazepanyl | Ph | COPh |
| 8 | NHCOMe | Ph | COPh |
| 9 | NHCOEt | Ph | COPh |
| 10 | NHCO-nPr | Ph | COPh |
| 11 | NHCOPh | Ph | COPh |
| 12 | NMeCOMe | Ph | COPh |
| 13 | N(nPr)COMe | Ph | COPh |
| 14 | NMeCOPh | Ph | COPh |
| 15 | N(nPr)COPh | Ph | COPh |
| 16 | NHCOOMe | Ph | COPh |
| 17 | NHCOOEt | Ph | COPh |
| 18 | NHCOO-tBu | Ph | COPh |
| 19 | NHCOOCH₂Ph | Ph | COPh |
| 20 | NMeCOOMe | Ph | COPh |
| 21 | N(nPr)COOMe | Ph | COPh |
| 22 | NMeCOOCH₂Ph | Ph | COPh |
| 23 | N(nPr)COOCH₂Ph | Ph | COPh |
| 24 | NHSO₂Me | Ph | COPh |

TABLE 22-continued

| Compd No | $R^4$ | $R^7$ | $R^8$ |
|---|---|---|---|
| 25 | NHSO$_2$Et | Ph | COPh |
| 26 | NHSO$_2$Ph | Ph | COPh |
| 27 | NHTs | Ph | COPh |
| 28 | NMeSO$_2$Me | Ph | COPh |
| 29 | N(nPr)SO$_2$Me | Ph | COPh |
| 30 | NMeSO$_2$Ph | Ph | COPh |
| 31 | N(nPr)SO$_2$Ph | Ph | COPh |
| 32 | COOH | H | SO$_2$Ph |
| 33 | COOMe | H | SO$_2$Ph |
| 34 | COOEt | H | SO$_2$Ph |
| 35 | COO-tBu | H | SO$_2$Ph |
| 36 | CONH$_2$ | H | SO$_2$Ph |
| 37 | CONHMe | H | SO$_2$Ph |

TABLE 23

| Compd No | $R^4$ | $R^7$ | $R^8$ |
|---|---|---|---|
| 1 | CONHEt | H | SO$_2$Ph |
| 2 | CONH-nPr | H | SO$_2$Ph |
| 3 | CONMe$_2$ | H | SO$_2$Ph |
| 4 | CONEt$_2$ | H | SO$_2$Ph |
| 5 | CON(nPr)$_2$ | H | SO$_2$Ph |
| 6 | CONHPh | H | SO$_2$Ph |
| 7 | 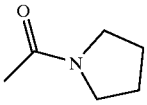 | H | SO$_2$Ph |
| 8 | 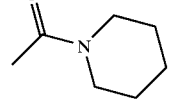 | H | SO$_2$Ph |
| 9 | 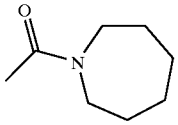 | H | SO$_2$Ph |
| 10 | NH$_2$ | H | SO$_2$Ph |
| 11 | NHMe | H | SO$_2$Ph |
| 12 | NHEt | H | SO$_2$Ph |
| 13 | NH-nPr | H | SO$_2$Ph |
| 14 | NMe$_2$ | H | SO$_2$Ph |
| 15 | NEt$_2$ | H | SO$_2$Ph |
| 16 | N(nPr)$_2$ | H | SO$_2$Ph |
| 17 | 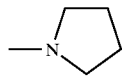 | H | SO$_2$Ph |
| 18 | 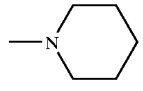 | H | SO$_2$Ph |
| 19 | 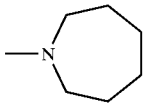 | H | SO$_2$Ph |
| 20 | NHCOMe | H | SO$_2$Ph |
| 21 | NHCOEt | H | SO$_2$Ph |
| 22 | NHCO-nPr | H | SO$_2$Ph |
| 23 | NHCOPh | H | SO$_2$Ph |

TABLE 23-continued

| Compd No | $R^4$ | $R^7$ | $R^8$ |
|---|---|---|---|
| 24 | NMeCOMe | H | SO$_2$Ph |
| 25 | N(nPr)COMe | H | SO$_2$Ph |
| 26 | NMeCOPh | H | SO$_2$Ph |
| 27 | N(nPr)COPh | H | SO$_2$Ph |
| 28 | NHCOOMe | H | SO$_2$Ph |
| 29 | NHCOOEt | H | SO$_2$Ph |
| 30 | NHCOO-tBu | H | SO$_2$Ph |
| 31 | NHCOOCH$_2$Ph | H | SO$_2$Ph |
| 32 | NMeCOOMe | H | SO$_2$Ph |
| 33 | N(nPr)COOMe | H | SO$_2$Ph |
| 34 | NMeCOOCH$_2$Ph | H | SO$_2$Ph |
| 35 | N(nPr)COOCH$_2$Ph | H | SO$_2$Ph |
| 36 | NHSO$_2$Me | H | SO$_2$Ph |
| 37 | NHSO$_2$Et | H | SO$_2$Ph |

TABLE 24

| Compd No | $R^4$ | $R^7$ | $R^8$ |
|---|---|---|---|
| 1 | NHSO$_2$Ph | H | SO$_2$Ph |
| 2 | NHTs | H | SO$_2$Ph |
| 3 | NMeSO$_2$Me | H | SO$_2$Ph |
| 4 | N(nPr)SO$_2$Me | H | SO$_2$Ph |
| 5 | NMeSO$_2$Ph | H | SO$_2$Ph |
| 6 | N(nPr)SO$_2$Ph | H | SO$_2$Ph |
| 7 | COOH | Me | SO$_2$Ph |
| 8 | COOMe | Me | SO$_2$Ph |
| 9 | COOEt | Et | SO$_2$Ph |
| 10 | COO-tBu | nPr | SO$_2$Ph |
| 11 | CONH$_2$ | Me | SO$_2$Ph |
| 12 | CONHMe | Me | SO$_2$Ph |
| 13 | CONHEt | Et | SO$_2$Ph |
| 14 | CONH-nPr | nPr | SO$_2$Ph |
| 15 | CONMe$_2$ | Me | SO$_2$Ph |
| 16 | CONEt$_2$ | Me | SO$_2$Ph |
| 17 | CON(nPr)$_2$ | Me | SO$_2$Ph |
| 18 | CONHPh | Et | SO$_2$Ph |
| 19 | 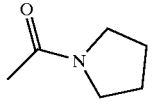 | Et | SO$_2$Ph |
| 20 | 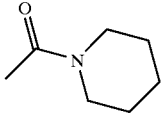 | Et | SO$_2$Ph |
| 21 | 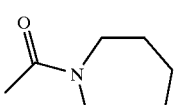 | nPr | SO$_2$Ph |
| 22 | NH$_2$ | nPr | SO$_2$Ph |
| 23 | NHMe | nPr | SO$_2$Ph |
| 24 | NHEt | Et | SO$_2$Ph |
| 25 | NH-nPr | Me | SO$_2$Ph |
| 26 | NMe$_2$ | nPr | SO$_2$Ph |
| 27 | NEt$_2$ | Et | SO$_2$Ph |
| 28 | N(nPr)$_2$ | Et | SO$_2$Ph |
| 29 | 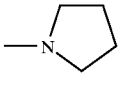 | Me | SO$_2$Ph |

TABLE 24-continued

| Compd No | R⁴ | R⁷ | R⁸ |
|---|---|---|---|
| 30 | N-methylpiperidinyl | Me | SO₂Ph |
| 31 | N-methylazepanyl | Me | SO₂Ph |
| 32 | NHCOMe | Et | SO₂Ph |
| 33 | NHCOEt | Et | SO₂Ph |
| 34 | NHCO-nPr | Et | SO₂Ph |
| 35 | NHCOPh | Me | SO₂Ph |
| 36 | NMeCOMe | Me | SO₂Ph |

TABLE 25

| Compd No | R⁴ | R⁷ | R⁸ |
|---|---|---|---|
| 1 | N(nPr)COMe | Me | SO₂Ph |
| 2 | NMeCOPh | nPr | SO₂Ph |
| 3 | N(nPr)COPh | nPr | SO₂Ph |
| 4 | NHCOOMe | nPr | SO₂Ph |
| 5 | NHCOOEt | Me | SO₂Ph |
| 6 | NHCOO-tBu | Et | SO₂Ph |
| 7 | NHCOOCH₂Ph | nPr | SO₂Ph |
| 8 | NMeCOOMe | Me | SO₂Ph |
| 9 | N(nPr)COOMe | Et | SO₂Ph |
| 10 | NMeCOOCH₂Ph | nPr | SO₂Ph |
| 11 | N(nPr)COOCH₂Ph | Me | SO₂Ph |
| 12 | NHSO₂Me | Et | SO₂Ph |
| 13 | NHSO₂Et | nPr | SO₂Ph |
| 14 | NHSO₂Ph | Me | SO₂Ph |
| 15 | NHTs | Me | SO₂Ph |
| 16 | NMeSO₂Me | Me | SO₂Ph |
| 17 | N(nPr)SO₂Me | nPr | SO₂Ph |
| 18 | NMeSO₂Ph | nPr | SO₂Ph |
| 19 | N(nPr)SO₂Ph | nPr | SO₂Ph |
| 20 | COOH | Br | SO₂Ph |
| 21 | COOMe | CN | SO₂Ph |
| 22 | COOEt | Br | SO₂Ph |
| 23 | COO-tBu | CN | SO₂Ph |
| 24 | CONH² | Br | SO₂Ph |
| 25 | CONHMe | Br | SO₂Ph |
| 26 | CONHEt | Br | SO₂Ph |
| 27 | CONH-nPr | Br | SO₂Ph |
| 28 | CONMe₂ | CN | SO₂Ph |
| 29 | CONEt₂ | CN | SO₂Ph |
| 30 | CON(nPr)₂ | CN | SO₂Ph |
| 31 | CONHPh | Br | SO₂Ph |
| 32 | acetylpyrrolidinyl | Br | SO₂Ph |
| 33 | acetylpiperidinyl | Br | SO₂Ph |
| 34 | acetylazepanyl | CN | SO₂Ph |

TABLE 25-continued

| Compd No | R⁴ | R⁷ | R⁸ |
|---|---|---|---|
| 35 | NH₂ | Br | SO₂Ph |
| 36 | NHMe | CN | SO2Ph |

TABLE 26

| Compd No | R⁴ | R⁷ | R⁸ |
|---|---|---|---|
| 1 | NHEt | Br | SO₂Ph |
| 2 | NH-nPr | CN | SO₂Ph |
| 3 | NMe₂ | Br | SO₂Ph |
| 4 | NEt₂ | Br | SO₂Ph |
| 5 | N(nPr)₂ | CN | SO₂Ph |
| 6 | N-methylpyrrolidinyl | Br | SO₂Ph |
| 7 | N-methylpiperidinyl | Br | SO₂Ph |
| 8 | N-methylazepanyl | Br | SO₂Ph |
| 9 | NHCOMe | CN | SO₂Ph |
| 10 | NHCOEt | Br | SO₂Ph |
| 11 | NHCO-nPr | CN | SO₂Ph |
| 12 | NHCOPh | Br | SO₂Ph |
| 13 | NMeCOMe | Br | SO₂Ph |
| 14 | N(nPr)COMe | CN | SO₂Ph |
| 15 | NMeCOPh | Br | SO₂Ph |
| 16 | N(nPr)COPh | Br | SO₂Ph |
| 17 | NHCOOMe | CN | SO₂Ph |
| 18 | NHCOOEt | Br | SO₂Ph |
| 19 | NHCOO-tBu | Br | SO₂Ph |
| 20 | NHCOOCH₂Ph | Br | SO₂Ph |
| 21 | NMeCOOMe | CN | SO₂Ph |
| 22 | N(nPr)COOMe | Br | SO₂Ph |
| 23 | NMeCOOCH₂Ph | Br | SO₂Ph |
| 24 | N(nPr)COOCH₂Ph | Br | SO₂Ph |
| 25 | NHSO₂Me | CN | SO₂Ph |
| 26 | NHSO₂Et | Br | SO₂Ph |
| 27 | NHSO₂Ph | Br | SO₂Ph |
| 28 | NHTs | CN | SO₂Ph |
| 29 | NMeSO₂Me | Br | SO₂Ph |
| 30 | N(nPr)SO₂Me | Br | SO₂Ph |
| 31 | NMeSO₂Ph | CN | SO₂Ph |
| 32 | N(nPr)SO₂Ph | Br | SO₂Ph |
| 33 | COOH | Ph | SO₂Ph |
| 34 | COOMe | Ph | SO₂Ph |
| 35 | COOEt | Ph | SO₂Ph |
| 36 | COO-tBu | Ph | SO₂Ph |
| 37 | CONH₂ | Ph | SO2Ph |

TABLE 27

| Compd No | R⁴ | R⁷ | R⁸ |
|---|---|---|---|
| 1 | CONHMe | Ph | SO₂Ph |
| 2 | CONHEt | Ph | SO₂Ph |
| 3 | CONH-nPr | Ph | SO₂Ph |
| 4 | CONMe₂ | Ph | SO₂Ph |
| 5 | CONEt₂ | Ph | SO₂Ph |
| 6 | CON(nPr)₂ | Ph | SO₂Ph |
| 7 | CONHPh | Ph | SO₂Ph |

TABLE 27-continued

| Compd No | R⁴ | R⁷ | R⁸ |
|---|---|---|---|
| 8 | 1-acetylpyrrolidinyl | Ph | SO₂Ph |
| 9 | 1-acetylpiperidinyl | Ph | SO₂Ph |
| 10 | 1-acetylazepanyl | Ph | SO₂Ph |
| 11 | NH₂ | Ph | SO₂Ph |
| 12 | NHMe | Ph | SO₂Ph |
| 13 | NHEt | Ph | SO₂Ph |
| 14 | NH-nPr | Ph | SO₂Ph |
| 15 | NMe₂ | Ph | SO₂Ph |
| 16 | NEt₂ | Ph | SO₂Ph |
| 17 | N(nPr)₂ | Ph | SO₂Ph |
| 18 | 1-methylpyrrolidinyl | Ph | SO₂Ph |
| 19 | 1-methylpiperidinyl | Ph | SO₂Ph |
| 20 | 1-methylazepanyl | Ph | SO₂Ph |
| 21 | NHCOMe | Ph | SO₂Ph |
| 22 | NHCOEt | Ph | SO₂Ph |
| 23 | NHCO-nPr | Ph | SO₂Ph |
| 24 | NHCOPh | Ph | SO₂Ph |
| 25 | NMeCOMe | Ph | SO₂Ph |
| 26 | N(nPr)COMe | Ph | SO₂Ph |
| 27 | NMeCOPh | Ph | SO₂Ph |
| 28 | N(nPr)COPh | Ph | SO₂Ph |
| 29 | NHCOOMe | Ph | SO₂Ph |
| 30 | NHCOOEt | Ph | SO₂Ph |
| 31 | NHCOO-tBu | Ph | SO₂Ph |
| 32 | NHCOOCH₂Ph | Ph | SO₂Ph |
| 33 | NMeCOOMe | Ph | SO₂Ph |
| 34 | N(nPr)COOMe | Ph | SO₂Ph |
| 35 | NMeCOOCH₂Ph | Ph | SO₂Ph |
| 36 | N(nPr)COOCH₂Ph | Ph | SO2Ph |

TABLE 28

| Compd No | R⁴ | R⁷ | R⁸ |
|---|---|---|---|
| 1 | NHSO₂Me | Ph | SO₂Ph |
| 2 | NHSO₂Et | Ph | SO₂Ph |
| 3 | NHSO₂Ph | Ph | SO₂Ph |
| 4 | NHTs | Ph | SO₂Ph |
| 5 | NMeSO₂Me | Ph | SO₂Ph |

TABLE 28-continued

| Compd No | R⁴ | R⁷ | R⁸ |
|---|---|---|---|
| 6 | N(nPr)SO₂Me | Ph | SO₂Ph |
| 7 | NMeSO₂Ph | Ph | SO₂Ph |
| 8 | N(nPr)SO₂Ph | Ph | SO₂Ph |

TABLE 29

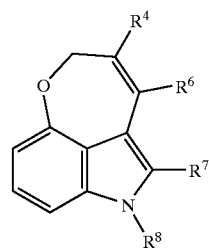

(I-b)

| Compd No | R⁴ | R⁶ | R⁷ | R⁸ |
|---|---|---|---|---|
| 1 | COOH | H | H | H |
| 2 | COOMe | H | H | H |
| 3 | COOEt | H | H | H |
| 4 | COO-tBu | H | H | H |
| 5 | CONH₂ | H | H | H |
| 6 | CONHMe | H | H | H |
| 7 | CONHEt | H | H | H |
| 8 | CONH-nPr | H | H | H |
| 9 | CONMe₂ | H | H | H |
| 10 | CONEt₂ | H | H | H |
| 11 | CON(nPr)₂ | H | H | H |
| 12 | CONHPh | H | H | H |
| 13 | 1-acetylpyrrolidinyl | H | H | H |
| 14 | 1-acetylpiperidinyl | H | H | H |
| 15 | 1-acetylazepanyl | H | H | H |
| 16 | NHCOOMe | H | H | H |
| 17 | NHCOOEt | H | H | H |
| 18 | NHCOO-tBu | H | H | H |
| 19 | NHCOOCH₂Ph | H | H | H |
| 20 | NMeCOOMe | H | H | H |
| 21 | N(nPr)COOMe | H | H | H |
| 22 | NMeCOOCH₂Ph | H | H | H |
| 23 | N(nPr)COOCH₂Ph | H | H | H |
| 24 | COOH | H | Me | H |
| 25 | COOMe | H | Me | H |
| 26 | COOEt | H | Et | H |

TABLE 30

| Compd No | R⁴ | R⁶ | R⁷ | R⁸ |
|---|---|---|---|---|
| 1 | COO-tBu | H | nPr | H |
| 2 | CONH₂ | H | Me | H |
| 3 | CONHMe | H | Me | H |
| 4 | CONHEt | H | Et | H |
| 5 | CONH-nPr | H | nPr | H |
| 6 | CONMe₂ | H | Me | H |
| 7 | CONEt₂ | H | Me | H |
| 8 | CON(nPr)₂ | H | Me | H |
| 9 | CONHPh | H | Et | H |
| 10 | acetyl-pyrrolidine | H | Et | H |
| 11 | acetyl-piperidine | H | Et | H |
| 12 | acetyl-azepane | H | Et | H |
| 13 | NHCOOMe | H | nPr | H |
| 14 | NHCOOEt | H | nPr | H |
| 15 | NHCOO-tBu | H | nPr | H |
| 16 | NHCOOCH₂Ph | H | Me | H |
| 17 | NMeCOOMe | H | Et | H |
| 18 | N(nPr)COOMe | H | nPr | H |
| 19 | NMeCOOCH₂Ph | H | Me | H |
| 20 | N(nPr)COOCH₂Ph | H | nPr | H |
| 21 | COOH | H | Br | H |
| 22 | COOMe | H | Br | H |
| 23 | COOEt | H | CN | H |
| 24 | COO-tBu | H | Br | H |
| 25 | CONH₂ | H | Br | H |
| 26 | CONHMe | H | CN | H |
| 27 | CONHEt | H | Br | H |
| 28 | CONH-nPr | H | CN | H |
| 29 | CONMe₂ | H | Br | H |
| 30 | CONEt₂ | H | Br | H |
| 31 | CON(nPr)₂ | H | CN | H |
| 32 | CONHPh | H | Br | H |
| 33 | acetyl-pyrrolidine | H | Br | H |
| 34 | acetyl-piperidine | H | CN | H |
| 35 | acetyl-azepane | H | Br | H |

TABLE 31

| Compd No. | R⁴ | R⁶ | R⁷ | R⁸ |
|---|---|---|---|---|
| 1 | NHCOOMe | H | Br | H |
| 2 | NHCOOEt | H | CN | H |
| 3 | NHCOO-tBu | H | Br | H |
| 4 | NHCOOCH₂Ph | H | CN | H |
| 5 | NMeCOOMe | H | Br | H |
| 6 | N(nPr)COOMe | H | CN | H |
| 7 | NMeCOOCH₂Ph | H | Br | H |
| 8 | N(nPr)COOCH₂Ph | H | CN | H |
| 9 | COOH | H | Ph | H |
| 10 | COOMe | H | Ph | H |
| 11 | COOEt | H | Ph | H |
| 12 | COO-tBu | H | Ph | H |
| 13 | CONH₂ | H | Ph | H |
| 14 | CONHMe | H | Ph | H |
| 15 | CONHEt | H | Ph | H |
| 16 | CONH-nPr | H | Ph | H |
| 17 | CONMe₂ | H | Ph | H |
| 18 | CONEt₂ | H | Ph | H |
| 19 | CON(nPr)₂ | H | Ph | H |
| 20 | CONHPh | H | Ph | H |
| 21 | acetyl-pyrrolidine | H | Ph | H |
| 22 | acetyl-piperidine | H | Ph | H |
| 23 | acetyl-azepane | H | Ph | H |
| 24 | NHCOOMe | H | Ph | H |
| 25 | NHCOOEt | H | Ph | H |
| 26 | NHCOO-tBu | H | Ph | H |
| 27 | NHCOOCH₂Ph | H | Ph | H |
| 28 | NMeCOOMe | H | Ph | H |
| 29 | N(nPr)COOMe | H | Ph | H |
| 30 | NMeCOOCH₂Ph | H | Ph | H |
| 31 | N(nPr)COOCH₂Ph | H | Ph | H |
| 32 | COOH | H | H | Me |
| 33 | COOMe | H | H | Me |
| 34 | COOEt | H | H | Me |
| 35 | COO-tBu | H | H | Me |
| 36 | CONH₂ | H | H | Me |
| 37 | CONHMe | H | H | Me |

TABLE 32

| Compd No | R⁴ | R⁶ | R⁷ | R⁸ |
|---|---|---|---|---|
| 1 | CONHEt | H | H | Me |
| 2 | CONH-nPr | H | H | Me |
| 3 | CONMe₂ | H | H | Me |
| 4 | CONEt₂ | H | H | Me |
| 5 | CON(nPr)₂ | H | H | Me |
| 6 | CONHPh | H | H | Me |
| 7 | acetyl-pyrrolidine | H | H | Me |

TABLE 32-continued

| Compd No | R⁴ | R⁶ | R⁷ | R⁸ |
|---|---|---|---|---|
| 8 | *1-acetylpiperidine* | H | H | Me |
| 9 | *1-acetylazepane* | H | H | Me |
| 10 | NHCOOMe | H | H | Me |
| 11 | NHCOOEt | H | H | Me |
| 12 | NHCOO-tBu | H | H | Me |
| 13 | NHCOOCH₂Ph | H | H | Me |
| 14 | NMeCOOMe | H | H | Me |
| 15 | N(nPr)COOMe | H | H | Me |
| 16 | NMeCOOCH₂Ph | H | H | Me |
| 17 | N(nPr)COOCH₂Ph | H | H | Me |
| 18 | COOH | H | Me | Me |
| 19 | COOMe | H | Me | Me |
| 20 | COOEt | H | Me | Me |
| 21 | COO-tBu | H | nPr | Me |
| 22 | CONH₂ | H | Me | Me |
| 23 | CONHMe | H | Me | Me |
| 24 | CONHEt | H | Me | Me |
| 25 | CONH-nPr | H | Et | Me |
| 26 | CONMe₂ | H | Et | Me |
| 27 | CONEt₂ | H | Et | Me |
| 28 | CON(nPr)₂ | H | nPr | Me |
| 29 | CONHPh | H | nPr | Me |
| 30 | *1-acetylpyrrolidine* | H | nPr | Me |
| 31 | *1-acetylpiperidine* | H | Me | Me |
| 32 | *1-acetylazepane* | H | Et | Me |
| 33 | NHCOOMe | H | nPr | Me |
| 34 | NHCOOEt | H | Me | Me |

TABLE 33

| Compd No | R⁴ | R⁶ | R⁷ | R⁸ |
|---|---|---|---|---|
| 1 | NHCOO-tBu | H | Et | Me |
| 2 | NHCOOCH₂Ph | H | nPr | Me |
| 3 | NMeCOOMe | H | Me | Me |
| 4 | N(nPr)COOMe | H | Me | Me |
| 5 | NMeCOOCH₂Ph | H | Et | Me |
| 6 | N(nPr)COOCH₂Ph | H | nPr | Me |
| 7 | COOH | H | Br | Me |
| 8 | COOMe | H | CN | Me |
| 9 | COOEt | H | Br | Me |
| 10 | COO-tBu | H | CN | Me |
| 11 | CONH₂ | H | Br | Me |

TABLE 33-continued

| Compd No | R⁴ | R⁶ | R⁷ | R⁸ |
|---|---|---|---|---|
| 12 | CONHMe | H | CN | Me |
| 13 | CONHEt | H | Br | Me |
| 14 | CONH-nPr | H | CN | Me |
| 15 | CONMe₂ | H | Br | Me |
| 16 | CONEt₂ | H | CN | Me |
| 17 | CON(nPr)₂ | H | Br | Me |
| 18 | CONHPh | H | CN | Me |
| 19 | *1-acetylpyrrolidine* | H | Br | Me |
| 20 | *1-acetylpiperidine* | H | Br | Me |
| 21 | *1-acetylazepane* | H | CN | Me |
| 22 | NHCOOMe | H | CN | Me |
| 23 | NHCOOEt | H | Br | Me |
| 24 | NHCOO-tBu | H | CN | Me |
| 25 | NHCOOCH₂Ph | H | Br | Me |
| 26 | NMeCOOMe | H | Br | Me |
| 27 | N(nPr)COOMe | H | CN | Me |
| 28 | NMeCOOCH₂Ph | H | Br | Me |
| 29 | N(nPr)COOCH₂Ph | H | Br | Me |
| 30 | COOH | H | Ph | Me |
| 31 | COOMe | H | Ph | Me |
| 32 | COOEt | H | Ph | Me |
| 33 | COO-tBu | H | Ph | Me |
| 34 | CONH₂ | H | Ph | Me |
| 35 | CONHMe | H | Ph | Me |
| 36 | CONHEt | H | Ph | Me |
| 37 | CONH-nPr | H | Ph | Me |

TABLE 34

| Compd No | R⁴ | R⁶ | R⁷ | R⁸ |
|---|---|---|---|---|
| 1 | CONMe₂ | H | Ph | Me |
| 2 | CONEt₂ | H | Ph | Me |
| 3 | CON(nPr)₂ | H | Ph | Me |
| 4 | CONHPh | H | Ph | Me |
| 5 | *1-acetylpyrrolidine* | H | Ph | Me |
| 6 | *1-acetylpiperidine* | H | Ph | Me |
| 7 | *1-acetylazepane* | H | Ph | Me |

TABLE 34-continued

| Compd No | R⁴ | R⁶ | R⁷ | R⁸ |
|---|---|---|---|---|
| 8 | NHCOOMe | H | Ph | Me |
| 9 | NHCOOEt | H | Ph | Me |
| 10 | NHCOO-tBu | H | Ph | Me |
| 11 | NHCOOCH₂Ph | H | Ph | Me |
| 12 | NMeCOOMe | H | Ph | Me |
| 13 | N(nPr)COOMe | H | Ph | Me |
| 14 | NMeCOOCH₂Ph | H | Ph | Me |
| 15 | N(nPr)COOCH₂Ph | H | Ph | Me |
| 16 | COOH | H | H | COPh |
| 17 | COOMe | H | H | COPh |
| 18 | COOEt | H | H | COPh |
| 19 | COO-tBu | H | H | COPh |
| 20 | CONH₂ | H | H | COPh |
| 21 | CONHMe | H | H | COPh |
| 22 | CONHEt | H | H | COPh |
| 23 | CONH-nPr | H | H | COPh |
| 24 | CONMe₂ | H | H | COPh |
| 25 | CONEt₂ | H | H | COPh |
| 26 | CON(nPr)₂ | H | H | COPh |
| 27 | CONHPh | H | H | COPh |
| 28 | Ac-pyrrolidinyl | H | H | COPh |
| 29 | Ac-piperidinyl | H | H | COPh |
| 30 | Ac-azepanyl | H | H | COPh |
| 31 | NHCOOMe | H | H | COPh |
| 32 | NHCOOEt | H | H | COPh |
| 33 | NHCOO-tBu | H | H | COPh |
| 34 | NHCOOCH₂Ph | H | H | COPh |

TABLE 35

| Compd No | R⁴ | R⁶ | R⁷ | R⁸ |
|---|---|---|---|---|
| 1 | NMeCOOMe | H | H | COPh |
| 2 | N(nPr)COOMe | H | H | COPh |
| 3 | NMeCOOCH₂Ph | H | H | COPh |
| 4 | N(nPr)COOCH₂Ph | H | H | COPh |
| 5 | COOH | H | Me | COPh |
| 6 | COOMe | H | nPr | COPh |
| 7 | COOEt | H | Et | COPh |
| 8 | COO-tBu | H | Et | COPh |
| 9 | CONH₂ | H | Et | COPh |
| 10 | CONHMe | H | Me | COPh |
| 11 | CONHEt | H | Me | COPh |
| 12 | CONH-nPr | H | Me | COPh |
| 13 | CONMe₂ | H | nPr | COPh |
| 14 | CONEt₂ | H | nPr | COPh |
| 15 | CON(nPr)₂ | H | nPr | COPh |
| 16 | CONHPh | H | Me | COPh |
| 17 | Ac-pyrrolidinyl | H | Et | COPh |
| 18 | Ac-piperidinyl | H | nPr | COPh |
| 19 | Ac-azepanyl | H | Me | COPh |
| 20 | NHCOOMe | H | Me | COPh |
| 21 | NHCOOEt | H | Me | COPh |
| 22 | NHCOO-tBu | H | Et | COPh |
| 23 | NHCOOCH₂Ph | H | nPr | COPh |
| 24 | NMeCOOMe | H | Et | COPh |
| 25 | N(nPr)COOMe | H | nPr | COPh |
| 26 | NMeCOOCH₂Ph | H | Me | COPh |
| 27 | N(nPr)COOCH₂Ph | H | Me | COPh |
| 28 | COOH | H | Br | COPh |
| 29 | COOMe | H | CN | COPh |
| 30 | COOEt | H | Br | COPh |
| 31 | COO-tBu | H | CN | COPh |
| 32 | CONH₂ | H | Br | COPh |
| 33 | CONHMe | H | Br | COPh |
| 34 | CONHEt | H | CN | COPh |
| 35 | CONH-nPr | H | CN | COPh |
| 36 | CONMe₂ | H | Br | COPh |

TABLE 36

| Compd No | R⁴ | R⁶ | R⁷ | R⁸ |
|---|---|---|---|---|
| 1 | CONEt₂ | H | Br | COPh |
| 2 | CON(nPr)₂ | H | Br | COPh |
| 3 | CONHPh | H | Br | COPh |
| 4 | Ac-pyrrolidinyl | H | CN | COPh |
| 5 | Ac-piperidinyl | H | CN | COPh |
| 6 | Ac-azepanyl | H | Br | COPh |
| 7 | NHCOOMe | H | CN | COPh |
| 8 | NHCOOEt | H | Br | COPh |
| 9 | NHCOO-tBu | H | CN | COPh |
| 10 | NHCOOCH₂Ph | H | Br | COPh |
| 11 | NMeCOOMe | H | CN | COPh |
| 12 | N(nPr)COOMe | H | Br | COPh |
| 13 | NMeCOOCH₂Ph | H | Br | COPh |
| 14 | N(nPr)COOCH₂Ph | H | Br | COPh |
| 15 | COOH | H | Ph | COPh |
| 16 | COOMe | H | Ph | COPh |
| 17 | COOEt | H | Ph | COPh |
| 18 | COO-tBu | H | Ph | COPh |

TABLE 36-continued

| Compd No | R⁴ | R⁶ | R⁷ | R⁸ |
|---|---|---|---|---|
| 19 | CONH₂ | H | Ph | COPh |
| 20 | CONHMe | H | Ph | COPh |
| 21 | CONHEt | H | Ph | COPh |
| 22 | CONH-nPr | H | Ph | COPh |
| 23 | CONMe₂ | H | Ph | COPh |
| 24 | CONEt₂ | H | Ph | COPh |
| 25 | CON(nPr)₂ | H | Ph | COPh |
| 26 | CONHPh | H | Ph | COPh |
| 27 | 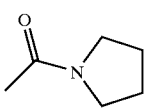 | H | Ph | COPh |
| 28 | 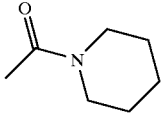 | H | Ph | COPh |
| 29 | 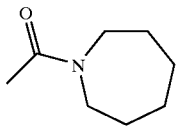 | H | Ph | COPh |
| 30 | NHCOOMe | H | Ph | COPh |
| 31 | NHCOOEt | H | Ph | COPh |
| 32 | NHCOO-tBu | H | Ph | COPh |

TABLE 37

| Compd No | R⁴ | R⁶ | R⁷ | R⁸ |
|---|---|---|---|---|
| 1 | NHCOOCH₂Ph | H | Ph | COPh |
| 2 | NMeCOOMe | H | Ph | COPh |
| 3 | N(nPr)COOMe | H | Ph | COPh |
| 4 | NMeCOOCH₂Ph | H | Ph | COPh |
| 5 | N(nPr)COOCH₂Ph | H | Ph | COPh |
| 6 | COOH | H | H | SO₂Ph |
| 7 | COOMe | H | H | SO₂Ph |
| 8 | COOEt | H | H | SO₂Ph |
| 9 | COO-tBu | H | H | SO₂Ph |
| 10 | CONH₂ | H | H | SO₂Ph |
| 11 | CONHMe | H | H | SO₂Ph |
| 12 | CONHEt | H | H | SO₂Ph |
| 13 | CONHn-Pr | H | H | SO₂Ph |
| 14 | CONMe₂ | H | H | SO₂Ph |
| 15 | CONEt₂ | H | H | SO₂Ph |
| 16 | CON(nPr)₂ | H | H | SO₂Ph |
| 17 | CONHPh | H | H | SO₂Ph |
| 18 | 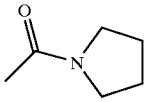 | H | H | SO₂Ph |
| 19 | 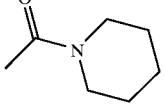 | H | H | SO₂Ph |
| 20 | 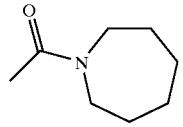 | H | H | SO₂Ph |
| 21 | NHCOOMe | H | H | SO₂Ph |
| 22 | NHCOOEt | H | H | SO₂Ph |
| 23 | NHCOO-tBu | H | H | SO₂Ph |
| 24 | NHCOOCH₂Ph | H | H | SO₂Ph |
| 25 | NMeCOOMe | H | H | SO₂Ph |
| 26 | N(nPr)COOMe | H | H | SO₂Ph |
| 27 | NMeCOOCH₂Ph | H | H | SO₂Ph |
| 28 | N(nPr)COOCH₂Ph | H | H | SO₂Ph |
| 29 | COOH | H | Me | SO₂Ph |
| 30 | COOMe | H | Et | SO₂Ph |
| 31 | COOEt | H | nPr | SO₂Ph |
| 32 | COO-tBu | H | Et | SO₂Ph |
| 33 | CONH₂ | H | nPr | SO₂Ph |
| 34 | CONHMe | H | Me | SO₂Ph |
| 35 | CONHEt | H | Me | SO₂Ph |
| 36 | CONH-nPr | H | nPr | SO₂Ph |

TABLE 38

| Compd No | R⁴ | R⁶ | R⁷ | R⁸ |
|---|---|---|---|---|
| 1 | CONMe₂ | H | nPr | SO₂Ph |
| 2 | CONEt₂ | H | Et | SO₂PII |
| 3 | CON(nPr)₂ | H | Et | SO₂Ph |
| 4 | CONHPh | H | nPr | SO₂Ph |
| 5 | 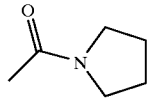 | H | nPr | SO₂Ph |
| 6 | 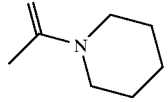 | H | nPr | SO₂Ph |
| 7 | 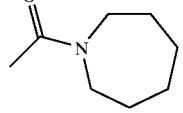 | H | Me | SO₂Ph |
| 8 | NHCOOMe | H | Me | SO₂Ph |
| 9 | NHCOOEt | H | Me | SO₂Ph |
| 10 | NHCOO-tBu | H | Et | SO₂Ph |
| 11 | NHCOOCH₂Ph | H | Et | SO₂Ph |
| 12 | NMeCOOMe | H | Et | SO₂Ph |
| 13 | N(nPr)COOMe | H | Me | SO₂Ph |
| 14 | NMeCOOCH₂Ph | H | Me | SO₂Ph |
| 15 | N(nPr)COOCH₂Ph | H | Me | SO₂PIi |
| 16 | COOH | H | Br | SO₂Ph |
| 17 | COOMe | H | Br | SO₂Ph |
| 18 | COOEt | H | Br | SO₂Ph |
| 19 | COO-tBu | H | CN | SO₂Ph |
| 20 | CONH₂ | H | Br | SO₂Ph |
| 21 | CONHMe | H | Br | SO₂PIi |
| 22 | CONHEt | H | Br | SO₂Ph |
| 23 | CONH-nPr | H | CN | SO₂Ph |
| 24 | CONMe₂ | H | Br | SO₂Ph |
| 25 | CONEt₂ | H | Br | SO₂Ph |
| 26 | CON(nPr)₂ | H | Br | SO₂Ph |

TABLE 38-continued

| Compd No | R⁴ | R⁶ | R⁷ | R⁸ |
|---|---|---|---|---|
| 27 | CONHPh | H | CN | SO₂Ph |
| 28 | acetylpyrrolidine | H | Br | SO₂Ph |
| 29 | acetylpiperidine | H | Br | SO₂Ph |
| 30 | acetylazepane | H | Br | SO₂Ph |
| 31 | NHCOOMe | H | Br | SO₂Ph |
| 32 | NHCOOEt | H | CN | SO₂Ph |
| 33 | NHCOO-tBu | H | Br | SO₂Ph |

TABLE 39

| Compd No | R⁴ | R⁶ | R⁷ | R⁸ |
|---|---|---|---|---|
| 1 | NHCOOCH₂Ph | H | Br | SO₂Ph |
| 2 | NMeCOOMe | H | Br | SO₂Ph |
| 3 | N(nPr)COOMe | H | CN | SO₂Ph |
| 4 | NMeCOOCH₂Ph | H | Br | SO₂Ph |
| 5 | N(nPr)COOCH₂Ph | H | Br | SO₂Ph |
| 6 | COOH | H | Ph | SO₂Ph |
| 7 | COOMe | H | Ph | SO₂Ph |
| 8 | COOEt | H | Ph | SO₂Ph |
| 9 | COO-tBu | H | Ph | SO₂Ph |
| 10 | CONH₂ | H | Ph | SO₂Ph |
| 11 | CONHMe | H | Ph | SO₂Ph |
| 12 | CONHEt | H | Ph | SO₂Ph |
| 13 | CONH-nPr | H | Ph | SO₂Ph |
| 14 | CONMe₂ | H | Ph | SO₂Ph |
| 15 | CONEt₂ | H | Ph | SO₂Ph |
| 16 | CON(nPr)₂ | H | Ph | SO₂Ph |
| 17 | CONHPh | H | Ph | SO₂Ph |
| 18 | acetylpyrrolidine | H | Ph | SO₂Ph |
| 19 | acetylpiperidine | H | Ph | SO₂Ph |
| 20 | acetylazepane | H | Ph | SO₂Ph |
| 21 | NHCOOMe | H | Ph | SO₂Ph |
| 22 | NHCOOEt | H | Ph | SO₂Ph |
| 23 | NHCOO-tBu | H | Ph | SO₂Ph |
| 24 | NHCOOCH₂Ph | H | Ph | SO₂Ph |
| 25 | NMeCOOMe | H | Ph | SO₂Ph |
| 26 | N(nPr)COOMe | H | Ph | SO₂Ph |
| 27 | NMeCOOCH₂Ph | H | Ph | SO₂Ph |
| 28 | N(nPr)COOCH₂Ph | H | Ph | SO₂Ph |
| 29 | OH | COOMe | H | H |
| 30 | OMe | COOMe | H | H |
| 31 | OH | COOMe | Me | H |
| 32 | OMe | COOMe | Me | H |
| 33 | OH | COOMe | Br | H |
| 34 | OMe | COOMe | Br | H |
| 35 | OH | COOMe | Ph | H |
| 36 | OMe | COOMe | Ph | H |
| 37 | OH | COOMe | H | Me |
| 38 | OMe | COOMe | H | Me |

TABLE 40

| Comp No | R⁴ | R⁶ | R⁷ | R⁸ |
|---|---|---|---|---|
| 1 | OH | COOMe | Me | Me |
| 2 | OMe | COOMe | Et | Me |
| 3 | OH | COOMe | Br | Me |
| 4 | OMe | COOMe | Br | Me |
| 5 | OH | COOMe | Ph | Me |
| 6 | OMe | COOMe | Ph | Me |
| 7 | OH | COOMe | H | COPh |
| 8 | OMe | COOMe | H | COPh |
| 9 | OH | COOMe | Me | COPh |
| 10 | OMe | COOMe | nPr | COPh |
| 11 | OH | COOMe | Br | COPh |
| 12 | OMe | COOMe | CN | COPh |
| 13 | OH | COOMe | CN | COPh |
| 14 | OMe | COOMe | Ph | COPh |
| 15 | OH | COOMe | H | SO₂Ph |
| 16 | OMe | COOMe | CN | SO₂Ph |
| 17 | OH | COOMe | Et | SO₂Ph |
| 18 | OMe | COOMe | Me | SO₂Ph |
| 19 | OH | COOMe | CN | SO₂Ph |
| 20 | OMe | COOMe | Br | SO₂Ph |
| 21 | OH | COOMe | Ph | SO₂Ph |
| 22 | OMe | COOMe | CN | SO₂Ph |
| 23 | OH | COOEt | H | H |
| 24 | OMe | COOEt | H | H |
| 25 | OH | COOEt | nPr | H |
| 26 | OMe | COOEt | Et | H |
| 27 | OH | COOEt | Br | H |
| 28 | OMe | COOEt | CN | H |
| 29 | OH | COOEt | Ph | H |
| 30 | OMe | COOEt | CN | H |
| 31 | OH | COOEt | H | Me |
| 32 | OMe | COOEt | H | Me |
| 33 | OH | COOEt | nPr | Me |
| 34 | OMe | COOEt | CN | Me |
| 35 | OH | COOEt | Br | Me |
| 36 | OMe | COOEt | CN | Me |
| 37 | OH | COOEt | Ph | Me |
| 38 | OMe | COOEt | Ph | Me |
| 39 | OH | COOEt | H | COPh |
| 40 | OMe | COOEt | CN | COPh |
| 41 | OH | COOEt | Me | COPh |

TABLE 41

| Comp No | R⁴ | R⁶ | R⁷ | R⁸ |
|---|---|---|---|---|
| 1 | OMe | COOEt | Et | COPh |
| 2 | OH | COOEt | Br | COPh |
| 3 | OMe | COOEt | CN | COPh |
| 4 | OH | COOEt | Ph | COPh |
| 5 | OMe | COOEt | CN | COPh |
| 6 | OH | OQOEt | H | SO₂Ph |

TABLE 41-continued

| Comp No | $R^4$ | $R^6$ | $R^7$ | $R^8$ |
|---|---|---|---|---|
| 7 | OMe | OQOEt | H | $SO_2Ph$ |
| 8 | OH | COOEt | Me | $SO_2Ph$ |
| 9 | OMe | COOEt | nPr | $SO_2Ph$ |
| 10 | OH | COOEt | CN | $SO_2Ph$ |
| 11 | OMe | COOEt | Br | $SO_2Ph$ |
| 12 | OH | COOEt | Ph | $SO_2Ph$ |
| 13 | OMe | COOEt | Ph | $SO_2Ph$ |
| 14 | OH | CN | H | H |
| 15 | OMe | CN | CN | H |
| 16 | OH | CN | Me | H |
| 17 | OMe | CN | Et | H |
| 18 | OH | CN | Br | H |
| 19 | OMe | CN | CN | H |
| 20 | OH | CN | Ph | H |
| 21 | OMe | CN | Ph | H |
| 22 | OH | CN | H | Me |
| 23 | OMe | CN | H | Me |
| 24 | OH | CN | CN | Me |
| 25 | OMe | CN | Me | Me |
| 26 | OH | CN | Br | Me |
| 27 | OMe | CN | Br | Me |
| 28 | OH | CN | Ph | Me |
| 29 | OMe | CN | CN | Me |
| 30 | OH | CN | H | COPh |
| 31 | OMe | CN | H | COPh |
| 32 | OH | CN | CN | COPh |
| 33 | OMe | CN | Et | COPh |
| 34 | OH | CN | Br | COPh |
| 35 | OMe | CN | Br | COPh |
| 36 | OH | CN | Ph | COPh |
| 37 | OMe | CN | CN | COPh |
| 38 | OH | CN | H | $SO_2Ph$ |
| 39 | OMe | CN | H | $SO_2Ph$ |
| 40 | OH | CN | nPr | $SO_2Ph$ |
| 41 | OMe | CN | nPr | $SO_2Ph$ |

TABLE 42

| Comp No | $R^4$ | $R^6$ | $R^7$ | $R^8$ |
|---|---|---|---|---|
| 1 | OH | CN | Br | $SO_2Ph$ |
| 2 | OMe | CN | Br | $SO_2Ph$ |
| 3 | OH | CN | CN | $SO_2Ph$ |
| 4 | OMe | CN | Ph | $SO_2Ph$ |
| 5 | OH | $CH_2NH_2$ | H | H |
| 6 | OMe | $CH_2NH_2$ | H | H |
| 7 | OH | $CH_2NH_2$ | nPr | H |
| 8 | OMe | $CH_2NH_2$ | Me | H |
| 9 | OH | $CH_2NH_2$ | Br | H |
| 10 | OMe | $CH_2NH_2$ | CN | H |
| 11 | OH | $CH_2NH_2$ | Ph | H |
| 12 | OMe | $CH_2NH_2$ | Ph | H |
| 13 | OH | $CH_2NH_2$ | CN | Me |
| 14 | OMe | $CH_2NH_2$ | H | Me |
| 15 | OH | $CH_2NH_2$ | Et | Me |
| 16 | OMe | $CH_2NH_2$ | CN | Me |
| 17 | OH | $CH_2NH_2$ | Br | Me |
| 18 | OMe | $CH_2NH_2$ | Br | Me |
| 19 | OH | $CH_2NH_2$ | Ph | Me |
| 20 | OMe | $CH_2NH_2$ | CN | Me |
| 21 | OH | $CH_2NH_2$ | H | COPh |
| 22 | OMe | $CH_2NH_2$ | H | COPh |
| 23 | OH | $CH_2NH_2$ | nPr | COPh |
| 24 | OMe | $CH_2NH_2$ | nPr | COPh |
| 25 | OH | $CH_2NH_2$ | Br | COPh |
| 26 | OMe | $CH_2NH_2$ | Br | COPh |
| 27 | OH | $CH_2NH_2$ | Ph | COPh |
| 28 | OMe | $CH_2NH_2$ | Ph | COPh |
| 29 | OH | $CH_2NH_2$ | H | $SO_2Ph$ |
| 30 | OMe | $CH_2NH_2$ | H | $SO_2Ph$ |
| 31 | OH | $CH_2NH_2$ | Me | $SO_2Ph$ |
| 32 | OMe | $CH_2NH_2$ | Me | $SO_2Ph$ |

TABLE 42-continued

| Comp No | $R^4$ | $R^6$ | $R^7$ | $R^8$ |
|---|---|---|---|---|
| 33 | OH | $CH_2NH_2$ | CN | $SO_2Ph$ |
| 34 | OMe | $CH_2NH_2$ | Br | $SO_2Ph$ |
| 35 | OH | $CH_2NH_2$ | CN | $SO_2Ph$ |
| 36 | OMe | $CH_2NH_2$ | Ph | $SO_2Ph$ |

EXPERIMENTALS

A mixture of radioactive ligands and some cardinal numbers of test compounds was incubated with a sample of cell membrane, which was prepared from brain of rats or HEK293 cells, which expressed the receptor, under the following conditions. Then, the sample was filtered by suction on a Whatman GF/C. Radioactivity on the filter was encountered by the use of a liquid scintillation counter. 50% Inhibitory concentration values ($IC_{50}$ values) of each selective binding were calculated for test compounds and the Ki value was obtained by applying an equation of Cheng-Prusoff [*Biochem. Pharmacol.* 22 (1973) 3099–3108] $Ki=IC_{50}/(1+[L]/Kd)$. [L] represents a concentration of the radio ligand used and Kd shows dissociation constant.

TABLE 43

| Receptor | Origin | Radioactive Ligand | Condition of Incubation |
|---|---|---|---|
| 5-HT1A | Rat hippocampus | 1 nM [$^3$H] 8-OH-DPAT | 25° C. 30 min |
| 5-HT2 | Rat cerebral cortex | 1 nM [$^3$H] Ketanserin | 37° C. 30 min |
| 5-HT6 | rat5-$HT_6$ (HEK293) | 8 nM [$^3$H] 5HT<br>4 nM [$^3$H] LSD | 25° C. 120 min<br>37° C. 60 min |
| 5-HT7 | Human 5-$HT_7$ (HEK293) | 0.5 nM [$^3$H] 5CT | 25° C. 120 min |

TABLE 44

| | | Ki value (nM) ±SE | | |
|---|---|---|---|---|
| Example | Compd. No. | 5-HT1A | 5-HT6 | 5-HT7 |
| 5 | 8-1 | 36 | | |
| 12 | 19-1 | 81 | | |
| 12 | 19-2 | 23 | 97 | |
| 12 | 19-3 | 5.7 | | 46 |
| 12 | 19-5 | 10 | | |
| 12 | 19-7 | 19 | | |
| 12 | 19-10 | 2.5 | | |
| 12 | 19-15 | 7.7 | 4.6 | 16 |
| 12 | 19-16 | 58 | 62 | 86 |
| 12 | 19-18 | | 2.7 | |
| 12 | 19-19 | 3.8 | | |
| 13 | 20-1 | | 1.7 | |
| 13 | 20-5 | | 0.49 | |
| 13 | 20-6 | | 2.7 | |
| 13 | 20-9 | 86 | 78 | |
| 13 | 20-10 | 95 | 45 | |
| 13 | 20-11 | | 5.7 | |
| 13 | 20-12 | | 2.7 | |
| 13 | 20-13 | | 3.9 | |
| 13 | 20-14 | | 22 | |
| 13 | 20-15 | | 29 | |
| 13 | 20-16 | | 22 | |
| 13 | 20-17 | | 29 | |
| 13 | 20-18 | | 22 | |
| 13 | 20-19 | | 12 | |
| 13 | 20-20 | | 11 | |
| 13 | 20-21 | | 2.7 | |

TABLE 44-continued

| Example | Compd. No. | 5-HT1A | 5-HT6 | 5-HT7 |
|---------|-----------|--------|-------|-------|
| 13 | 20-22 | | 26 | |
| 13 | 20-23 | | 9.9 | |
| 13 | 20-24 | | 3.2 | |
| 13 | 20-25 | | 36 | |
| 14 | 21 | 14 | | |
| 24 | 36-1 | 29 | 65 | |
| 24 | 36-2 | | 8.5 | |
| 24 | 36-3 | 58 | 4.2 | |
| 24 | 36-4 | | | |
| 26 | 38 | 83 | | 22 |
| 27 | 39 | 27 | | 73 |
| 28 | 40 | 15 | 32 | 74 |
| 29 | 41 | 57 | | |
| 34 | 46-2 | | | |
| 34 | 46-3 | 18 | | |
| 34 | 46-1 | | 28 | |
| 35 | 47 | | 78 | |
| 36 | 48 | | 1 | |

INDUSTRIAL APPLICABILITY

Having an affinity against serotonin receptors, compounds described in this invention are useful as medicines such as therapeutic agents of diseases for central nervous systems thereof. Furthermore, these compounds are useful as synthetic intermediates thereof.

What is claimed is:

1. A compound, prodrug, pharmaceutically acceptable salt or solvate thereof of the formula:

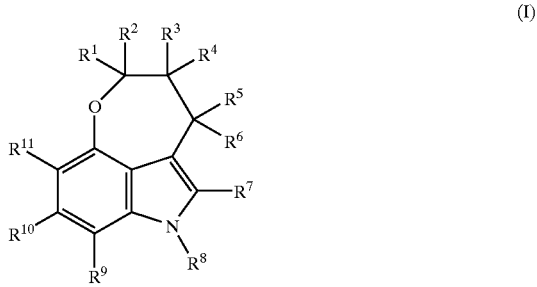

(I)

wherein
$R^1$ is hydrogen;
$R^2$ is hydrogen or lower alkyl;
$R^3$ is hydrogen;
$R^4$ is —$COOR^{13}$ wherein $R^{13}$ is hydrogen or ester moiety;
$R^5$ is hydrogen, or $R^3$ and $R^5$ taken together may form a bond;
$R^6$ is hydrogen;
$R^7$ is hydrogen, halogen, optionally substituted lower alkyl, cycloalkyl, or cycloalkyl(lower)alkyl;
$R^8$ is hydrogen, optionally substituted lower alkyl, cycloalkyl, or cycloalkyl(lower)alkyl; and
$R^9$, $R^{10}$ and $R^{11}$ are each independently hydrogen, halogen, optionally substituted lower alkyl, cycloalkyl, or cycloalkyl(lower)alkyl.

2. A compound, prodrug, pharmaceutically acceptable salt or solvate thereof, according to claim 1, wherein $R^2$ is hydrogen.

3. A compound, prodrug, pharmaceutically acceptable salt or solvate thereof, according to claim 1, wherein $R^3$ is hydrogen.

4. A compound, prodrug, pharmaceutically acceptable salt or solvate thereof, according to claim 1, wherein $R^5$ is hydrogen.

5. A compound, prodrug, pharmaceutically acceptable salt or solvate thereof, according to claim 1, wherein $R^3$ and $R^5$ taken together may form a bond.

6. A compound, prodrug, pharmaceutically acceptable salt or solvate thereof, according to claim 1, wherein $R^4$ represents —$COOR^{13}$ wherein $R^{13}$ is hydrogen or lower alkyl.

7. A compound, prodrug, pharmaceutically acceptable salt or solvate thereof, according to claim 1, wherein $R^4$ is —$COOR^{13}$ wherein $R^{13}$ is hydrogen or methyl.

8. A compound, prodrug, pharmaceutically acceptable salt or solvate thereof, according to claim 1, wherein $R^7$ is hydrogen, lower alkyl, or halogen.

9. A compound, prodrug, pharmaceutically acceptable salt or solvate thereof, according to claim 1, wherein $R^7$ is hydrogen, methyl, ethyl, or halogen.

10. A compound, prodrug, pharmaceutically acceptable salt or solvate thereof, according to claim 1, wherein $R^8$ is hydrogen, or optionally substituted lower alkyl.

11. A compound, prodrug, pharmaceutically acceptable salt or solvate thereof, according to claim 1, wherein $R^8$ is hydrogen.

12. A compound, prodrug, pharmaceutically acceptable salt or solvate thereof, according to claim 1, wherein all of $R^9$, $R^{10}$ and $R^{11}$ are hydrogen.

13. A compound, prodrug, pharmaceutically acceptable salt or solvate thereof, according to claim 1, wherein $R^2$ is hydrogen, $R^3$ and $R^5$ are hydrogen or taken together may form a bond.

14. A compound, prodrug, pharmaceutically acceptable salt or solvate thereof, according to claim 1, wherein all of $R^9$, $R^{10}$ and $R^{11}$ are hydrogen; wherein $R^2$ is hydrogen; wherein $R^3$ and $R^5$ are hydrogen or together form a bond; wherein $R^6$ is hydrogen; $R^7$ is hydrogen, lower alkyl, or halogen and $R^8$ is hydrogen, or lower alkyl.

15. A compound, prodrug, pharmaceutically acceptable salt or solvate thereof, according to claim 1, wherein $R^9$ is hydrogen or halogen.

16. A compound, prodrug, pharmaceutically acceptable salt or solvate thereof, according to claim 1, wherein $R^9$ is hydrogen.

17. A compound, prodrug, pharmaceutically acceptable salt or solvate thereof, according to claim 1, wherein $R^{10}$ is hydrogen.

18. A compound, prodrug, pharmaceutically acceptable salt or solvate thereof, according to claim 1, wherein $R^{11}$ is hydrogen, halogen, or lower alkyl.

19. A compound, prodrug, pharmaceutically acceptable salt or solvate thereof, according to claim 1, wherein $R^{11}$ is hydrogen, halogen, or methyl.

20. A compound, prodrug, pharmaceutically acceptable salt or solvate thereof, according to claim 1, wherein $R^1$, $R^2$, $R^3$, $R^5$, $R^6$, $R^9$, and $R^{10}$ is hydrogen; $R^7$ is hydrogen, halogen, or lower alkyl, $R^8$ is hydrogen and $R^{11}$ is hydrogen, halogen, or lower alkyl.

21. A pharmaceutical composition comprising a compound, prodrug, pharmaceutically acceptable salt or solvate thereof according to claim 1, together with a pharmaceutically acceptable additive thereof.

22. A method for preparing a therapeutic or prophylactic medicament for a serotonin receptor mediated disease, which comprises mixing a compound, prodrug, pharmaceutically acceptable salt or solvate thereof according to claim 1, together with a pharmaceutically acceptable additive thereof.

* * * * *